US008383865B2

(12) United States Patent
DiMauro

(10) Patent No.: US 8,383,865 B2
(45) Date of Patent: Feb. 26, 2013

(54) CURCUMIN DERIVATIVES

(75) Inventor: Thomas M. DiMauro, Southboro, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 364 days.

(21) Appl. No.: 12/571,303

(22) Filed: Sep. 30, 2009

(65) Prior Publication Data

US 2010/0087527 A1 Apr. 8, 2010

Related U.S. Application Data

(63) Continuation-in-part of application No. PCT/US2008/060569, filed on Apr. 17, 2008, which is a continuation-in-part of application No. 11/736,278, filed on Apr. 17, 2007, now abandoned, and a continuation-in-part of application No. 12/029,904, filed on Feb. 12, 2008.

(51) Int. Cl.
*C07C 43/20* (2006.01)
*C07C 43/205* (2006.01)
*C07C 43/215* (2006.01)

(52) U.S. Cl. ............. 568/646; 568/631; 568/644; 560/8

(58) Field of Classification Search ................... None
See application file for complete search history.

(56) References Cited

U.S. PATENT DOCUMENTS

| | | |
|---|---|---|
| 2,955,898 A | 10/1960 | Bailey |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,205,399 A | 6/1980 | Shalaby et al. |
| 4,208,511 A | 6/1980 | Shalaby et al. |
| 4,482,722 A | 11/1984 | Thorbek et al. |
| 4,529,556 A | 7/1985 | Bruza |
| 5,073,641 A | 12/1991 | Bundgaard et al. |
| 5,334,315 A | 8/1994 | Matkovich et al. |
| 5,340,808 A | 8/1994 | Jaen et al. |
| 5,401,777 A | 3/1995 | Ammon et al. |
| 5,462,667 A | 10/1995 | Wollinsky et al. |
| 5,464,929 A | 11/1995 | Bezwada et al. |
| 5,595,751 A | 1/1997 | Bezwada et al. |
| 5,597,579 A | 1/1997 | Bezwada et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,622,944 A | 4/1997 | Hale et al. |
| 5,645,850 A | 7/1997 | Bezwada et al. |
| 5,648,088 A | 7/1997 | Bezwada et al. |
| 5,679,864 A | 10/1997 | Krackov et al. |
| 5,698,213 A | 12/1997 | Jamiolkowski et al. |
| 5,700,583 A | 12/1997 | Jamiolkowski et al. |
| 5,859,150 A | 1/1999 | Jamiolkowski et al. |
| 5,876,714 A | 3/1999 | Nishikawa et al. |
| 5,891,924 A | 4/1999 | Aggarwal |
| 5,980,480 A | 11/1999 | Rubenstein et al. |
| 5,980,481 A | 11/1999 | Gorsuch |
| 6,096,740 A | 8/2000 | Mechoulam et al. |
| 6,187,332 B1 | 2/2001 | Gern et al. |
| 6,234,991 B1 | 5/2001 | Gorsuch |
| 6,482,866 B1 | 11/2002 | Dahayanaka et al. |
| 6,489,308 B1 | 12/2002 | Shapiro |
| 6,500,213 B1 | 12/2002 | Braun et al. |
| 6,656,227 B2 | 12/2003 | Levin |
| 6,790,979 B2 | 9/2004 | Lee |
| 6,831,108 B2 | 12/2004 | Dahanayake et al. |
| 6,866,856 B2 | 3/2005 | Lu et al. |
| 6,884,783 B2 | 4/2005 | Jia et al. |
| 6,900,356 B2 | 5/2005 | Gokaraju et al. |
| 7,025,742 B2 | 4/2006 | Rubenstein et al. |
| 7,060,733 B2 | 6/2006 | Pandol et al. |
| 7,205,011 B2 | 4/2007 | Chen |
| 7,351,745 B2 | 4/2008 | Dryer et al. |
| 7,371,744 B2 | 5/2008 | Brown et al. |
| 7,416,559 B2 | 8/2008 | Shalaby |
| 7,462,459 B2 | 12/2008 | Zerangue |
| 7,582,068 B2 | 9/2009 | Koullick et al. |
| 7,723,515 B1 | 5/2010 | DiMauro |
| 7,745,670 B2 | 6/2010 | DiMauro |
| 7,906,643 B2 | 3/2011 | DiMauro |
| 2001/0051184 A1 | 12/2001 | Heng |
| 2002/0019382 A1 | 2/2002 | Snyder et al. |

(Continued)

FOREIGN PATENT DOCUMENTS

| | | |
|---|---|---|
| CN | 1312106 | 3/2003 |
| CN | 1970548 | 11/2008 |
| EP | 0504 263 B1 | 9/1992 |
| JP | 2000-236843 A | 9/2000 |
| WO | WO 90/08128 A1 | 7/1990 |
| WO | WO 95/18606 A1 | 7/1995 |
| WO | WO 01/40188 A1 | 6/2001 |

(Continued)

OTHER PUBLICATIONS

Rajakumar et al Synthesis 2006, 8, 1257-1262.*

(Continued)

*Primary Examiner* — Yevegeny Valenrod
(74) *Attorney, Agent, or Firm* — Hamilton, Brook, Smith & Reynolds, P.C.

(57) ABSTRACT

The present invention is directed to a compound represented by Structural Formula (I):

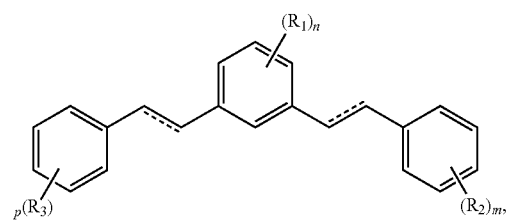

or a pharmaceutically acceptable salt thereof. The variables for Structural Formula (I) are defined herein. Also described is a pharmaceutical composition comprising the compound of Structural Formula (I) and its therapeutic use.

8 Claims, 18 Drawing Sheets

U.S. PATENT DOCUMENTS

| | | |
|---|---|---|
| 2003/0108628 A1 | 6/2003 | Babish et al. |
| 2003/0147979 A1 | 8/2003 | Mae et al. |
| 2003/0153512 A1 | 8/2003 | Hergenhahn et al. |
| 2003/0157155 A1 | 8/2003 | Lipp et al. |
| 2003/0199594 A1 | 10/2003 | Shah |
| 2004/0127470 A1 | 7/2004 | Masferrer |
| 2004/0127556 A1 | 7/2004 | Lu et al. |
| 2004/0220113 A1 | 11/2004 | Shapiro |
| 2004/0220239 A1 | 11/2004 | Shapiro |
| 2004/0220242 A1 | 11/2004 | Shapiro |
| 2004/0220510 A1 | 11/2004 | Koullick et al. |
| 2005/0020945 A1 | 1/2005 | Tosaya et al. |
| 2005/0031651 A1 | 2/2005 | Gervais et al. |
| 2005/0038371 A1 | 2/2005 | Reich et al. |
| 2005/0164957 A1 | 7/2005 | Jia et al. |
| 2005/0169960 A1 | 8/2005 | Hunter et al. |
| 2005/0169961 A1 | 8/2005 | Hunter et al. |
| 2005/0181005 A1 | 8/2005 | Hunter et al. |
| 2005/0181009 A1 | 8/2005 | Hunter et al. |
| 2005/0181036 A1 | 8/2005 | Aggarwal et al. |
| 2005/0187140 A1 | 8/2005 | Hunter et al. |
| 2005/0267221 A1 | 12/2005 | Wellen |
| 2006/0020329 A1 | 1/2006 | Raze et al. |
| 2006/0067998 A1 | 3/2006 | Kurzrock et al. |
| 2006/0134059 A1 | 6/2006 | Dryer et al. |
| 2006/0134155 A1 | 6/2006 | Dryer et al. |
| 2006/0134231 A1 | 6/2006 | Hines et al. |
| 2006/0195142 A1 | 8/2006 | Shalaby |
| 2006/0224234 A1 | 10/2006 | Jayaraman |
| 2006/0240007 A1 | 10/2006 | Sanders |
| 2006/0264423 A1 | 11/2006 | Wood |
| 2006/0264497 A1 | 11/2006 | Zeligs |
| 2007/0010435 A1 | 1/2007 | Frangione et al. |
| 2007/0060644 A1 | 3/2007 | Vander Jagt et al. |
| 2007/0116757 A1 | 5/2007 | Rariy |
| 2007/0134305 A1 | 6/2007 | Zilberman |
| 2007/0224671 A1 | 9/2007 | Shapiro |
| 2007/0243132 A1 | 10/2007 | Jones et al. |
| 2007/0281045 A1 | 12/2007 | Tripp et al. |
| 2008/0051691 A1 | 2/2008 | Dragoon et al. |
| 2008/0075671 A1 | 3/2008 | Di Mauro |
| 2008/0076821 A1 | 3/2008 | Di Mauro |
| 2008/0082036 A1 | 4/2008 | Trescony et al. |
| 2008/0090897 A1 | 4/2008 | Steiner et al. |
| 2008/0153912 A1 | 6/2008 | Dryer et al. |
| 2008/0160109 A1 | 7/2008 | Dryer et al. |
| 2008/0175895 A1 | 7/2008 | Kogure et al. |
| 2008/0201786 A1 | 8/2008 | Rubinstein |
| 2008/0213404 A1 | 9/2008 | Johnson et al. |
| 2008/0241352 A1 | 10/2008 | Shalaby |
| 2008/0247987 A1 | 10/2008 | Liggins et al. |
| 2008/0275016 A1 | 11/2008 | Arbiser |
| 2009/0047371 A1 | 2/2009 | Turini et al. |
| 2009/0087385 A1 | 4/2009 | DiMauro |
| 2009/0131850 A1 | 5/2009 | Geiger |
| 2009/0325963 A1 | 12/2009 | Lilienfeld |
| 2009/0326275 A1 | 12/2009 | DiMauro |
| 2010/0087527 A1 | 4/2010 | DiMauro |
| 2010/0286585 A1 | 11/2010 | DiMauro |
| 2010/0292512 A1 | 11/2010 | DiMauro |
| 2011/0130392 A1 | 6/2011 | DiMauro et al. |
| 2011/0257587 A1 | 10/2011 | Lilienfeld et al. |

FOREIGN PATENT DOCUMENTS

| | | |
|---|---|---|
| WO | WO 2004/014843 A1 | 2/2004 |
| WO | WO 2008/051474 A1 | 5/2008 |
| WO | WO 2008/131059 | 10/2008 |
| WO | WO 2009/073050 A3 | 6/2009 |
| WO | WO 2010/085739 A1 | 7/2010 |

OTHER PUBLICATIONS

Byeon et al Bioorganic & Medicinal Chemistry Letters, 2007, 17, 1466).*

Banker, G.S. et al, "Modern Pharmaceutics, 3ed.", Marcel Dekker, New York, 1996, p. 596.*

Wolff, Manfred E. "Burger's Medicinal Chemistry, 5ed, Part I", John Wiley & Sons, 1995, pp. 975-977.*

Non-Final Office Action mailed Feb. 3, 2012 in pending U.S. Appl. No. 12/779,486.

Patani, G.A., et al., "Bioisosterism: A Rational Approach in Drug Design" *Chem. Rev*,96(8): 3147-3176 (1996).

Leung, M.H.M., et al., "Encapsulation of Curcumin in Cationic Micelles Suppresses Alkaline Hydrolysis," *Langmuir*, 24:5672-5675 (2008).

Kaewnopparat, N., et al., "Increased Solubility, Dissolution and Physicochemical Studies of Curcumin-Polyvinylpyrrolidone K-30 Solid Dispersions," *World Academy of Science, Engineering and Technology*, 55:229-234 (2009).

Kurien, B.T., et al., "Improving the Solubility and Pharmacological Efficacy of Curcumin by Heat Treatment," *Assay Drug Dev. Technol.*, 5(4):567-76 (Aug. 2007).

Salmaso, S., et al., "New Cyclodextrin Bioconjugates for Active Tumour Targeting," *Journal of Drug Targeting*, 15(6):379-390 (Jul. 2007).

Abla, "Effect of Charge and Molecular Weight on Transdermal Peptide Delivery of Iontophoresis"; *Pharm. Res*; Dec. 2005; pp. 2069-2078; vol. 22(12).

Alas, "Inhibition of Constitutive STAT3 Activity Sensitizes Resistant Non-Hodgkin's Lymphoma and Multiple Myeloma to Chemotherapeutic Drug-Mediated Apoptosis"; *Clin. Cancer Res.*; Jan. 2003; pp. 316-326; vol. 9(1).

Al-Ghananeem, "Targeted Brain Delivery of 17β-Estradiol Via Nasally Administered Water Soluble Prodrugs"; *AAPS PharmSciTech*; 2002; pp. 1-8; vol. 3(1); article 5.

Allcock, "Polyphosphazenes"; *The Encyclopedia of Polymer Science*; 1988; pp. 31-41; vol. 13; Wiley Intersciences, John Wiley & Sons.

Altomare, "Highly Water-soluble Derivatives of the Anesthetic Agent Propofol: in vitro and in vivo Evaluation of Cyclic Amino Acid Esters"; *Eur. J. Pharm. Sci.*; 2003; pp. 17-26; vol. 20.

Anderson, "α-Amino Acid Phenolic Ester Derivatives: Novel Water-Soluble General Anesthetic Agents Which Allosterically Modulate $GABA_A$ Receptors"; *J. Med Chem.*; 2001; pp. 3582-3591; vol. 44.

Anderson, "Strategies in the Design Solution-Stable, Water-Soluble Prodrugsii: Properties of Micellar Prodrugs of Methylprednisolone"; *Journal of Pharmaceutical Sciences*; 2006; pp. 375-381; vol. 74(4).

Anekonda, "Resveratrol—A Boon for Treating Alzheimer's Disease?"; *Brain Research Reviews*; 2006; pp. 316-326; vol. 52; Elsevier.

Araujo, "Biologic Activities of Curcuma longa L."; *Mem Inst Oswaldo Cruz*; 2001; pp. 723-728; vol. 96(5).

Atamna, "Methylene Blue Delays Cellular Senescence and Enhances Key Mitochondrial Biochemical Pathways"; *FASEB J.*, Mar. 2008; pp. 703-712; vol. 22(3).

Auld, "Probing Weakly Polar Interactions in Cytochrome"; *Protein Science*; 1993; pp. 2187-2197; vol. 2.

Barakat, "Carbamazepine Uptake into Rat Brain Following Intraolfactory Transport"; *J. Pharm. Pharmacol.*; Jan. 2006; pp. 63-72; 58(1).

Barthram, "Effects of Ligand Topology on the Properties of Dinuclear Ruthenium Complexes of Bis-Semiquinone Bridging Ligands"; *Inorganica Chimica Acta*; 1998; pp. 1-5; vol. 267.

Basile, "Curcumin Derivatives: Molecular Basis of Their Anti-Cancer Activity"; *Biochem Pharmacol.*; Jul. 3, 2009; pp. 1305-1315.

Bastianetto, "Neuroprotective Abilities of Resveratrol and Other Red Wine Constituents Against Nitric Oxide-related Toxicity in Cultured Hippocampal Neurons"; *Br. J. Pharm.*; 2000; pp. 711-720; vol. 131.

Basu, "Differential and Special Properties of the Major Human UGT1-encoded Gastrointestinal UDP-glucuronosyltransferases Enhance Potential to Contain Chemical Uptake"; *J. Biol. Chem.*; 2004; pp. 1429-1441; vol. 279.

Basu, "Evidence for Phosphorylation Requirement for Human Bilirubin UDP-glucuronosyltransferase (UGT1A1) Activity"; *Biochem. Biophys. Res. Comm.*; 2003; pp. 98-104; vol. 303.

Basu, "Human UDP-Glucuronosyltransferases Show Atypical Metabolism of Mycophenolic Acid and Inhibition by Curcumin"; *Drug. Metab. Dispos.*; Jul. 2004; pp. 768-773; vol. 32(7).

Basu, "Phosphorylation of a UDP-glucuronosyltransferase Regulates Substrate Specificity"; *PNAS*; May 3; 2005; pp. 6285-6290; vol. 102(18).

Begum, "Curcumin Structure-Function, Bioavailability and Efficacy in Models of Neuroinflammation and Alzheimer's Disease"; *J. Pharmacol Exp The*; Apr. 16, 2008; pp. 196-208; vol. 326 (1).

Belguendouz, "Resveratrol Inhibits Metal Ion-dependent and Independent Peroxidation of Porcine Low-density Lipoproteins"; *Biochemical Pharmacology*; 1997; 1347-1355; vol. 53.

Bender, "Etofenamate Levels in Human Serum and Synovial Fluid Following Iontophoresis"; *Arzneimittelforschung*; 2001; pp. 489-492; vol. 51(6).

Bundgaard, "Water soluble, Solution-stable, and Biolabile n-substituted (aminomethyl) Benzoate Ester Prodrugs of Acyclovir"; *Pharm. Res.*; 1991; pp. 1087-1093; vol. 8 (9).

Castuma, "The Influence of Fatty Acid Unsaturation and Physical Properties of Microsomal Membrane Phospholipids on UDP-glucuronyltransferase Activity"; *Biochem. J.*; 1989; 732-731; vol. 258.

Chavanpatil, "Nasal Drug Delivery of Sumatriptan Succinate"; *Pharmazie*; May 2005; pp. 374-379; vol. 60(5).

Chearwae, "Curcuminoids Purified from Turmeric Powder Modulate The Function of Human Multidry Resistance Protein 1 (ABCC1)"; *Cancer Chemother. Pharmacol.*; 2006; pp. 376-388; vol. 57(3).

Chen, "Curcumin and its Analogues as Potent Inhibitors of Low Density Lipoprotein Oxidation: H-atom Abstraction From the Phenolic Groups and Possible Involvement of the 4-hydroxy-3-methoxyphenyl Groups"; *Free Rad. Biol. Med.*; Feb. 2006; pp. 526-535; vol. 40(3).

Chen, "SIRT1 Protects Against Microglia-dependent Amyloid-B toxicity Through Inhibiting NF-KB Signaling"; *J. Biol. Chem.*; 2005, pp. 40364-40374; vol. 280(48).

Cohn, "Biodegradable PEO-PLA Block Copolymers"; *Journal of Biomedical Materials Research*; 1988; pp. 993-1009; vol. 22.

Cohn, "Polymer Preprints"; *Journal of Biomaterials Research*; 1999, vol. 30(1), p. 498.

Cole, "Prevention of Alzheimer's Disease: Omega-3 fatty Acid and Phenolic Anti-oxidant Interventions"; *Neurobiol. Aging*; 26S; (2005); S133-S136.

Conjeevaram, "Iontophoretic in vivo transdermal delivery of B-blockers in hairless rats and reduced skin irritation by liposomal formulation"; *Pharm Res.*; Sep. 2003; pp. 1496-1501; vol. 20(9).

Cruz-Correa, "Combination Treatment With Curcumin and Quercetin of Adenomas in Familial Adenomatous Polyposis"; *Clin. Gastroent. Hepat.*, 2006; pp. 1035-1038; vol. 4.

Curecurmin Bioresonant Phytotherapeutic Nasal Spray Brochure, Bioonic Phytoceuticals, 2006.

Defelice, "Targeting the Neurotoxic Species in Alzheimer's Disease: Inhibitors of Abeta Oligomerization"; *FASEB J.*; Sep. 2004; pp. 1366-1372; vol. 18(12).

Denet, "Transdermal delivery of timolol and atenolol using electroporation and iontophoresis in combination:a mechanist approach"; *Pharm Res*. Dec. 2003; pp. 1946-1951; vol. 20(12).

Do, "Reverse Pharmacognosy: Application of Selnergy, a New Tool for Lead Discovery. The Example of ε-Viniferin"; *Current Drug Disc Tech*; 2005; pp. 161-167; vol. 2.

Eljamel, "ALA and Photofrin Fluorescence-Guided Resection and Repetitive PDT in Glioblastoma Multiforme: A Single Centre Phase III Randomised Controlled Trial"; *Lasers Med Sci*; 2008; pp. 361-367; vol. 23.

El-Mohsen, "Distribution of [3H] trans-Resveratrol in Rat Tissues Following Oral Administration"; *British J. Nutrition*; 2006; pp. 62-70; vol. 96.

Fang, "Transdermal Iontophoresis of Sodium Nonivamide Acetate V. Combined Effect of Physical Enhancement Methods"; *Int J Pharm.*; Mar. 20, 2002; pp. 95-105; vol. 235(1-2).

Fiala, "Innate Immunity and Transcription of MGAT-III and Toll-like Receptors in Alzheimer's Disease Patients are Improved by Bisdemethoxycurcumin"; *Proc Natl Acad Sci USA.*; Jul. 31, 2007; pp. 12849-12854; vol. 104(31).

Flynn; "Percutaneous Drug Penetration Choosing Candidates for Transdermal Development"; *Drug Dev. Res.*; 1988; pp. 169-185; vol. 13.

Fogler, "Distribution and Fate of Free and Liposome-Encapsulated [$^3$H]Nor-Muramyl Dipeptide and [$^3$H]Muramyl Tripeptide Phosphatidylethanolamine in Mice"; *The Journal of Immunology*; 1985; pp. 1372-1377; vol. 135(2).

Fotuhi, "Protect Your Brain Against Memory Loss and Alzheimer's Disease" *The Memory Cure*; 2003; pp. 75-128; McGraw-Hill, NY, NY.

Frank, "A Review of Antioxidants and Alzheimer's Disease"; *Ann. Clin. Psychiatry*; Oct.-Dec. 2005; pp. 269-286; vol. 17(4).

Frautschy, "Phenolic Anti-inflammatory Antioxidant Reversal of AB-induced Cognitive Deficits and Neuropathology"; *Neurobiol. Aging*; 2001; pp. 993-1005; vol. 22.

Fukuyama, "Neurotrophic Activity of Honokiol on the Cultures of FetalRrat Cortical Neurons"; *Bioorg Med Chem Lett.*; Apr. 22, 2002; pp. 1163-1166; vol. 12(8).

Fullbeck, "Novel Curcumin- and Emodin-Related Compounds Identified by In Silico 2D-3D Conformer Screening Induce Apoptosis in Tumor Cells"; *BMC Cancer*; 2005; pp. 97; vol. 5.

Geahlen, "Piceatannol (3,4,3',5'-Tetrahydroxy-Trans-Stilbene) Is a Naturally Occurring Protein-Tyrosine Kinase Inhibitor"; *Biochem. Biophys. Res. Comm.*, 1989; pp. 241-245; vol. 165(1).

Gesher, "Resveratrol From Red Grapes—Pedestrian Polyphenol or Useful Anticancer Agent?"; *Planta Med.*; Oct. 2008;pp. 1651-1655; vol. 74(13).

Ghosh, "Brain Parenchymal Metabolism of 5-Iodo-2'-Deoxyuridine and 5'-Ester Prodrugs"; *Pharm Res.*; 1992, pp. 1048-1052; vol. 9(8).

Giroux, "Nasal Drug Deposition—Controlled Particle Dispersion:Applying Vertical Flow to Optimize Nasal Drug Deposition"; *Drug Delivery Technology*; Mar. 2005; pp. 44-49.

Gosslau, "A Methoxy Derivative of Reservatrol Analogue Selectively Induced Activation of the Mitochondrial Apoptotic Pathway in Transformed Fibroblasts"; *Brit. J. Can. Res.*; 2005; pp. 513-521; vol. 92.

Gosslau, "Trans- and Cis-Stilbene Polyphenols Induced Rapid Perinuclear Mitochondrial Clustering and P53-Independent Apoptosis in Cancer Cells But Not Normal Cells"; *Eur J Pharmacol.*; Jun. 10, 2008; pp. 25-34; 587(1-3).

Greenwald, "Drug Delivery Sytems Employing 1,4- or 1,6-Elimination: Poly (ethylene glycol) Prodrugs of Amine-Containing Compounds"; *J. Med. Chem*; 1999; pp. 3657-3667; vol. 42(18).

Guerra, WJZ: Curry-Based Pill May Keep You Healthy .[online], Apr. 13, 2007; Retrieved from the Internet URL: http:--www.mccormickscienceinstitute.com-content.cfm?id=10464.

Gura, "Hope in Alzheimer's Fight Emerges From Unexpected Places"; *Nature Medicine*; 2008; p. 894; vol. 14.

Gynther, "Large Neutral Amino Acid Transporter Enables Brain Drug Delivery via Prodrugs"; *J. Med. Chem.*; 2008; pp. 932-936; vol. 51.

Han, "Neuroprotective Effects of Resveratrol Against B-amylod-induced Neurotoxicity in Rat Hippocampal Neurons: Involvement of Protein Kinase C"; *Br. J. Pharmacology*; 2004; pp. 997-1005; vol. 141.

Han, "Specific Plasma Membrane Binding Sites for Polyphenols; Including Resveratrol; In the Rat Brain"; *J. Pharmacol. Exp. Ther.*; Jul. 2006; pp. 238-245 vol. 318(1); (Epub Mar. 30, 2006).

Hari, "One-Pot Synthesis of 2,3-Disubstituted N-Tosylindoles from o-Acyl-N-tosylanilines"; *Synthesis*; 2006; pp. 1249-1252; No. 8.

Heller, "Poly (Ortho Esters)"; *Handbook of Biodegradable Polymers*; edited by Domb; et al; Hardwood Academic Press; 1997; pp. 99-118.

Hinz, "Percutaneous Penetration of *Para*-Substituted Phenols in Vitro"; *Fundam. Appl. Toxicol.*; 1991; pp. 575-583; vol. 17; The Society of Toxicology.

Hirpara, "Quercetin and Its Derivatives: Synthesis, Pharmacological Uses With Special Emphasis on Anti-Tumor Properties and Prodrug With Enhanced Bio-Availability"; *Anticancer Agents Med. Chem.*, Feb. 2009, pp. 138-161; vol. 9(2).

Holland, The Effects of Cannabinoids on P-glycoprotein Transport and Expression in Multidrug Resistant Sells; *Biochem. Pharmacol.*; 2006; pp. 1146-1154.

Hong, Involvement of Multidrug Resistance-associated Proteins in Regulating Cellular Levels of (−)-epigallocatechin-3-gallate and its Methyl Metabolites; *Biochem. Biophys. Res. Comm.*; Oct. 2003; pp. 222-227; vol. 310(1).

Horvath, "Novel Resveratrol Derivatives Induce Apoptosis and Cause Cell Cycle Arrest in Prostate Cancer Cell Lines"; *Anticancer Res*; 2007; pp. 3459-3464.

Hossain, "Alternative, East and Efficient Preparation of Poly[4-(diacetoxyiodo)styrene] from Poly(4-iodostyrene) Using Sodium Perborate as the Oxidant"; *Synthesis*; 2006; pp. 1253-1256; No. 8.

Howitz, Small Molecule Activators of Sirtuins Extend *Saccaromyces cerevisiae* Lifespan; *Nature*; 2003; pp. 191; vol. 425.

Hur, "Rosmarinic Acid Induces P56$^{lck}$-Dependent Apoptosis in Jurkat and Peripheral T Cells Via Mitochondrial Pathway Independent From Fas-Fas Ligand Interaction"; *J. Immunology*; 2004; pp. 79-87; vol. 172.

Hussain, "Prodrugs for Improved Oral β-Estradiol Bioavailability"; *Pharm. Res.*; 1988; pp. 44-47; vol. 5(1).

Hussain, Testosterone 17B-N;N-dimethylglycinate Hydrochloride: A Prodrug With a Potential for Nasal Delivery of Testosterone; *J. Pharm. Sci.*; Mar. 2002; pp. 785-789; vol. 91(3).

Irie, "Structure of β-amyloid Fibrils and its Relevance to Their Neurotoxicity: Implications for the Pathogenesis of Alzheimer's Disease"; *Journal of Bioscience and Bioengineering*; 2005; pp. 437-447; vol. 99 No. 5.

Ishida, Antitumor Agents; Part 214: Synthesis and Evaluation of Curcumin Analogues as Cytotoxic Agents; *Bioorganic and Medicinal Chemistry*; 2002; pp. 3481-3487; vol. 10.

Jean, Structural Elements Regulating Amyloidogenesis: A Cholinesterase Model System; *PLOS One*; 2008; vol. 3(3); e1834.

Jensen, "Water-soluble Aminoalkylbenzoate Esters of Phenols as Prodrugs: Synthesis; Enzymatic Hydrolysis and Chemical Stability of Paracetamol Esters"; *Acta Pharma Nord*; 1991; pp. 31-40; vol. 3(1).

Jeon, "β-secretase (BACE1)-inhibiting Stilbenoids From Smilax Rhizome"; *Phytomedicine*; 2007; pp. 403-408; vol. 14.

John, "Anti-Tumor Studies of Metal Chelates of Synthetic Curcuminoids"; *J. Exp. Clinic. Cancer Res.*; 2002; pp. 219-224; vol. 21.

Kandimalla, "Transport of Hydroxyzine and Triprolidine Across Bovine Olfactory Mucosa: Role of Passive Diffusion in the Direct Nose-to-brain Uptake of Small Molecules"; *International Journal of Pharmaceutics*; 2005; pp. 133-144; vol. 302.

Kao, "Enhancement of the Systemic and CNS Specific Delivery of I-dopa by the Nasal Administration of its Water Soluble Podrugs"; *Pharmaceutical Research*; pp. 2000; 978-984; vol. 17(8).

Kao, "Evaluation of [$^{76}$Br]FBAU 3',5'-dibenzoate as a Lipophilic Prodrug for Brain Imaging"; *Nuclear Medicine and Biology*; 2007; pp. 527-535; vol. 29.

Kapoor; "Telomerase Targeted Anticancer Bioactive Prodrug by Antisense-based Approach"; *Cancer Letters*; 2007; pp. 245-250; vol. 248.

Kemnitzer, et al., "Degradable Polymers Derived From the Amino Acid L-Tyrosine," in Handbook of Biodegradable Polymers, Domb, et al., eds. (Harwood Academic Press), pp. 251-272 (1997).

Kim, "Butein Sensitizes Human Leukemia Cells to Apoptosis Induced by Tumor Necrosis Factor-Related Apoptosis Inducing Ligand (TRAIL)"; *Arch. Pharm. Res.*; 2008; pp. 1179-1186; vol. 31(9).

Kim, "Curcuminoids From *Curcuma longa* L. (Zingiberaceae) that Protect PC12 Rat Pheochromocytoma and NormalHuman Umbilical Vein Endothelial Cells From βA(1-42) Insult"; *Neuroscience Letters*; 2001; pp. 57-61; vol. 303.

Kim, "Protective Effects of Piceatannol Against Beta-amyloid-induced Neuronal Cell Death"; *Ann. N.Y. Accad. Sci*; 2007; pp. 473-482; vol. 1095.

Kim, "Resveratrol Inhibits Inducible Nitric Oxide Synthase and Cyclooxygenase-2 Expression in β-amyloid-treated C6 Glioma Cells"; *International Journal of Molecular Medicine*; 2006; pp. 1069-1075; vol. 17.

Kleindienst, "Effect of Dimethyl Sulfoxide on Blood-brain Barrier Integrity Following Middle Cerebral Artery Occlusion in the Rat"; *Acta Neurochir*; 2006; pp. 258-262; vol. 96.

Klimowicz, "The Phytochemical Piceatannol Induces the Loss of CBL and CBL-Associated Proteins"; *Mol. Cancer Ther.*, Mar. 2009: pp. 602-614; vol. 8(3).

Kozarsky, "Gene Therapy for Cardiovascular Disease"; *Current Opinion in Pharmacology*; 2001; pp. 197-202; vol. 1.

Kubo, "Nonpeptide Angiotensin II Receptor Antagonists. Synthesis and Biological Activity of Potential Prodrugs of Benzimidazole-7-Carboxylix Acids"; *J. Med. Chem.*; 1993; pp. 2343-2349; vol. 36(16).

Kumar, "Biodegradable Microspheres of Curcumin for Treatment of Inflammation"; *Indian J. Physiol. Pharmacol*; 2002; pp. 209-217; vol. 46(2).

Kumar, "Design and Synthesis of Curcumin-bioconjugates to Improve Delivery"; *Nucleic Acids Symposium Series*; 2000; pp. 75-76; No. 44.

Kumar, "Syntheses of Curcumin Bioconjugates and Study of Their Antibacterial Activities Against β-Lactamase-Producing Microorganisms"; *Bioconjug Chem.*; 2001; pp. 464-469; vol. 12(4).

Kurkela, "Expression and Characterization of Recombinant Human UDP-glucuronosyltransferases (UGTs)"; *The Journal of Biological Chemistry*; 2003; pp. 3536-3544; vol. 278(6).

Lai, "Antitumor Effect of Methylene Blue In Vivo"; *Zhonghua Zhong Liu Za Zhi.*; Mar. 1989; pp. 98-100; vol. 11(2).

Lamba, "Imine-bridged Planar Poly(p-phenylene) Derivatives for Maximization of Extended π-conjugation. The Common Intermediate Approach"; *J. Am. Chem.*; 1994; pp. 11723-11736; vol. 116.

Laneri, "Ionized Prodrugs of Dehydroepiandrosterone for Transdermal Iontophoretic Delivery"; *Pharmaceutical Research*; 1999; pp. 1818-1824; vol. 16(12).

Larrosa, "The Grape and Wine Polyphenol Piceatannol Is a Potent Inducer of Apoptosis in Human SK-Mel-28 Melanoma Cells"; *Eur. J. Nutr.*, Oct. 2004; pp. 275-284; vol. 43(5).

Lee, "Methylene Blue Induces Cytoxicity in Human Brain Tumor Cells"; *Cancer Letters*; 1995; pp. 141-145; vol. 88(2).

Lee,"A Hybrid Molecule That Prohibits Amyloid Fibrils and Alleviates Neuronal Toxicity Induced by Beta-Amyloid (1-42)"; *Biochem. Biophys. Res. Commun.*; Mar. 25, 2005; pp. 816-823; vol. 328(4).

Lendel, "On the Mechanism of Nonspecific Inhibitors of Protein Aggregation: Dissecting the Interactions of α-Synuclein With Congo Red and Lacmoid"; *Biochemistry*; 2009; pp. 8322-8334.

Li, "2,3',4,4',5'-Pentamethoxy-trans-stilbene, A Resveratrol Derivative, Is a Potent Inducer of Apoptosis in Colon Cancer Cells Via Targeting Microtubules"; *Biochemical Pharmacology*; 2009; pp. 1224-1232; vol. 78.

Lim, "The Curry Spice Curcumin Reducted Oxidative Damage and Amyloid Pathology in an Alzheimer Transgenic Mouse"; *The Journal of Neuroscience*; 2001; pp. 8370-8377; vol. 21(21).

Limtrakul, "Modulation of human multidrug-resistance MDR-1 gene by natural curcuminoids."; *BMC Cancer.*; Apr. 2004; pp. 1-6; vol. 4(13).

Liu, "Design, Synthesis and Primary Evaluation on Curcumin Derivative Prodrugs of Antitumor"; *Zhongguo Yaoshi*, 2005; pp. 543-545.

Liu, "Curcumin Potently Blocks Kv1.4 Potassium Channels"; *Biochem Biophys. Res. Commun.*, Jun. 2006; pp. 1-9; vol. 344(4).

Liu, "Intranasal Administration of the Antioxidant Myricetin Reduces Infarct Volume and Improves Neurologic Function Following Focal Cerebral Ischemia in Rats"; *Neural.*; 2002; p. A389; vol. 58(Suppl.3).

Liu, "Stimulation of Serotonin Synthesis in Rat Brain After Antiepilepsirine; An Entiepileptic Piperine Derivative"; *Biochemical Pharmacology*; 1984; pp. 3883-3886; vol. 33(23).

Loa, "Studies of Structure-Activity Relationship on Plant Polyphenol-Induced Suppression of Human Liver Cancer Cells"; *Cancer. Chemother. Pharmacol.*; May 2009; pp. 1007-1016; vol. 63(6); Epub Sep. 3, 2008.

Lonsky, "Synthesis and Reactions of Hydroxylated Stilbenes and Their Possible Occurrence as Chromophore Precurson Structures in Lignin"; *Monatshefte für Chemie*; 1976; pp. 685-695; vol. 107.

Lu, "Preparation of Curcumin Prodrugs and Their in Vitro Anti-Tumor Activities"; *J Huazhong Univ Sci Technolog Med Sci.*; 2005; pp. 668-670, 678; vol. 25(6).

Lu, "Resveratrol analog, 3,4,5,4'-tetrahydroxystilbene, differentially induces pro-apoptotic p53-Bax gene expression and inhibits the grown of transformed cells but not their normal counterparts"; *Carcinogenesis*; 2001; pp. 321-328; vol. 22(2).

Maher, A Comparison of the Neurotrophic Activities of the Flavenoid Fisetin and Some of its Derivatives; *Free Radical Research*; 2006; pp. 1105-1111; vol. 40(10).

Majumdar, "Curcumin Synergies With Resveratrol to Inhibit Colon Cancer"; *Nutrition and Cancer*; Jul. 2009; pp. 544-553; vol. 61(4).

Mancuso, "Natural antioxidants in Alzheimer's disease"; *Expert Opinion on Investigational Drugs*; 2007; pp. 1921-1931; vol. 16; No. 12.

Mandelkow, "Structural Principles of Tau and the Paired Helical Filaments of Alzheimer's Disease"; *Brain Pathol.*; 2007; pp. 83-90; vol. 17.

Mano, "In Vitro Inhibitory Effects of Non-Steroidal Anti-Inflammatory Drugs on 4-Methylumbelliferone Glucuronidation in Recombinant Human UDP-glucuronosyltransferase 1A9—Potent Inhibition by Nifulmic Acid"; *Biopharm. Drug Dispos.*; 2006; pp. 1-6; vol. 27.

Marambaud, "Reservatrol Promotes Clearance of Alzheimer's Disease Amyloid-β Peptides"; *J. Biol. Chem.*; 2005; pp. 37377-37382; vol. 280(45).

K Ů dela, "Hydrogels"; *Concise Encyclopedia of Polymer Science and Engineering*; 1990; pp. 458-459; Wiley and Sons.

Mazumder, "Curcumin Analogs with Altered Potencies Against HIV-1 Integrase as Probes for Biochemical Mechanisms of Drug Action"; *J. Med. Chem*; 1997; pp. 3057-3063; vol. 40.

Mickstacka, "Effect of Natural Analogues of Trans-Resveratrol on Cytochromes P4501A2 and 2E1 Catalytic Activities"; *Xenobiotica*; 2006; pp. 269-285.

Mishra, "Design, Development and Synthesis of Mixed Bioconjugates of Piperic Acid-Glycine; Curcumin-Glycine-Alanine and Curcumin-Glycine-Piperic Acid and their Antibacterial and Antifungal Properties"; *Bioorganic & Medicinal Chemistry*; 2005; pp. 1477-1486; vol. 13.

Mishra, "Differential Apoptotic and Redox Regulatory Activities of Curcumin and its Derivatives"; *Free Rad. Biology & Medicine*; 2005; pp. 1353-1360; vol. 38.

Mulholland, "Pre-Clinical and Clinical Study of QC12; a Water-Soluble; Pro-Drug of Quercetin"; *Annals Oncology*; 2001; pp. 245-248; vol. 12.

Muller, "The Determination of the Amphiphilic Properties of a Prodrug (DDMS) of Phenytoin in Aqueous Media"; *International Journal of Pharmaceutics*; 1992; pp. 175-186; vol. 86(2-3).

Murakami, "Distance Measurement Between Tyr10 and Met35 in Amyloid β by Site-Directed Spin-Labeling ESR Spectroscopy: Implications for the Stronger Neurotoxicity of Aβ42 than Aβ40"; *ChemBioChem*; 2007; pp. 2308-2314; vol. 8.

Murtha, "Synthesis of the Cholesteryl Ester Prodrugs Cholesteryl Ibuprofen and Cholesteryl Flufenamate and Their Formulation Into Phospholipid Microemulsions"; *Journal of Pharmaceutical Science*; 1994; pp. 1222-1228; vol. 83(9).

Murthy, "Iontophoretic Drug Delivery Across Human Nail"; *J Pharm Sci.*; 2007; pp. 305-311; vol. 96(2).

Naganuma, "Turmeric and Curcumin Modulate the Conjugation of 1-Naphthol in Caco-2 Cells"; *Biol. Pharm. Bull.*; 2006; pp. 1476-1479; vol. 29(7).

Nakaya, "Plastic Scintillators. II. The Synthesis of Some Distyrylbenzene Derivatives as Wavelength Shifters in Plastic Scintillators"; *Bulletin of the Chemical Society of Japan*; 1966; pp. 1547-1551; vol. 39.

Narayanan, "Liposome Encapsulation of Curcumin and Resveratrol in Combination Reduces Prostate Cancer Incidence in PTEN Knockout Mice"; *Int. J. Cancer*; 2009; pp. 1-8; vol. 125(1).

Narlawar, "Curcumin Derivatives Inhibit or Modulate Beta-Amyloid Precursor Protein Metabolism"; *Neurodegen. Dis.*; 2007; pp. 88-93; vol. 4.

Narlawar, "Curcumin-Derived Pyrazoles and Isoxazoles: Swiss Army Knives or Blunt Tools for Alzheimer's Disease?"; *ChemMedChem Papers*; 2007; pp. 1-9.

Neuhouser, "Dietary Flavonoids and Cancer Risk: Evidence From Human Population Studies"; *Nutr. Cancer*, 2004; pp. 1-7; vol. 50(1).

Nielsen, "Bioreversible Quaternary N-Acyloxymethyl Derivatives of the Tertiary Amines Bupivacaine and Lidocaine-Synthesis; Aqueous Solubulity and Stability in Buffer; Human Plasma and Simulated Intestinal Fluid"; *Eur.J.Pharm.Sci.*; 2005; pp. 433-440; vol. 24(5).

Nielsen, "Bioreversible Quaternary N-acyloxymethyl Derivatives of the Poorly Soluble Tertiary Amine Lu 28-179—Synthesis, Pharmaceutical Chemical Characterization and Bioavailability Studies in Dogs"; *European Journal of Pharmaceutical Sciences*; 2005; pp. 421-428; vol. 26.

Noller, "Photochemie Elektronenreicher 1,3-Distyrylbenzole"; *Chem Ber.*; 1988; pp. 1609-1615; vol. 121.

Nugroho, "Transdermal Iontophoresis of the Dopamine Agonist 5-OH-DPAT in Human Skin In Vitro"; *J. Controlled Release*; 2005; pp. 393-403; vol. 103.

Oetari, "Effects of Curcumin on Cytochrome P450 and Glutathione S-Transferase Activities in Rat Liver"; *Biochem. Pharmacol.*; 1996; p. 39-45; vol. 51(1).

Okamoto; "Effect of Ionic Strength on Solution Stability of PNU-67590A, A Micellar Prodrug of Methylprednisone"; *Pharmaceutical Research*; 1997; vol. 14(9).

Ono, "Anti-Parkinsonian Agents Have Anti-Amyloidogenic Activity for Alzheimer's β-Amyloid Fibrils in vitro"; *Neurochem. Int..*; 2006 pp. 275-285.

Pal, "Non-hydrogen Bond Interactions Involving the Methionine Sulfur Atom"; *Journal of Biomolecular Structure & Dynamics*; 2001; pp. 115-128; vol. 19(1).

Pan, "Biotransformation of Curcmin Through Reduction and Glucuronidation in Mice"; *Drug Metabolism and Disposition*; 1999; pp. 486-494; vol. 27(1).

Paradkar, "Characterization of Curcumin-PVP Solid Dispersion Obtained by Spray Drying"; *International Journal of Pharmaceutics*; 2004; pp. 281-286; vol. 271.

Parang, "Synthesis, In Vitro Anti-Human Immunodeficiency Virus Structure-Activity Relationships and Biological Stability of '5-O-Myristoyl Analogue Derivatives of 3'-Azido-2',3'-Dideoxythymidine (AZT) As Potential Prodrugs"; *Antivir Chem Chemother*; 1998; pp. 311-323; vol. 9(4).

Park, "Design and Synthesis of Small Chemical Inhibitors Containing Different Scaffolds for Lck SH2 Domain"; *Bioorg Med Chem Lett.*; 2003; pp. 3455-3459; vol. 13(20).

Park, "Discovery of Natural Products from Curcuma longa that Protect Cells from beta-amyloid Insult: A Drug Discovery Effort Against Alzheimer's Disease"; *Journal of Natural Products*; 2002; pp. 1227-1231; vol. 65(9).

Pinho, "The role of N-acetylglucosaminyltransferase III and V in the post-transcriptional modifications of E-cadherin"; *Hum Mol Genet.*; 2009; pp. 2599-2608; vol. 18(14); Epub Apr. 29, 2009.

Pop, "Derivatives of Dexanabinol. I. Water-Soluble Salts of Glycinate Esters"; *Pharmaceutical Research*; pp. 62-69; vol. 13(1), 1996.

Pop, "Derivatives of Dexanabinol. II. Salts of Amino Acid Esters Containing Tertiary and Quaternary Heterocyclic Noitrogen with Increased Water-Solubility"; *Pharmaceutical Research*; 1996; pp. 469-475; vol. 13(3).

Pop, "In Vitro and in Vivo Study of Water-Soluble Prodrugs of Dexanabinol"; *Journal of Pharmaceutical Sciences*; 1999; pp. 1156-1160; vol. 88(11).

Purkayastha, "Curcumin Blocks Brain Tumor Formation"; *Brain Research*; 2009; pp. 130-138; 1266.

Qasem, "Kinetics of Paclitaxel 2'-N-Methylpyridinium Mesylate Decomposition"; *AAPS PharmSciTech*; 2003; vol. 4(2).

Qin, "Neuronal SIRT1 Activation as a Novel Mechanism Underlying the Prevention of Alzheimer Disease Amyloid Neuropathology by Calorie Restriction"; *Journal of Biological Chemistry*; 2006; pp. 21745-21754; vol. 281(31).

Rajakumar, "Synthesis of New Photoresponsive Stilbene Dendrons and Dendrimers"; *Synthesis*; 2006; pp. 1257-1262; No. 8.

Ramsewak, "Cytotoxicity, Antioxidant and Anti-Inflammatory Activities of Curcumins I-III From *Curcuma longa*"; *Phytomedicine*; 2000; pp. 303-308; vol. 7(4).

Reen, "Impairment of UDP-Glucose Deydrogenase and Glucuronidation Activities in Liver and Small Intestine of Rat and Guinea Pig in Vitro by Piperine"; *Biochemical Pharmacology*; 1993; pp. 229-238; vol. 46(2).

Reinke, "Structure-activity Relationships of Amyloid Beta-aggregation Inhibitors Based on Curcumin: Influence of Linker Length and Flexibility"; *Chem Biol Drug Des*; 2007; pp. 206-215; vol. 70.

Riviere, "New Polyphenols Active on β-amyloid Aggregation"; *Bioorganic & Medicinal Chemistry Letters*; 2008; pp. 828-831; 18.
Roh; "Sinonasal Distribution of Nasal Drops and Spray According to Head Positions"; *Journal of Korean Otolaryngal Head Neck Surgery*; 2004; pp. 736-740; vol. 47(8) (English abstract only).
Romiti, "Effects of Curcumin of P-Glycoprotein in Primary Cultures of Rat Hepatocytes"; *Life Sciences*; 1998; pp. 2349-2358; vol. 62(25).
Roughley, "Experiments in the Biosynthesis of Curcumin"; *J. Chem. Soc. Perkin Trans. 1*; 1973; pp. 2379-2388.
Ruan, "Improving the Solubility of Ampelopsin by Solid Dispersions and Inclusion Complexes"; *J. Pharm Biomed. Anal*; 2005; pp. 457-464;vol. 38(3).
Rubin; "Recent Advances in Cyclopropene Chemistry"; *Synthesis*; 2006; pp. 1221-1245; No. 8.
Safavy, "Design and Development of Water-Soluble Curcumin Conjugates as Potential Anticancer Agents"; *J Med Chem*; 2007; pp. 6284-6288.
Sahelian, "Prostaglandin"; 2006; 5 pages, http:--web.archive-org-web-200608015095912-http:www.raysahelian.com-prostaglandin.html.
Savaskan, "Red Wine Ingredient Reservatrol Protects from β-Amyloid Neurotoxicity"; *Gerontology*; Nov. 2003; pp. 380-383; vol. 49.
Scheld, "Drug Delivery to the Central Nervous System: General Principles and Relevance to Therapy for Infections of the Central Nervous System"; *Rev. Infect. Dis.*; 1989; pp. S1669-S1690; vol. 11(7).
Selvam, "Design, Synthesis, Biological Evaluation and Molecular Docking of Curcumin Analogues as Antioxidant, Cyclooxygenase Inhibitory and Anti-inflammatory Agents"; *Bioorg. & Medic. Chem. Letters* ; 2005; pp. 1793-1797; 15.
Seow, "Piceatannol, A Syk-Selective Tyrosine Kinase Inhibitor, Attenuated Antigen Challenge of Guinea Pig Airways In Vitro"; *Eur.J. Pharm.*, 2002; 189-196.
Shamsi, "Glycine-based Polymeric Surfactants with Varied Polar Head Group:II. Chemical Selectivity in Micellar electrokinetic Chromatography Using Linear Salvation Energy Relationships"; *Electrophoresis*; 2005; pp. 4138-4152; vol. 26.
Sharma, "Phase I Clinical Trial of Oral Curcumin: Biomarkers of Systemic Activity and Compliance"; *Clin. Cancer Res.*; 2004; pp. 6847-6854; 10.
Shen, "Curcumin Surfactant as Anticancer Prodrugs and Drug Carriers"; 2009; *AIChE*;.
Shoba, "Influence of Piperine on the Pharmacokinetics of Curcumin in Animals and Human Volunteers"; *Planta Med.*; 1998; pp. 353-356.
Silva, "Potential Tuberculostatic Agents: Micelle-Forming Copolymer Poly(ethylene glycol)-Poly(aspartic acid) Prodrug with Isoniazid"; *Arch Pharm. Pharm. Med. Chem.*; 2001; pp. 189-192.
Simoni, "Stilbene-Based Anticancer Agents: Resveratrol Analogues Active Toward HL60 Leukemic Cells With a Non-Specific Phase Mechanism"; *Bioorg Med Chem Lett.*; 2006; pp. 3245-3248; vol. 16(12).
Stites; "Protein-Protein Interactions: Interface Structure; Binding Thermodynamics; and Mutational Analysis"; *Chem. Rev.*; 1997; pp. 1233-1250; vol. 97.
Takata, "Novel d-γ-tocopherol derivative as a prodrug for d-γ-tocopherol and a two-step Prodrug for S-γ-CEHC"; *J. Lipid Res.*; 2002; pp. 2196-2204; vol. 43.
Takata, "Vitamin K Prodrugs: 1. Synthesis of Amino Acid Esters of Menahydroquinone-4 and Enzymatuc Reconversion to an Active Form"; *Pharm. Res.*; 1995; pp. 18-23; vol. 12(1).
Takatsuka, "Synergistic Absorption Enhancement of Salmon Calcitonin and Reversible Mucosal Injury by Applying a Mucolytic Agent and a Non-ionic Surfactant"; *Int. J. Pharm.*; 2006; pp. 124-130; vol. 316;.
Taniguchi, "Inhabitation of Heparin-induced Tau Filament Formation by Phenothiazines, Polyphenols, and Porphyrins"; *J. Biol. Chem.*; 2005; pp. 7614-7623; vol. 280(9).
Tatko, "Investigation of the Nature of the Methionine-π interaction in β-hairpin Ppeptide Model Systems"; *Protein Science*; 2004; pp. 2515-2522; vol. 13.

Thapliyal, "Inhibition of Cytochrome P450 Isozymes by Curcumins In Vitro and In Vivo"; *Food Chem. Toxicol.*; 2001; pp. 541-547; vol. 39.
Tong, "Apoptosis-inducing Effects of Curcumin Derivatives in Human Bladder Cancer Cells"; *Anti-Cancer Drugs*; 2006; pp. 279-287; vol. 17.
Tønnesen, "Solubility, Chemical and Photochemical Stability of Curcumin in Surfactant Solutions. Studies of Curcumin and Curcuminoids, XXVIII"; *Pharmazie*; 2002; pp. 820-824; vol. 57(12).
Trapani, "Water-soluble Salts of Aminoacid Esters of the Anaesthetic Agent Propofol"; *Intl. J. Pharm.*; 1998; pp. 195-204; vol. 175.
Uchino, "Transport of Amino Acid-Related Compounds Mediatied by L-Type Amino Acid Transporter 1 (LAT1): Insights Into the Mechanisms of Substrate Recognition"; *Molecular Pharmacology*; 2002; pp. 729-737; vol. 6(4).
Valiveti, "Intranasal Absorbtion of $\Delta^9$-Tetrahydrocannabinol and EIN55,212-2 Mesylate in Rats"; *European Journal of Pharmaceutics and Biopharmaceutics*; 2007; pp. 247-252; vol. 65.
Van Der Logt, "Induction of Rat Hepatic and Intestinal UDP-Glucuronosyltransferases by Naturally Occurring Dietary Anticarcinogens"; *Carcinogenesis*; 2003; pp. 1651-1656; vol. 24(10).
Vandorpe, "Biodegradable Polyphosphazenes for Biomedical Applications." In Handbook of Biodegradable Polymers, Domb, et al., eds. (Harwood Academic Press), pp. 161-182 (1997).
Vareed, "Pharmacokinetics of Curcumin Conjugate Metabolites in Healthy Human Subjects"; *Cancer Epidemiol Biomarkers Prev.* ; 2008; pp. 1411-1417; vol. 17.
Vitaglione, "Bioavailability of *Trans*-reservatrol From Red Wine in Humans"; *Mol. Nutr. Food Res.*; 2005; pp. 495-504; vol. 49; Wiley.
Volak, "Curcuminoids Inhibit Multiple Human Cytochromes P450, UDP-Glucuronosyltransferase, and Sulfotransferase Enzymes, Whereas Piperine Is a Relatively Selective CYP3A4 Inhibitor"; *Drug Metabolism and Disposition*;2008; pp. 1594-1605; vol. 36(8).
Walsh, "Certain Inhibitors of Synthetic Amyloid Beta-Peptide (Abeta) Fibrillogenesis Block Oligomerization of Natural Abeta and Thereby Rescue Long-Term Potentiation"; *J. Neuroscience*; 2005; pp. 2455-2462; vol. 25(10).
Wang, "Resveratrol Protects Against Global Cerebral Ischemic Injury in Gerbils"; *Brain Research*; 2002; pp. 439-447; vol. 958.
Wang, "Trial of Antiepilepsirine (AES) in Children with Epilepsy; *Brain & Development*"; 1999; pp. 36-40; vol. 21.
Wang, "Nipecotic Acid: Systemic Availability and Brain Delivery After Nasal Administration of Nipecotic Acid and π-Butyl Nipecotate to Rats," *Pharmaceutical Research*, 22(4): 556-562 (2005).
Wenzel, "Metabolism and Bioavailability of Trans- Resveratrol"; *Mol. Nutr. Food Res.*; 2005; pp. 472-481; vol. 49.
Wieder, "Piceatannol, A Hydroxylated Analog of the Chemopreventive Agent Resveratrol, Is a Potent Inducer of Apoptosis in the Lymphoma Cell Line BJAB and in Primary, Leukemic Lymphoblasts"; *Leukemia*; Nov. 2001; pp. 1735-1742; vol. 15(11).
Wischik, "Selective Inhibition of Alzheimer Disease-like Tau Aggregation by Phenothiazines"; *Proc. Natl. Acad. Sci.*; 1996; pp. 11213-11218; vol. 93.
Wong, "Glucuronidation of 3-0 Methylnoradrenaline;Harmalol and some Related Compounds"; *Biochem J*; 1968; pp. 99-104; vol. 110.
Wortelboer, "Interplay Between MRP Inhibition and Metabolism of MRP Inhibitors: The Case of Curcumin"; *Chem. Res. Toxicol.* ; 2003; pp. 1642-1651; vol. 16.
Yang "Curcumin Inhibits Formation of Amyloid β Oligomers and Fibrils, Binds Plaques, and Reduces Amyloid in Vivo"; *J. Biol. Chem*; 2005; pp. 5892-5901; vol. 280(7).
Yang, "Design and Synthesis of Compounds That Extend Yeast Replicative Lifespan"; *Aging Cell*; 2007; pp. 35-43; vol. 6.
Yarovenko, "A Convenient Synthesis of N-Substituted 2-Thioxo-1, 3-thiazolidin-4-ones"; *Synthesis*; 2006; pp. 1246-1248; No. 8.
Yodkeeree, "Curcumin, Demethoxycurcumin and Bisdemethoxycurcumin Differentially Inhibit Cancer Cell Invasion Through the Down-Regulation of MMPs and uPA"; *J. Nutr. Bio.*; 2009; pp. 87-95; vol. 20(2).

Zatta, "Deposition of Aluminum in brain tissues of rats exposed to inhalation of aluminum acetylacetonate"; *Neuroreport*; pp. 1119-1122; vol. 4(9), 1993.

Zauhar, "Evidence for a Strong Sulfur-Aromatic Interaction Derived From Crystallographic Data"; *Biopolymers*; 2000; pp. 233-248; vol. 53.

Zhou, "Herbal Modulation of P-Glycoprotein"; *Drug Metab. Rev.*; Feb. 2004; pp. 57-104; vol. 36(1).

Ziora, "Small-sized BACE1 Inhibitors"; *Drugs of the Future*; 2006; pp. 53-63; vol. 31(1).

International Search Report in PCT Application No. PCT/US2008/060569, 2 pages, mailed Jul. 14, 2008.

International Preliminary Report on Patentability and Written Opinion of the International Searching Authority in International Application No. PCT/US2008/060569, 7 pages, date of issuance of report Dec. 7, 2009.

Non-Final Office Action for U.S. Appl. No. 11/534,384; Notification Date: Dec. 1, 2010.

Non-Final Office Action for U.S. Appl. No. 12/696,588 dated Sep. 21, 2011.

Charlton, "Distribution and clearance of bioadhesive formulations from the olfactory region in man: Effect of polymer type and nasal delivery device" European Journal of Pharmaceutical Sciences; 2007; pp. 295-302; vol. 30.

Exhibit A—Dictionary.com, Anterior, Last Accessed Mar. 5, 2011,4 pages, http://dictionary.reference.com/browse/anterior.

Exhibit B—Newman et al., Deposition pattern of nasal sprays in man, 1987, Whinology, 26, pp. 111-120 and citation page (11 pages in all).

Final Office Action mailed Apr. 15, 2010 in pending U.S. Appl. No. 12/147,881.

Final Office Action mailed Aug. 9, 2010 in pending U.S. Appl. No. 11/534,384.

Final Office Action mailed Dec. 24, 2009 in pending U.S. Appl. No. 11/534,384.

Final Office Action mailed Dec. 3, 2009 in pending U.S. Appl. No. 11/736,278.

Final Office Action mailed Dec. 9, 2010 in pending U.S. Appl. No. 11/736,278.

Final Office Action mailed Jul. 14, 2010 in pending U.S. Appl. No. 11/736,278.

Final Office Action mailed Jun. 1, 2010 in Pending U.S. Appl. No. 12/029,904.

Final Office Action mailed May 5, 2011, in Pending U.S. Appl. No. 12/029,904.

Final Office Action mailed May 9, 2011 in pending U.S. Appl. No. 11/534,384.

Flonase, Get the Best Results with proper usage,Oct. 27, 2003, http://www.flonase.com/use/howto.html, last accessed Sep. 13, 2010, pp. 1-4.

International Search Report and Written Opinion dated Feb. 3, 2010 for PCT/US09/67275.

International Search Report dated Apr. 20, 2010 for PCT/US10/21968.

International Search Report dated Aug. 27, 2009 PCT/US09/48466.

International Search Report dated Jul. 14, 2008 PCT /US08/60569.

Kissinger, "Crystal Structure of Human ABAD/HSD10 with a Bound Inhibitor: Implications for Design of Alzheimer's Disease Therapeutics"; J. Mol. Biol.; 2004; pp. 943-952; vol. 342; Elsevier.

Klunk, "Imaging Aβ Plaques in Living Transgenic Mice with Multiphoton Microscopy and Methoxy-X04, a Systemically Administered Congo Red Derivative"; *J. Neuropathol. Exp. Neurol.*, vol. 61, No. 9, pp. 797-805 (Sep. 2002).

Kublik, et al, "Nasal delivery systems and their effect on deposition and absorption", 1998, Advanced Drug Delivery Reviews, 29, pp. 157-177.

Kumar, S. et al., "Study on Curcumin-Oligonucleotide Conjugate as a Probable Anticancer Agent: Its Hybridisation With Telomere Target Sequence 5'-GGGATTGGGATT-3'", *Nucleic Acids Research Supplement* No. 1:137-138 (2001).

Manju, "Synthesis and Characterization of Cytotoxic Cationic Polyvinylpyrrolidone-Curcumin Conjugate," *J Pharmaceutical Sciences*, pp. 1-8 (2010).

Mark, "Hydrogels"; *Concise Encyclopedia of Polymer Science and Engineering*; 1990; pp. 458-459; Wiley and Sons.

Mishra, et al., "Synthesis of a novel anticancer progrug designed to target telomerase sequence", 2002, Nucleic Acids Research Supplement, No. 2, pp. 277-278.

Mishra, S. et al., "Design, Synthesis and Characterisation of a Novel Anticancer Prodrug Having Antiproliferative Activity Against Prostrate Tumour", *Indian Journal of Chemistry* 44B:2582-2588 (2005).

Non-final Office Action mailed Dec. 1, 2010 in pending U.S. Appl. No. 11/534,384.

Office Action mailed Apr. 7, 2010 in pending U.S. Appl. No. 11/534,384.

Non-Final Office Action mailed Sep. 2, 2011 in pending U.S. Appl. No. 12/029,904.

Office Action mailed Dec. 17, 2009 in Pending U.S. Appl. No. 12/029,904.

Office Action mailed Jun. 10, 2009 in pending U.S. Appl. No. 11/534,384.

Office Action mailed Mar. 22, 2010 in pending U.S. Appl. No. 11/736,278.

Office Action mailed May 11, 2011 in pending U.S. Appl. No. 11/736,278.

Office Action mailed Sep. 17, 2009 in pending U.S. Appl. No. 11/736,278.

Office Action mailed Sep. 27, 2010 in Pending U.S. Appl. No. 12/029,904.

Ono, K., et al., "Alpha-synuclein assembly as a therapeutic target of Parkinson's disease and related disorders", *Curr. Pharm Des.*, 14(30): 3247-3266 (2008).

Parvathy, "Curcumin-amino acid conjugates: synthesis, antioxidant and antimutagenic attributes," *Food Chemistry*, 120: 523-530 (2010).

Pedersen, "Thermal Assembly of a Biomimetic Meral/Collagen Composite"; 2003; pp. 4881-4890; vol. 24.

Pending Non-Published U.S. Appl. No. 13/172,810, filed Jan. 29, 2010 entitled "Iontophoretic Delivery of Curcumin and Curcumin Analogs for the Treatment of Alzheimers Disease".

Spivak, "Spectrophotometric Determination of the Critical Micellar Concentration of Bile Salts Using Bilirubin Monoglucuronide As a Micellar Probe," *Biochem, J.*, 252:275-281 (1988).

Sui, "Inhibition of the HIV-1 and HIV-2 Proteases by Curcumin and Curcumin Boron Complexes"; Biorganic and Medicinal Chemistry; 1993; pp. 415-422; vol. 1; No. 6; Pergamor Press Ltd.; Great Britan.

Tang, "Amphiphilic Curcumin Conjugate-forming Nanoparticles as Anticancer Prodrug and Drug Carriers: in vitro and in vivo Effects", Nanomedicine, vol. 5(6), pp. 855-865 (2010).

Trimaille, "Novel Polymeric Micelles for Hydrophobic Drug Delivery Based on Biodegradable Poly(hexyl-substituted lactides)," *International Journal of Pharmaceuticals*, 319:147-154 (2006).

Tyle, "Iontophoretic Devices for Drug Delivery"; Pharmaceutical Research; 1986; pp. 318-326; vol. 3(6).

Wu, "Material and Synthesis. Synthesis of Lipd-Tail Phosphoramidite. Synthesis Compound," www.pnas.org/cgi/doi/10.1073/pnas.0909611107, 2010.

Zhang, Laura et al., "Curcuminoids enhance amyloid-beta uptake by macrophages of Alzheimer's disease patients," Journal of Alzheimer's Disease, vol. 10, No. 1, pp. 1-7, IOS Press, Amersterdam, NL (Sep. 1, 2006), XP008091733.

Non-Final Office Action mailed Sep. 1, 2011 in pending U.S. Appl. No. 11/534,384.

Berg, J.K., "Can Alzheimers be Prevented or Delayed?", Aug. 29, 2010, 1 page.

WebMD-http:/www.webmd.com/alzheimers-disease-prevention, "Alzheimer's Prevention? Mental Activities, Exercise, Diet, and More", last updated: Nov. 9, 2010, 2 pages.

Non-Final Office Action dated Mar. 27, 2012 for U.S. Appl. No. 12/956,306.

Non-Final Office Action dated Oct. 14, 2011 for U.S. Appl. No. 12/956,306.

Final Office Action dated Feb. 8, 2012 for U.S. Appl. No. 12/696,588.

Non-Final Office Action dated Dec. 14, 2009 for U.S. Appl. No. 12/147,881.

Non-Final Office Action dated Aug. 25, 2009 for U.S. Appl. No. 12/147,881.

Non-Final Office Action dated Sep. 2, 2009 for U.S. Appl. No. 12/343,750.

Notice of Allowance dated Jul. 31, 2012 for U.S. Appl. No. 12/956,306.

\* cited by examiner

FIG. 1A
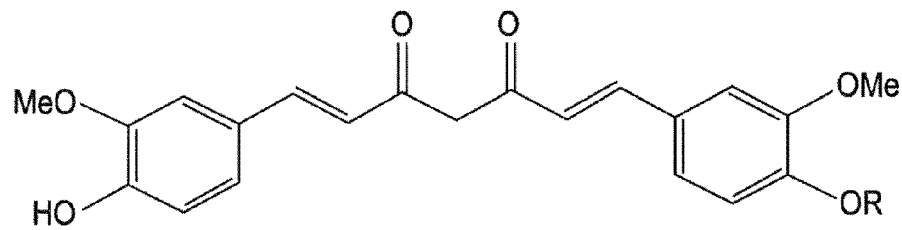
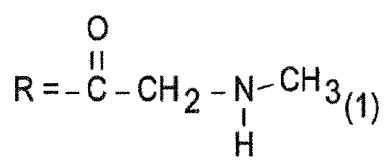  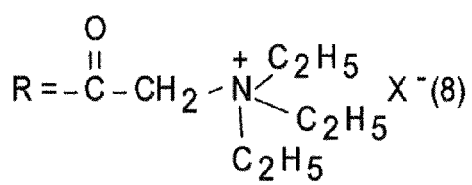
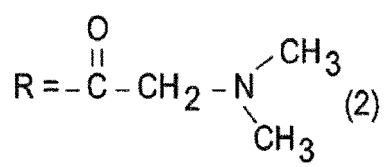  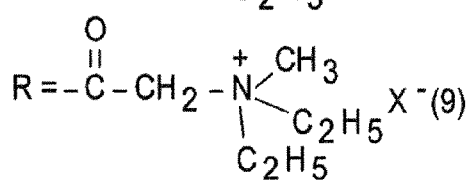
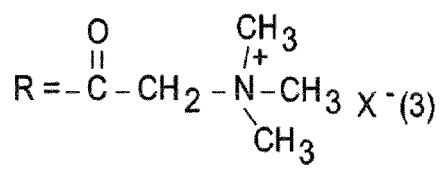  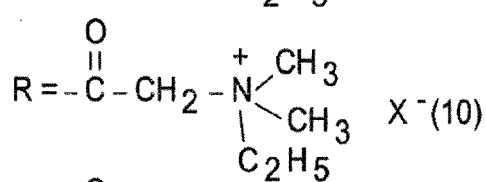
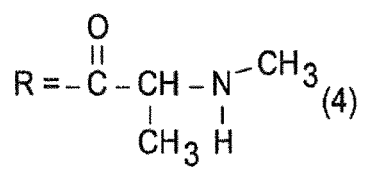  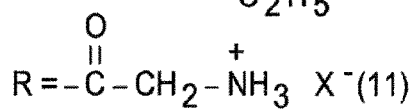
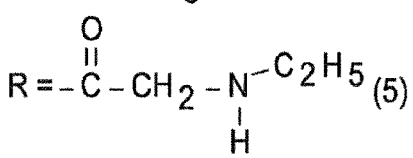  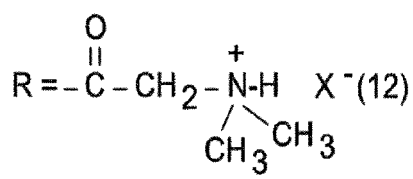
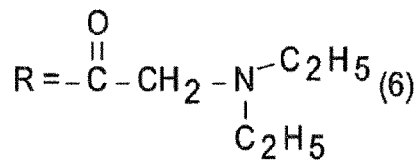  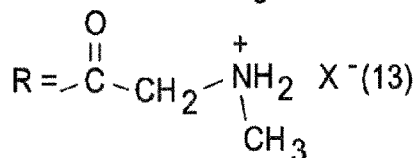
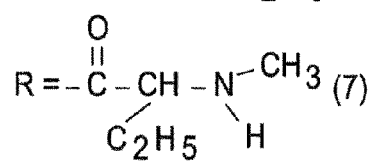  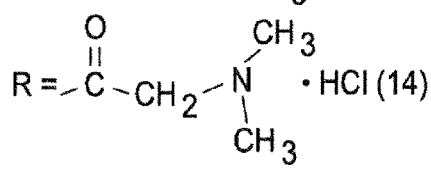

FIG. 1B
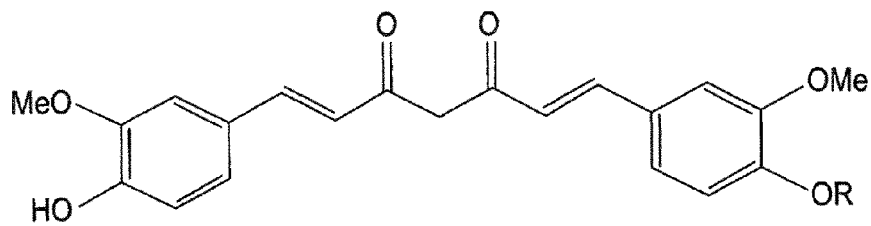
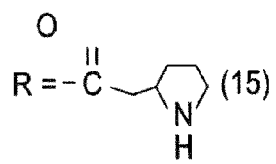  (15)
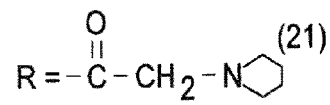  (21)
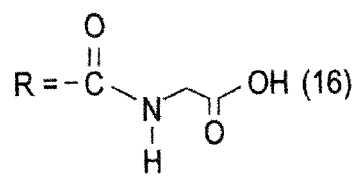  (16)
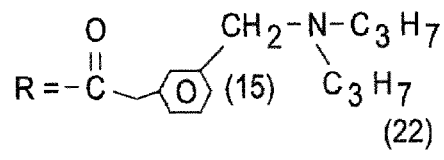  (22)
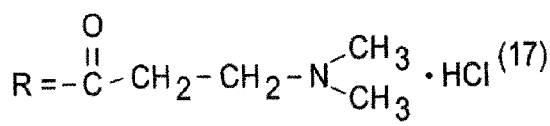  (17)
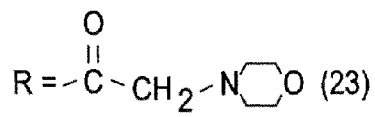  (23)
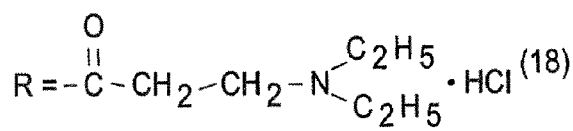  (18)
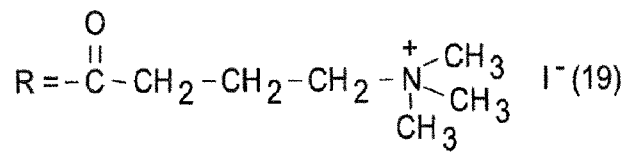  (19)
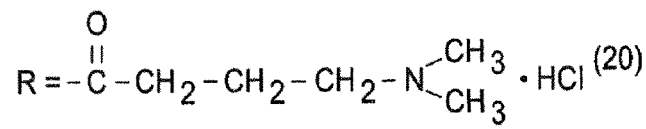  (20)

FIG. 1C
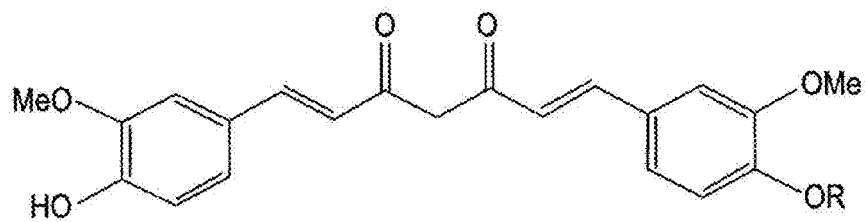
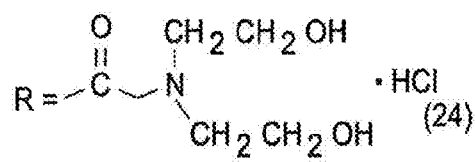
(24)
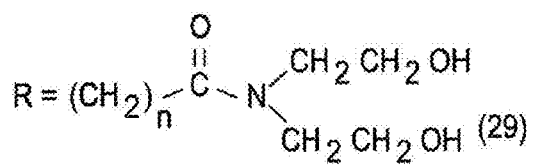
(29)
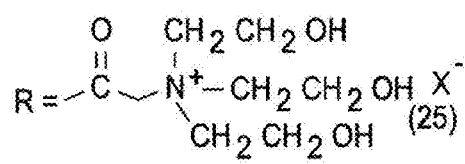
(25)
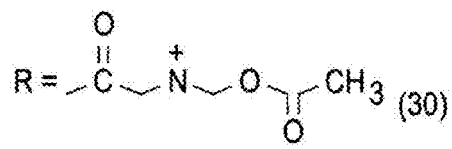
(30)
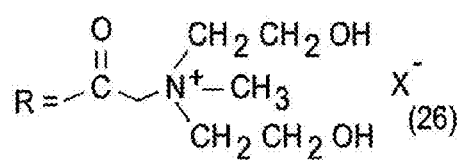
(26)
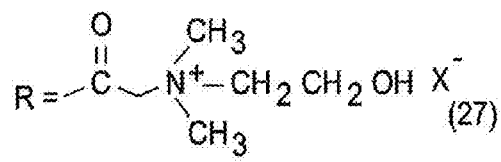
(27)
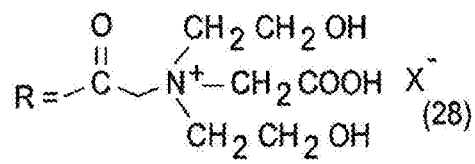
(28)

FIG. 1D
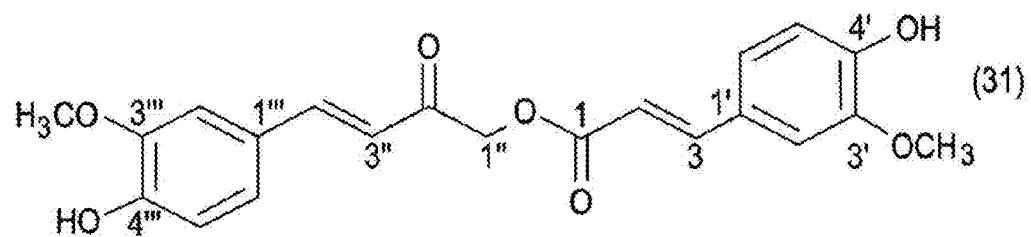
(31)
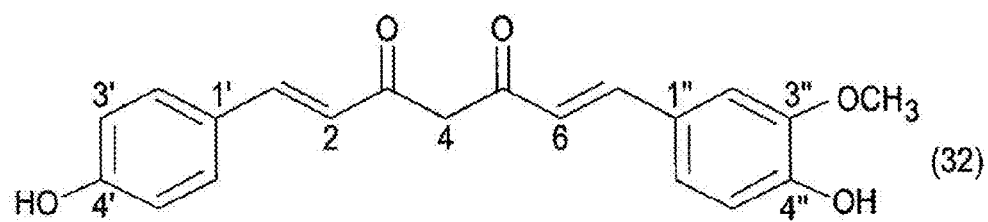
(32)
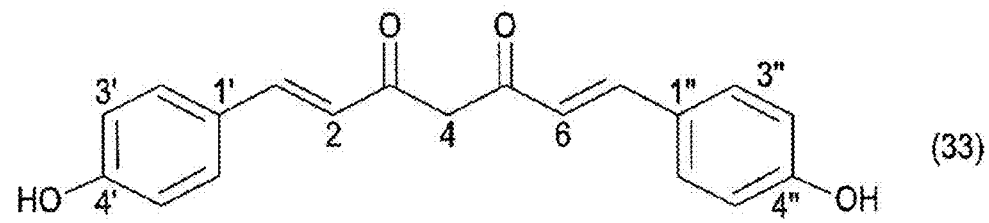
(33)
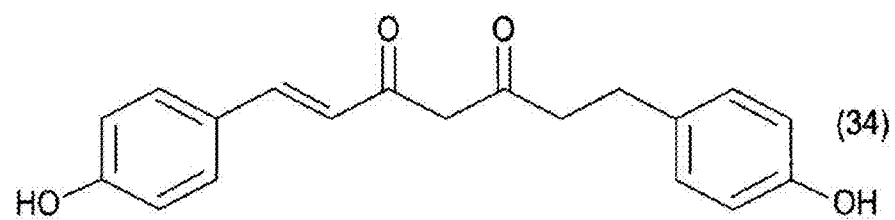
(34)

Curcumin

Curcumin-resveratrol I

Resveratrol

Curcumin-resveratrol II

Curcumin resveratrol I

Curcumin-resveratrol II

FIG. 6
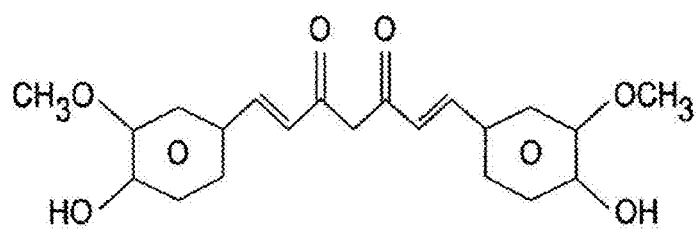
Curcumin
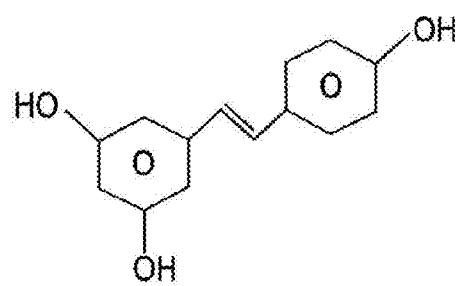
Resveratrol
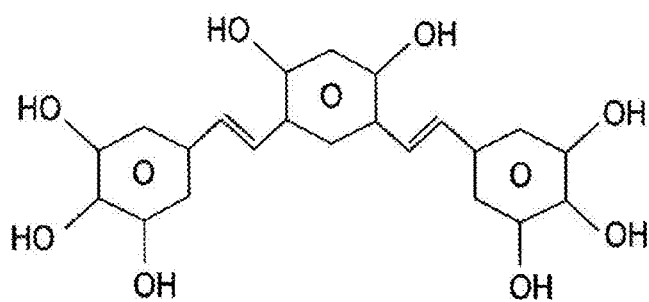
Curcumin-resveratrol Resveratrol-circumin

FIG. 8
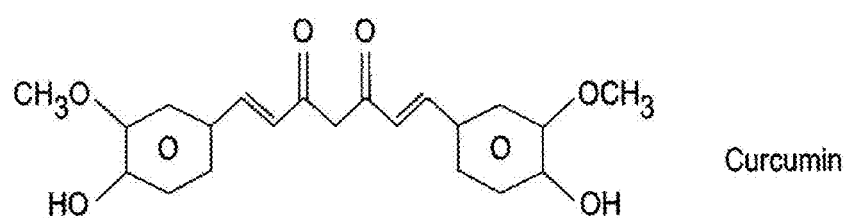
Curcumin
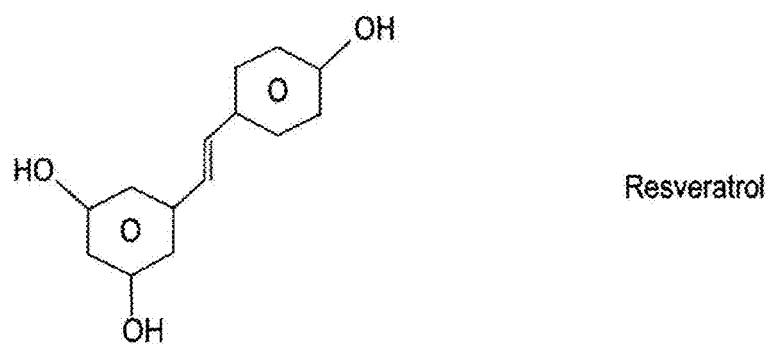
Resveratrol
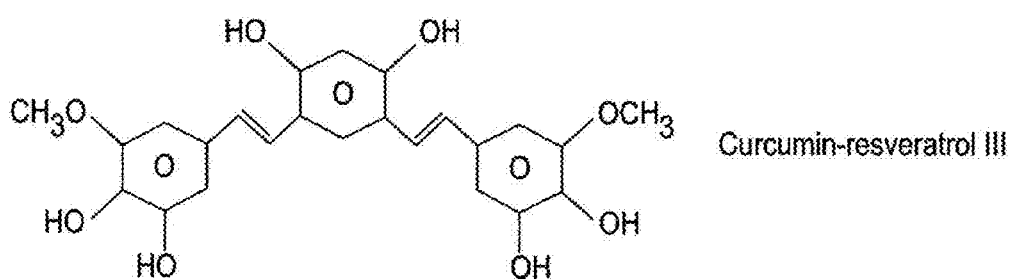
Curcumin-resveratrol III

FIG. 9
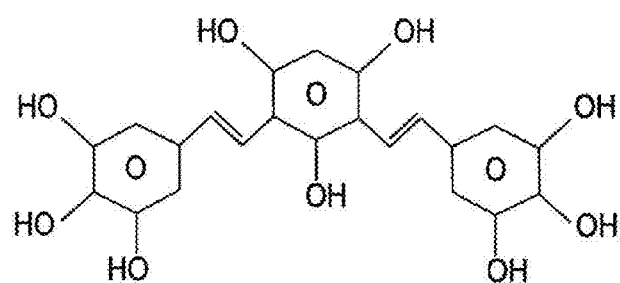
Curcumin-oxy resveratrol II
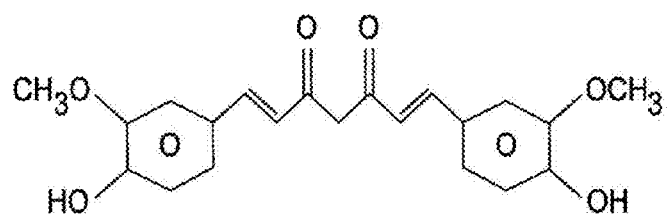
Curcumin
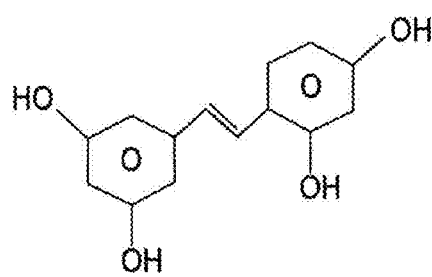
Oxy resveratrol Curcumin-piceatannol

FIG. 15
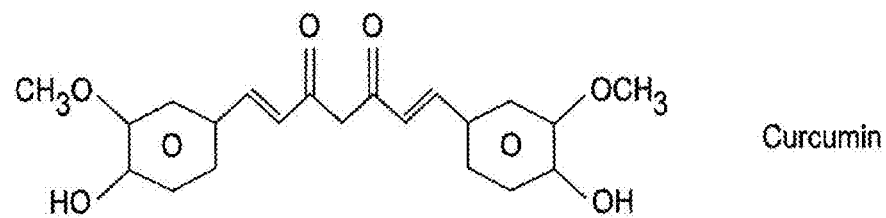
Curcumin
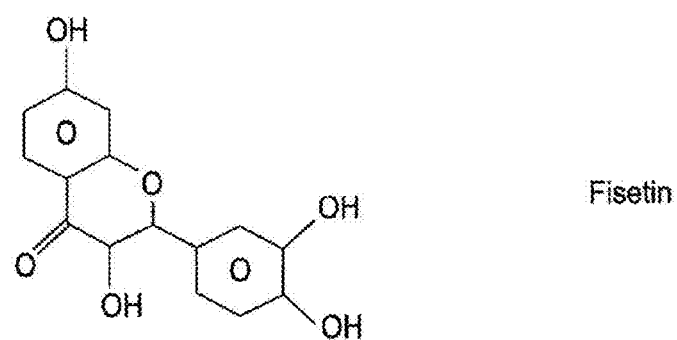
Fisetin
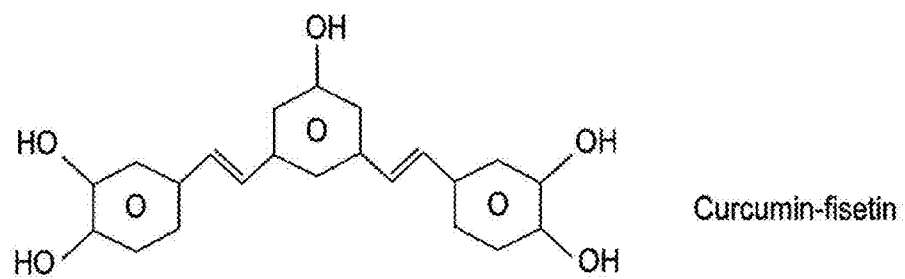
Curcumin-fisetin

CURCUMIN DERIVATIVES

RELATED APPLICATIONS

This application is a continuation-in-part of International Application No. PCT/US2008/060569, which designated the United States and was filed on April 17, 2008, published in English, and which claims priority to, and is a continuation-in-part of, both U.S. application Ser. No. 11/736,278, filed Apr. 17, 2007 now abandoned and U.S. application No. 12/029,904, filed Feb. 12, 2008.

The entire teachings of the above applications are incorporated herein by reference.

BACKGROUND OF THE INVENTION

In Alzheimer's Disease (AD), the abnormal cleavage of beta amyloid protein precursor from the intracellular membrane often produces a protein Aβ 1-42 which is incompletely removed by normal clearance processes. It has been reported that soluble beta amyloid oligomers are highly neurotoxic. Moreover, over time, this soluble protein assemblage is deposited as a beta amyloid protein Aβ plaque within brain tissue, leading to the local destruction of neurons. The Aβ plaque deposition is also believed to provoke an inflammatory response by microglia and macrophages, which recognize the plaque as a foreign body. These cells are believed to respond to the plaque deposition by releasing pro-inflammatory cytokines and reactive oxygen species (ROS). Although the inflammatory response may be provoked in an effort to clear the brain tissue of the detrimental plaque, it is now believed that this inflammation also injures local neuronal tissue, thereby exacerbating AD. Soluble oligomers of beta amyloid or "ADDLs" are a neurotoxic species implicated in AD pathogenesis. Yang, *J. Biol. Chem.*, 280, 7, Feb. 18, 2005, 5892-5901.

In the book "*The Memory Cure*" (2003, McGraw-Hill, NY, N.Y.), Dr. Majid Fotuhi writes: "Pharmaceutical companies in search of magic drugs to treat Alzheimer's Disease need to pay close attention to curcumin."

It has been reported that 0.1-1.0 µM curcumin inhibits the in vitro formation of amyloid beta oligomers, and blocks the in vitro toxicity of $A\beta_{1-42}$ oligomers in differentiated neuroblastoma cells. Yang, *J. Biol. Chem.*, 280, 7, Feb. 18, 2005, 5892-5901. Curcumin also reduced the amount of soluble beta amyloid by 43% when provided in the diet of Alzheimer's transgenic mice in a low dose of 160 ppm. Lim, *J. Neurosci.*, 2001, Nov. 1, 21(21) 8370-7.

It appears that curcumin also beneficially reduces deposits of beta amyloid. In middle aged female Sprague-Dawley rats, 500 ppm dietary curcumin reduced amyloid beta deposits induced by beta amyloid infusion by about 80%. Frautschy, *Neurobiol. Aging*, 22, 2001, 993-1005. Curcumin also reduced beta amyloid plaque burden by about 30-40% when provided in the diet of Alzheimer's Transgenic mice in a low dose of 160 ppm. Lim, *J. Neurosci.*, 2001, Nov. 1, 21(21) 8370-7. This is advantageous because it is believed that the oxidative and inflammatory damage caused by AD is linked to microglial response to amyloid beta deposits. In addition to its beneficial action against soluble beta amyloid, curcumin has considerable anti-oxidative properties and also inhibits the expression of proinflammatory cytokines. Frank, *Ann. Clin. Psychiatry,* 2005, October-December 17, 4, 269-86, and Cole, *Neurobiol. Aging,* 26S (2005) S1 33-S1 36.

Because curcumin is able to effectively act against many targets of AD, it has been hypothesized that the 4.4 fold lower incidence of AD in the Indian population between the ages of 70 and 79 is due to the high dietary consumption of curcumin. Lim, *J. Neuroscience*, Nov. 1, 2001, 21(21) 8370-77. In those aged 80 years and older, age-adjusted Alzheimer's disease prevalence in India is roughly one-quarter the rates in the United States (4% versus 15.7%). Frautschy, *Neurobiol. Aging,* 22, 2001, 993-1005. Curcumin has been identified in review articles as one of the most promising candidates for long term AD study. Frank, *Ann. Clin. Psychiatry,* 2005, October-December 17, 4, 269-86, and Cole, *Neurobiol. Aging,* 26S (2005) S1 33-S1 36. Curcumin is currently the subject of an FDA approved IND clinical trial at the UCLA Alzheimer Center in the treatment of mild to moderate AD patients. Cole, *Neurobiol. Aging,* 26S (2005) S1 33-S1 36.

Because the above-mentioned in vivo effects of curcumin upon AD symptoms were achieved by providing curcumin in the diet, it appears that curcumin is effectively able to cross the blood brain barrier. As curcumin is highly lipophilic, it is expected to easily cross the blood brain barrier. Frautschy, *Neurobiol. Aging,* 22, 2001, 993-1005. Indeed, it has been reported that in vivo studies show that curcumin injected peripherally into aged Tg mice crossed the blood brain barrier and bound amyloid plaques. Yang, *J. Biol. Chem.*, 280, 7, Feb. 18, 2005, 5892-5901.

SUMMARY OF THE INVENTION

Despite the beneficial effects of curcumin, the present inventors have noted that there are many bioavailability problems associated with the oral delivery of curcumin. First, because curcumin does not easily penetrate the human digestive tract and is subject to intestine-based metabolism and rejection, less than 1% of oral curcumin enters the plasma. Second, the small amount of curcumin that enters the bloodstream is rapidly metabolized by the liver and kidney. Therefore, although curcumin is highly lipophilic (and so easily crosses the blood brain harrier), only very small amounts of orally administered curcumin are registered in the serum and in the brain tissue. One study found that ingesting up to 3.6 g of curcumin per day produced a plasma curcumin level in the range of only about 10 nM. Sharma, *Clin. Cancer Res.,* 2004, Oct. 15, 10(20) 6847-54. A second study found that ingesting up to 6-8 g of curcumin per day produced a peak serum level in the range of about 0.51-1.77 µM. Third, it has been reported that high oral doses of curcumin in the range of 4,000-8,000 mg/day cause problems such as headache, rash and diarrhea, likely produced by metabolites of curcumin. Accordingly, it appears that the above-cited plasma curcumin concentrations (10 nM-1.77 µM) represent the practical upper limit of oral dosing of curcumin. Yang, supra, concludes that higher >(5 µM) concentrations of curcumin are not likely to occur in the brain with oral dosing. In fact, Wang reports that injection of 30 mg/kg of curcumin results in a peak curcumin concentration in brain tissue of only about 0.15 ng/mg, which is about 0.40 uM.

It appears that, in the brain tissue concentration range about 1 uM, some but not all of the beneficial therapeutic qualities of curcumin are realized. For example, it has been reported that 0.1-1.0 µM curcumin inhibits the in vitro formation of amyloid beta oligomers, and blocks the in vitro toxicity of $A\beta_{1-42}$ oligomers in differentiated neuroblastoma cells. Yang, *J. Biol. Chem.*, 280, 7, Feb. 18, 2005, 5892-5901. However, there also appear to be a number of AD-related therapeutic qualities of curcumin that are only realized at higher curcumin concentrations. For example, Yang reports that, whereas 0.25-4 uM concentrations of curcumin only minimally prevent the formation of toxic beta amyloid oligomer formation in vitro, 16-64 uM concentrations of curcumin completely prevent the formation of toxic beta amyloid oligomer formation. Yang also notes that curcumin has the potential to inhibit copper binding of beta amyloid, but concludes that it is not clear whether curcumin's avidity for copper and potential concentration in the brain will be enough to directly alter CNS beta amyloid metal binding.

In some embodiments, the present invention relates to the intranasal administration of a formulation comprising an effective amount of curcumin. In particular, in some embodiments, the present invention relates to the intranasal administration of a formulation comprising an effective amount of curcumin to the olfactory mucosa across the cribriform plate and into the brain in order to treat a neurodegenerative disease, such as AD.

An objective of some embodiments of the present invention is to improve curcumin brain bioavailability by administering curcumin via the nasal route in order to deliver curcumin through the olfactory mucosa and to the brain, and to reduce the dose required for its beneficial effect. As curcumin is highly lipophilic, it will easily pass through the olfactory mucosa located high in the nasal cavity, and enter olfactory neurons and thereby the brain. This mode of delivery will also pass less curcumin into the circulation, and so will result in lower plasma concentrations of metabolites of curcumin, and, therefore, fewer side effects. Intranasal delivery will improve drug bioavailability to the brain by passive diffusion through the olfactory mucosa, thereby avoiding extensive hepatic first-pass metabolism which significantly lowers the plasma and brain concentrations of curcumin administered orally. Therefore, small doses of curcumin can be administered which will result in fewer side effects, and the drug will be more tolerable and more effective.

Lipophilic drugs such as curcumin generally achieve higher brain levels after intranasal administration than after oral or intravenous administration. Therefore, the nasal route of administration of curcumin may help to enhance the effectiveness of curcumin in the brain (the site of action). Additionally, as curcumin is heavily metabolized by the liver, administration by the nasal route may help to reduce drug interactions with other drugs that are also extensively metabolized by the liver. Lastly, because intranasally administered curcumin will passively diffuse through the olfactory mucosa and into the olfactory bulb, which is connected to the hippocampus and amygdala through the limbic system. it is believed that intranasal administration of curcumin will preferentially deposit in the hippocampus and amygdala portions of the brain. These regions are believed to be origination sites of Alzheimer's Disease. Therefore, in accordance with the present invention, there is provided a method for administering curcumin to a brain of a mammal, comprising: a) applying a pharmaceutical composition comprising curcumin to an upper third of a nasal cavity of the mammal, wherein the curcumin is absorbed through an olfactory mucosa and transported to the brain of the mammal.

In one embodiment, the present invention is directed to a compound represented by the following structural formula:

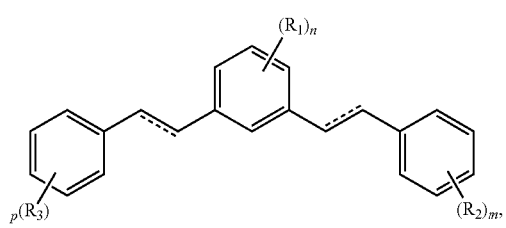

(I)

or a pharmaceutically acceptable salt thereof, wherein:
═════ represents a single bond or a double bond;
each $R_1$, $R_2$ and $R_3$ are independently selected from the group consisting of —OH, —O($C_1$-$C_6$)alkyl, halo, —C(Y)$_3$ and —OP;
Y is a halogen;

P is selected from the group consisting of —C(O)—($C_1$-$C_6$)alkylene-N($R_5$)($R_6$),

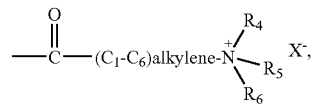

—C(O)—N($R_7$)—($C_1$-$C_6$)alkylene-COOH, —C(O)—($C_1$-$C_6$)alkylene-heterocyclyl and —C(O)—($C_1$-$C_6$)alkylene-aryl;

each $R_4$, $R_5$ and $R_6$ are independently selected from —H and ($C_1$-$C_6$)alkyl;
$R_7$ is —H or ($C_1$-$C_4$)alkyl;
$X^-$ is an anion;
n is an integer from 1 to 4;
m is an integer from 1 to 5; and
p is an integer from 1 to 5, wherein each alkyl is optionally substituted with one or more substituents independently selected from —OH, —O—($C_1$-$C_4$)alkyl, —COOH, —O—C(O)—($C_1$-$C_4$)alkyl, —N($R_7$)$_2$ and —$\overset{+}{N}$($R_7$)$_3$$X^-$.

In another embodiment, the present invention is directed to a pharmaceutical composition comprising a pharmaceutically acceptable carrier or diluent and a compound represented by Structural Formula (I) or a pharmaceutically acceptable salt thereof. The pharmaceutical composition is used in therapy, such as treating Alzheimer's disease, cancer, diabetes, arthritis or sclerosis in a subject.

Another embodiment of the present invention is a method of treating a subject with a disorder selected from Alzheimer's disease, cancer, diabetes, arthritis and sclerosis comprising administering to the subject an effective amount of a compound represented by Structural Formula (I) or a pharmaceutically acceptable salt thereof.

Another embodiment of the present invention is the use of a compound represented by Structural Formula (I) or a pharmaceutically acceptable salt thereof for the manufacture of a medicament for treating Alzheimer's disease, cancer, diabetes, arthritis or sclerosis in a subject.

Another embodiment of the present invention is the use of a compound represented by Structural Formula (I) or a pharmaceutically acceptable salt thereof in therapy, such as treating Alzheimer's disease, cancer, diabetes, arthritis or sclerosis in a subject.

BRIEF DESCRIPTION OF THE DRAWINGS

FIGS. 1A through 1C disclose novel curcumin prodrugs of the present invention (1)-(30).
FIG. 1D discloses preferred curcumin analogs (31)-(34) that are candidate parent compounds for making prodrugs thereof.
FIGS. 2-16 disclose curcumin, resveratrol, and various curcumin derivatives that are hybrids of curcumin and various other natural polyphenols. Each of these derivatives is a triphenolic compound, wherein the intermediate diketone structure of curcumin is replaced with a phenolic group. The resulting compound retains the spacing between the two phenols of curcumin, and also possesses the biphenolic spacing of the additional polyphenol.
FIG. 2 discloses the structures of curcumin, resveratrol, and two curcumin-resveratrol hybrids. Note how each of the hybrids retains the interphenolic spacing of each of curcumin and reveratrol.
FIG. 3 discloses a method of making the curcumin-resveratrol I hybrid.
FIG. 4 discloses a method of making the curcumin-resveratrol II hybrid.

FIG. 5 discloses a method of making a curcumin-resveratrol hybrid having three hydroxyl groups in each of the central phenolic group and lateral phenolic groups.

FIG. 6 discloses curcumin, resveratrol and a hybrid thereof, wherein all of the phenolics of the natural compounds are represented in the hybrid, providing trihydroxyl lateral phenolic groups and a dihydroxyl central phenolic group.

FIG. 7 discloses a method of making the curcumin-resveratrol hybrid of FIG. 6.

FIG. 8 is similar to the hybrid of FIG. 6, but wherein the methoxy groups of the base curcumin molecule are retained.

FIG. 9 discloses curcumin, oxyresveratrol and a hybrid thereof, wherein all of the hydroxyls/phenolics of the natural compounds are represented in the hybrid, providing trihydroxyl lateral phenolic groups and a trihydroxyl central phenolic group.

FIG. 10 discloses curcumin, piceatannol and a hybrid thereof, wherein all of the hydroxyls/phenolics of the natural compounds are represented in the hybrid, providing trihydroxyl lateral phenolic groups and a trihydroxyl central phenolic group.

FIG. 11 discloses a method of making a curcumin-resveratrol hybrid, wherein all of the hydroxyls/phenolics of the natural compounds are represented in the hybrid, providing trihydroxyl lateral phenolic groups and a dihydroxyl central phenolic group.

FIG. 12 discloses curcumin, bisdemethoxycurcumin (BDMC), resveratrol and curcumin hybrids thereof, wherein all of the phenolics of the natural compounds are represented in the hybrid, providing hydroxyl demethoxy lateral phenolic groups and a hydroxy or dihydroxyl central phenolic group.

FIG. 13 provides a method of making the compound of FIG. 12 that has hydroxyl demethoxy lateral phenolic groups and a hydroxy central phenolic group.

FIG. 14 provides a method of making the compound of FIG. 12 that has hydroxyl demethoxy lateral phenolic groups and a dihydroxy central phenolic group.

FIG. 15 discloses curcumin, fisetin and hybrids thereof, wherein all of the phenolics of the natural compounds are represented in the hybrid, providing dihydroxyl phenolic groups and a hydroxy central phenolic group in the positions common with the two natural compounds.

FIG. 16 provides a method of making the compound of FIG. 15.

DETAILED DESCRIPTION OF THE INVENTION

Figure 2:
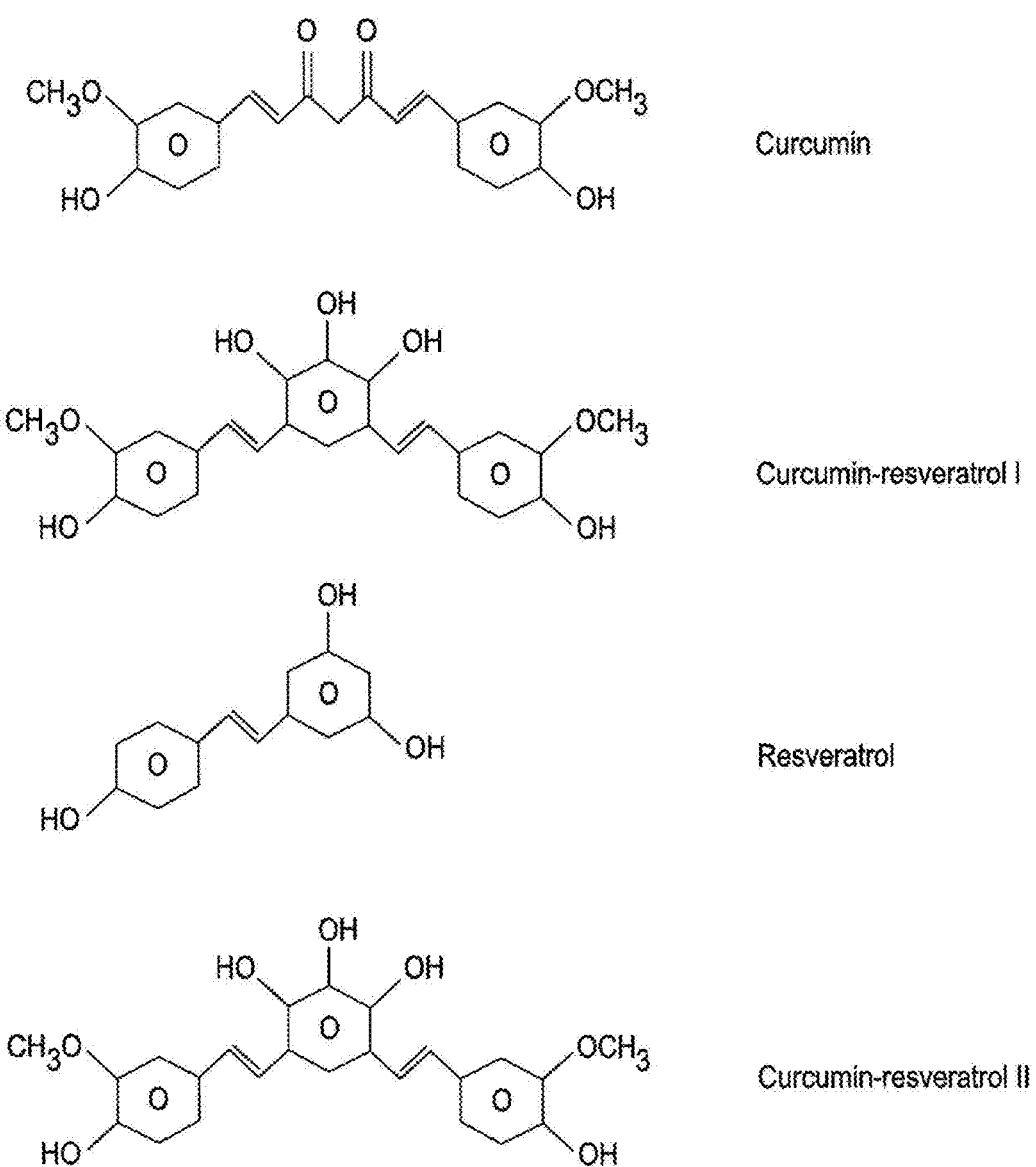

The present invention is directed to a compound represented by Structural Formula (I) or a pharmaceutically acceptable salt thereof. Values and alternative values for the variables in Structural Formula (I) and for each of the embodiments described herein are defined as the following:

===== represents a single bond or a double bond. In one embodiment, ===== represents a double bond.

Each $R_1$, $R_2$, and $R_3$ are independently selected from the group consisting of —OH, —O($C_1$-$C_6$)alkyl, halo, —C(Y)$_3$ and —OP. In one embodiment, each $R_1$, $R_2$, and $R_3$ are independently selected from the group consisting of —OH, —O($C_1$-$C_6$)alkyl and —OP. In another embodiment, each $R_1$, $R_2$, and $R_3$ are independently selected from the group consisting of —OH, —OCH$_3$ and —OP. In a further embodiment, each $R_1$, $R_2$ and $R_3$ are independently —OH or —OCH$_3$.

Y is a halogen (—F, —Cl, —Br or —I). In one embodiment, Y is —F, —Cl or —Br.

P is a hydrolyzable group. In one embodiment, P is selected from the group

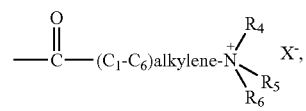

consisting of —C(O)—($C_1$-$C_6$)alkylene-N($R_5$)($R_6$), —C(O)—N($R_7$)—($C_1$-$C_6$)alkylene-COOH, —C(O)—($C_1$-$C_6$)alkylene-heterocyclyl and —C(O)—($C_1$-$C_6$)alkylene-aryl. In another embodiment, P is selected from the group

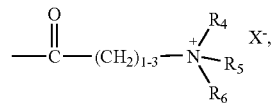

consisting of —C(O)—(CH$_2$)$_{1-3}$—N($R_5$)($R_6$), —C(O)—NH—(CH$_2$)$_{1-3}$—COOH, —C(O)—(CH$_2$)-heterocyclyl and —C(O)—(CH$_2$)-phenyl. In a further embodiment, P is selected from the group consisting of the R groups depicted in FIGS. 1A-1C.

Each $R_4$, $R_5$ and $R_6$ are independently selected from —H and ($C_1$-$C_6$)alkyl.

$R_7$ is —H or ($C_1$-$C_4$)alkyl.

$X^-$ is an anion. In one embodiment, $X^-$ is Cr.

n is an integer from 1 to 4. In one embodiment, n is 1. In another embodiment, n is 2. In another embodiment, n is 3.

m is an integer from 1 to 5. In one embodiment, m is an integer from 1 to 3. In one embodiment, m is 1. In another embodiment, m is 2. In yet another embodiment, m is 3.

p is an integer from 1 to 5. In one embodiment, p is an integer from 1 to 3. In one embodiment, p is 1. In another embodiment, p is 2. In yet another embodiment, p is 3.

Each alkyl described above is optionally substituted with one or more substituents independently selected from —OH, —O—($C_1$-$C_4$)alkyl, —COOH, —O—C(O)—($C_1$-$C_4$)alkyl, —N($R_7$)$_2$ and —$\overset{+}{N}$($R_7$)$_3$ $X^-$. In one embodiment, the substituents are independently selected from —OH, —OMe and —COOH.

Each aryl or heterocyclyl described above is independently substituted with one or more substituents independently selected from halo, ($C_1$-$C_4$)alkyl, —OH, —O—($C_1$-$C_4$)alkyl, —COOH, —O—C(O)—($C_1$-$C_4$)alkyl, —N($R_7$)$_2$ and —$\overset{+}{N}$($R_7$)$_3$ $X^-$, wherein each alkyl is optionally substituted with halo, —OH, —O—($C_1$-$C_4$)alkyl, —COOH, —N($R_7$)$_2$ and —$\overset{+}{N}$($R_7$)$_3$ $X^-$. In one embodiment, each aryl or heterocyclyl is independently substituted with one or more substituents independently selected from ($C_1$-$C_4$)alkyl, —N($R_7$)$_2$ and —$\overset{+}{N}$($R_7$)$_3$ $X^-$, wherein each alkyl is optionally substituted with —N($R_7$)$_2$ and —$\overset{+}{N}$($R_7$)$_3$ $X^-$.

In a first alternative embodiment, the compound of the present invention is represented by Structural Formula (II):

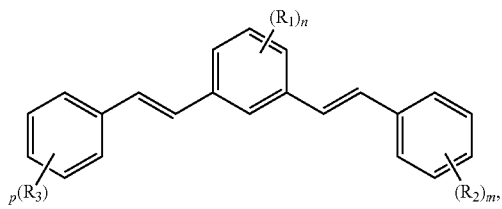

or a pharmaceutically acceptable salt thereof. Values and specific values for the variables are as described above for Structural Formula (I).

In a second alternative embodiment, for the compounds represented by Structural Formula (II), $R_2$ and $R_3$ are the same; and m and p are the same.

In a third alternative embodiment, for compounds represented by Structural Formula (II), $R_1$ is —OH or —O—($C_1$-$C_6$)alkyl and the remainder of the variables are as described above in the first or second alternative embodiment.

In a fourth alternative embodiment, P is selected from the group consisting of —C(O)—(CH$_2$)$_{1-3}$—N($R_5$)($R_6$),

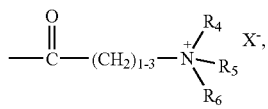

—C(O)—NH—(CH$_2$)$_{1-3}$—COOH, —C(O)—(CH$_2$)-heterocyclyl and —C(O)—(CH$_2$)-phenyl. The remainder of the variables are as described above in the third alternative embodiment.

In a fifth alternative embodiment, the compounds of the present invention are represented by a structural formula selected from the following structural formulas:

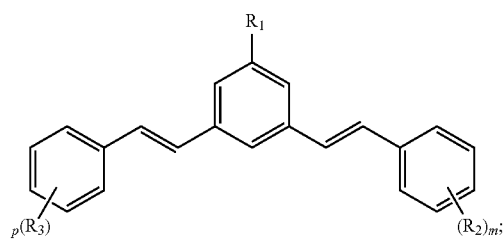

(III)

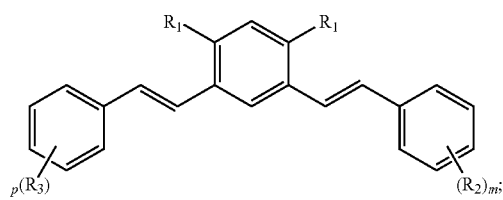

(IV)

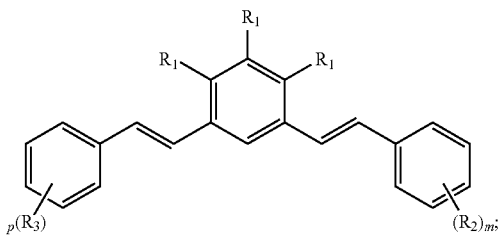

(V)

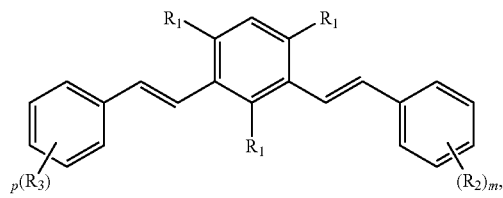

(VI)

or a pharmaceutically acceptable salt thereof. Values and specific values for variables in Structural Formulas (III)-(VI) are as described above in the fourth alternative embodiment.

In one embodiment, $R_1$ is —OH or —OMe and the remainder of the variables are as described above in the fifth alternative embodiment.

In another embodiment, m and p are an integer from 1 to 3 and the remainder of the variables are as described above in the fifth alternative embodiment.

In another embodiment, $R_1$ is —OH or —OMe; m and p are an integer from 1 to 3 and the remainder of the variables are as described above in the fifth alternative embodiment.

In a sixth alternative embodiment, the compounds of the present invention are represented by a structural formula selected from the following structural formulas:

(IIIa)

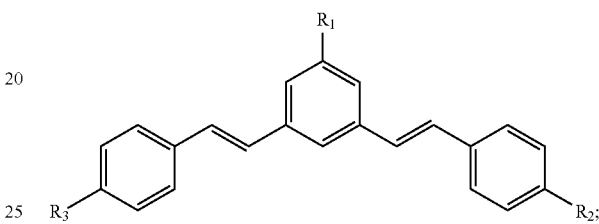

(IIIb)

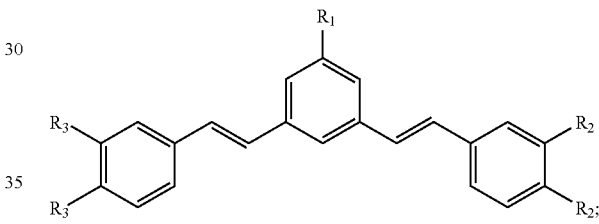

(IIIc)

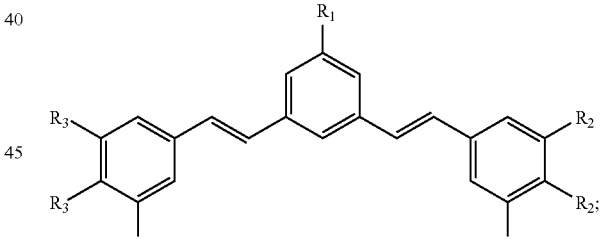

(IVa)

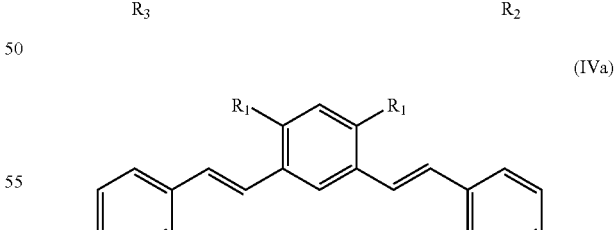

(IVb)

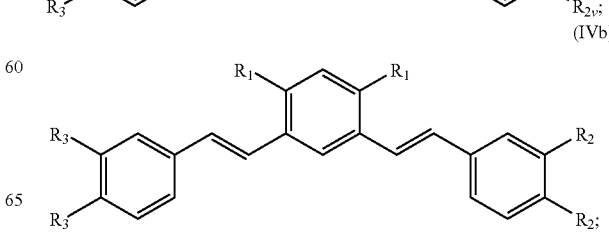

(IVc)
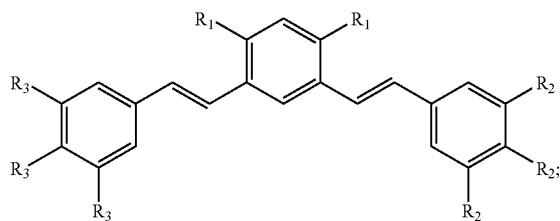
(Va)
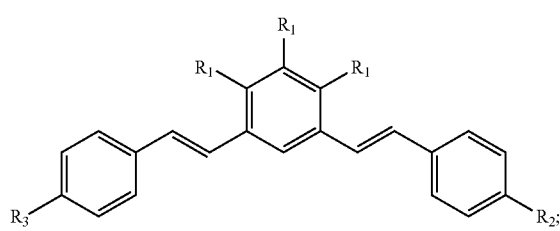
(Vb)
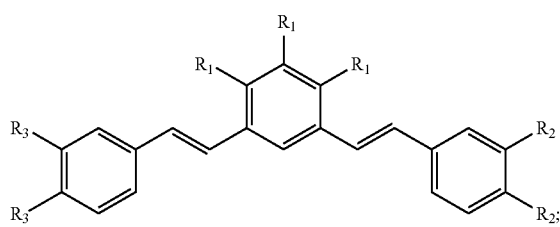
(Vc)
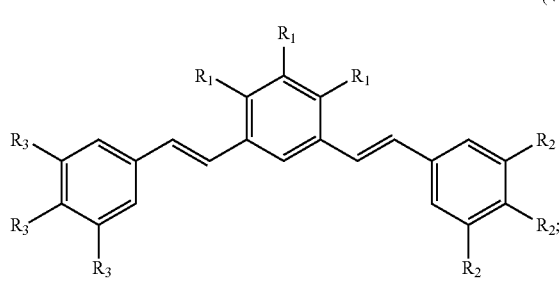
(VIa)
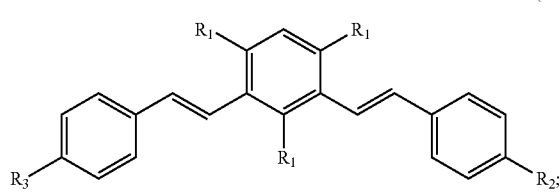
(VIb)
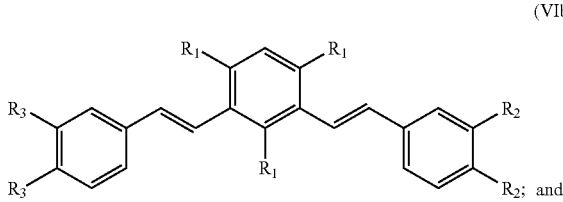
(VIc)
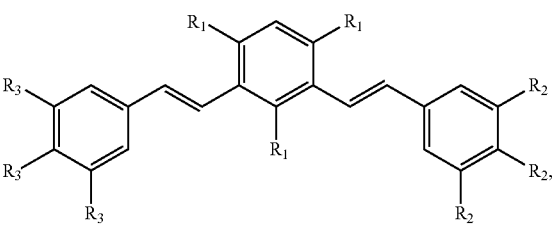
or a pharmaceutically acceptable salt thereof. Values and specific values for the variables in Structural Formulas (IIIa)-(IIIc), (IVa)-(IVc), (Va)-(Vc) and (VIa)-(VIc) are as described above in the fifth alternative embodiment.
Exemplary compounds represented by Structural Formula (I) are shown below:
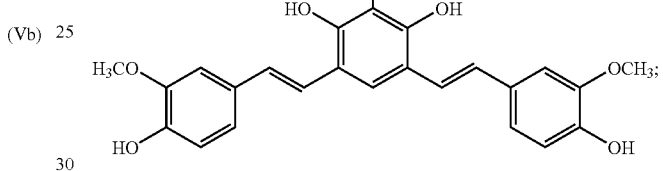
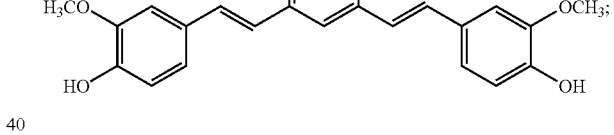
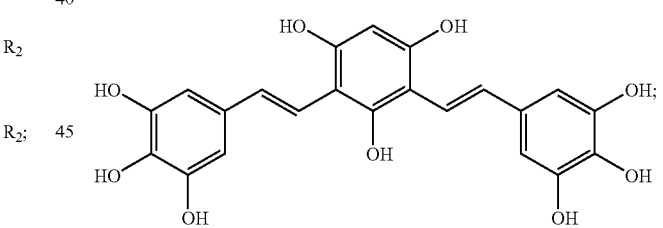
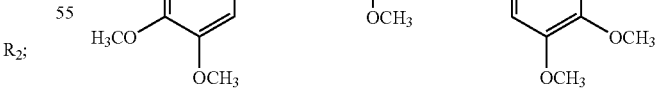
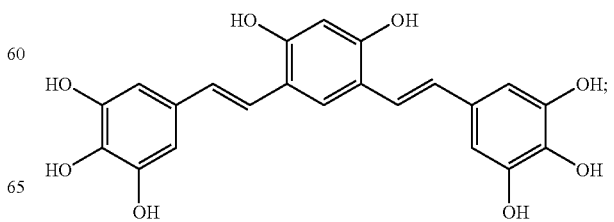

-continued

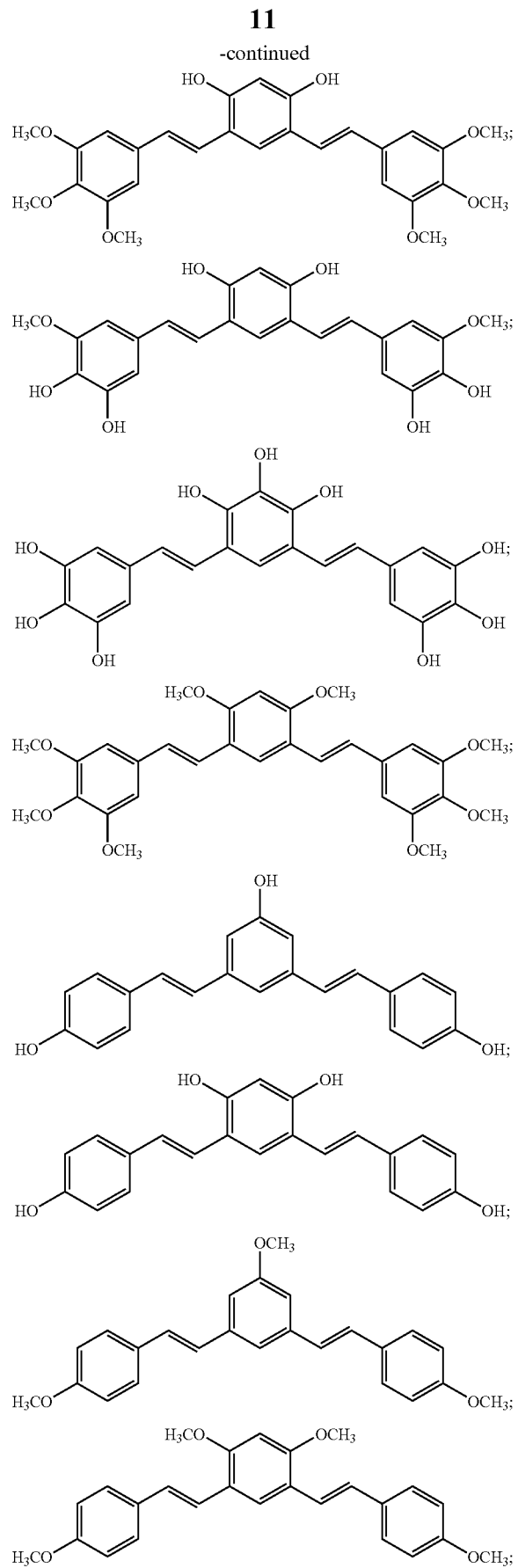

-continued

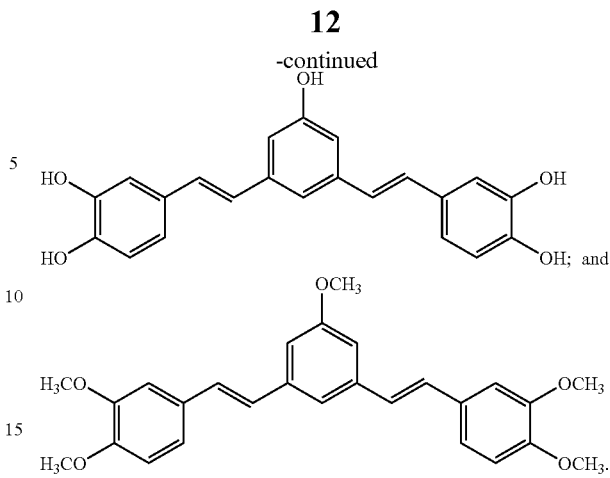

In one embodiment, each $R_2$ and $R_3$ are independently —OH or —OMe and the remainder of the variables are as described above in the sixth alternative embodiment.

As used herein, "alkyl" means a saturated aliphatic branched or straight-chain monovalent hydrocarbon radical having the specified number of carbon atoms. Thus, "$(C_1$-$C_6)$ alkyl" means a radical having from 1-6 carbon atoms in a linear or branched arrangement. "$(C_1$-$C_6)$alkyl" includes methyl, ethyl, propyl, butyl, pentyl and hexyl.

"Alkylene" means a saturated aliphatic straight-chain divalent hydrocarbon radical having the specified number of carbon atoms. Thus, "$(C_1$-$C_6)$ alkylene" means a divalent saturated aliphatic radical having from 1-6 carbon atoms in a linear arrangement, e.g., —[$(CH_2)_n$]—, where n is an integer from 1 to 6. "$(C_1$-$C_6)$alkylene" includes methylene, ethylene, propylene, butylene, pentylene and hexylene.

"Aryl" or "aromatic" means an aromatic monocyclic or polycyclic (e.g., bicyclic or tricyclic) carbocyclic ring system. In one embodiment, "aryl" is a 6-12 membered monocylic or bicyclic system. Aryl systems include, but not limited to, phenyl, naphthalenyl, fluorenyl, indenyl, azulenyl, and anthracenyl. In one embodiment, "aryl" is phenyl optionally substituted with substituents described above.

"Heterocyclyl" means a cyclic 4-12 membered saturated or unsaturated aliphatic ring containing 1, 2, 3, 4 or 5 heteroatoms independently selected from N, O or S or a heteroaromatic ring. When one heteroatom is S, it can be optionally mono- or di-oxygenated (i.e., —S(O)— or —S(O)$_2$—). The heterocyclyl can be monocyclic, fused bicyclic, bridged bicyclic, Spiro bicyclic or polycyclic.

"Saturated heterocyclyl" means an aliphatic heterocyclyl group without any degree of unsaturation (i.e., no double bond or triple bond). It can be monocyclic, fused bicyclic, bridged bicyclic, spiro bicyclic or polycyclic.

Examples of monocyclic saturated heterocyclyls include, but are not limited to, azetidine, pyrrolidine, piperidine, piperazine, azepane, hexahydropyrimidine, tetrahydrofuran, tetrahydropyran, morpholine, thiomorpholine, thiomorpholine 1,1-dioxide, tetrahydro-2H-1,2-thiazine, tetrahydro-2H-1,2-thiazine 1,1-dioxide, isothiazolidine, isothiazolidine 1,1-dioxide. Examples of heteroaromatic rings include, but are not limited to, furan, thiophene, pyrrole, imidazole, pyrazole, oxazole, isoxazole, triazole, isothiazole, 1,2,3-triazole, 1,2,4-triazole, 1,3,4-oxadiazole, 1,2,5-thiadiazole, 1,2,5-thiadiazole 1-oxide, 1,2,5-thiadiazole 1,1-dioxide, 1,3,4-thiadiazole, pyridine, pyridine-N-oxide, pyrazine, pyrimidine, pyridazine, 1,2,4-triazine, 1,3,5-triazine, and tetrazole.

A fused bicyclic heterocyclyl has two rings which have two adjacent ring atoms in common. The first ring is a monocyclic heterocyclyl and the second ring is a monocyclic carbocycle (such as a cycloalkyl or phenyl) or a monocyclic heterocyclyl. For example, the second ring is a ($C_3$-$C_6$)cycloalkyl, such as cyclopropyl, cyclobutyl, cyclopentyl and cyclohexyl. Alternatively, the second ring is phenyl. Examples of fused bicyclic heterocyclyls include, but are not limited to, octahydrocyclopenta[c]pyrrolyl, indoline, 2,3-dihydro-1H-benzo[d]imidazole, 2,3-dihydrobenzo[d]oxazole, 2,3-dihydrobenzo[d]thiazole, octahydrobenzo[d]oxazole, octahydro-1H-benzo[d]imidazole, octahydrobenzo[d]thiazole, octahydrocyclopenta[c]pyrrole, 3-azabicyclo[3.1.0]hexane, 3-azabicyclo[3.2.0]heptane, indolizine, indole, isoindole, indazole, benzimidazole, benzthiazole, purine, quinoline, isoquinoline, cinnoline, phthalazine, quinazoline, quinoxaline, 1,8-naphthyridine, and pteridine.

A spiro bicyclic heterocyclyl has two rings which have only one ring atom in common. The first ring is a monocyclic heterocyclyl and the second ring is a monocyclic carbocycle (such as a cycloalkyl or phenyl) or a monocyclic heterocyclyl. For example, the second ring is a ($C_3$-$C_6$)cycloalkyl. Alternatively, the second ring is phenyl. Examples of spiro bicyclic heterocyclyl include, but are not limited to, azaspiro[4.4]nonane, 7-azaspiro[4.4]nonane, azaspiro[4.5]decane, 8-azaspiro[4.5]decane, azaspiro[5.5]undecane, 3-azaspiro[5.5]undecane and 3,9-diazaspiro[5.5]undecane.

A bridged bicyclic heterocyclyl has two rings which have three or more adjacent ring atoms in common. The first ring is a monocyclic heterocyclyl and the other ring is a monocyclic carbocycle (such as a cycloalkyl or phenyl) or a monocyclic heterocyclyl. Examples of bridged bicyclic heterocyclyls include, but are not limited to, azabicyclo[3.3.1]nonane, 3-azabicyclo[3.3.1]nonane, azabicyclo[3.2.1]octane, 3-azabicyclo[3.2.1]octane, 6-azabicyclo[3.2.1]octane and azabicyclo[2.2.2]octane, 2-azabicyclo[2.2.2]octane.

Polycyclic heterocyclyls have more than two rings, one of which is a heterocyclyl (e.g. three rings resulting in a tricyclic ring system) and adjacent rings having at least one ring atom in common. Polycyclic ring systems include fused, bridged and spiro ring systems. A fused polycyclic ring system has at least two rings that have two adjacent ring atoms in common. A spiro polycyclic ring system has at least two rings that have only one ring atom in common. A bridged polycyclic ring system has at least two rings that have three or more adjacent ring atoms in common.

"Carbocycle" means a cyclic group with only ring carbon atoms.

"Halogen" used herein refers to fluorine, chlorine, bromine, or iodine. "Halo" used herein refers to fluoro, chloro, bromo or iodo.

"Anion" used herein refers to a negatively charged ion. An anion can be an inorganic anion or an organic anion. Anion can include, but is not limited to, halides (F, Cl$^-$, Br$^-$ or I$^-$), $NO_3^-$, $PO_4^{3-}$, $HPO_4^{2-}$, $H_2PO_4^-$, $SO_4^{2-}$, acetate, oxalate, tetrakis(1-imidazolyl)borate, $BF_4^-$, $CF_3SO_3^-$, $PF_6^-$, $BPh_4^-$, $B(3,5-(CF_3)_2C_6H_3))_4^-$, carbonate, benzenesulfonate, benzoate, bicarbonate, bitartrate, calcium edetate, camsylate, citrate, edetate, edisylate, estolate, esylate, fumarate, glyceptate, gluconate, glutamate, glycollylarsanilate, hexylresorcinate, hydroxynaphthoate, isethionate, lactate, lactobionate, malate, maleate, mandelate, mesylate, methylsulfate, mucate, napsylate, nitrate, pamoate, pantothenate, polygalacturonate, salicylate, stearate, subacetate, succinate, tannate, tartrate, teoclate, tosylate, and triethiodide.

As used herein, the term "hydrolyzable group" refers to a moiety that, when present in a molecule of the invention, yields a phenol or salt thereof upon hydrolysis. Hydrolysis can occur, for example, spontaneously under acidic or basic conditions in a physiological environment (e.g., blood, metabolically active tissues such as, for example, liver, kidney, lung, brain), or can be catalyzed by an enzyme(s), (e.g., esterase, peptidases, hydrolases, oxidases, dehydrogenases, lyases or ligases). A hydrolyzable group can confer upon a compound of the invention advantageous properties in vivo, such as improved water solubility, improved circulating half-life in the blood, improved uptake, improved duration of action, or improved onset of action.

In one embodiment, the hydrolyzable group does not destroy the biological activity of the compound. In an alternative embodiment, a compound with a hydrolyzable group can be biologically inactive, but can be converted in vivo to a biologically active compound.

Another embodiment of the present invention is a pharmaceutical composition comprising one or more pharmaceutically acceptable carriers and/or diluents and a compound disclosed herein or a pharmaceutically acceptable salt thereof.

"Pharmaceutically acceptable carrier" and "pharmaceutically acceptable diluent" means non-therapeutic components that are of sufficient purity and quality for use in the formulation of a composition of the invention that, when appropriately administered to an animal or human, typically do not produce an adverse reaction, and that are used as a vehicle for a drug substance (i.e., a compound of the present invention).

Pharmaceutically acceptable salts of the compounds of the present invention are also included. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of the compounds of the present invention containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

The invention also includes various isomers and mixtures thereof. Certain of the compounds of the present invention may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. When a chiral center is not defined as R or S, either a pure enantiomer or a mixture of both configurations is present.

"Racemate" or "racemic mixture" means a compound of equimolar quantities of two enantiomers, wherein such mixtures exhibit no optical activity; i.e., they do not rotate the plane of polarized light.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer that is present divided by the combined weight of the enantiomer that is present and the weight of its optical isomer.

The compounds described herein are useful for treating and/or preventing diseases and disorders including, but not limited to, Alzheimer's disease, cancer, arthritis and sclerosis. For example, compounds represented by Structural Formula (I) (e.g., compounds represented by Structural Formula (I) wherein at least one substituent selected from the group consisting of $R_1$, $R_2$ and $R_3$ is —$OCH_3$, are useful for treating and/or preventing disorders such as cancer.

Accordingly, the present invention also provides a method of treating or preventing a disorder selected from Alzheimer's disease, cancer, arthritis and sclerosis in a subject comprising administering to the subject an effective amount of a compound of the present invention or a pharmaceutically acceptable salt thereof.

In one embodiment, the disorder is Alzheimer's disease. In another embodiment, the disorder is cancer. In another embodiment, the disorder is arthritis. In yet another embodiment; the disorder is sclerosis.

Cancers that can be treated by the methods of the present invention include, but are not limited to, human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease.

As used herein, the term "subject" means a mammal in need of treatment or prevention, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of the specified treatment.

As used herein, the term "treating" or "treatment" refers to obtaining desired pharmacological and/or physiological effect. The effect can include achieving, partially or substantially, one or more of the following results: partially or totally reducing the extent of the disease, disorder or syndrome; ameliorating or improving a clinical symptom or indicator associated with the disorder; delaying, inhibiting or decreasing the likelihood of the progression of the disease, disorder or syndrome.

As used herein, "preventing" or "prevention" refers to reducing the likelihood of the onset or development of disease, disorder or syndrome.

"Effective amount" means that amount of active compound agent that elicits the desired biological response in a subject. In one embodiment, the effective amount of a compound of the invention is from about 0.01 mg/kg/day to about 1000 mg/kg/day, from about 0.1 mg/kg/day to about 100 mg/kg/day, or from about 0.5 mg/kg/day to about 50 mg/kg/day.

The invention further includes the process for making the composition comprising mixing one or more of the present compounds and an optional pharmaceutically acceptable carrier; and includes those compositions resulting from such a process, which process includes conventional pharmaceutical techniques.

The compositions of the invention include ocular, oral, nasal, transdermal, topical with or without occlusion, intravenous (both bolus and infusion), inhalable, and injection (intraperitoneally, subcutaneously, intramuscularly, intratumorally, or parenterally) formulations. The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

Compositions of the invention suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions, and suspensions.

The compositions of the invention may be administered in a form suitable for once-weekly or once-monthly administration. For example, an insoluble salt of the active compound may be adapted to provide a depot preparation for intramuscular injection (e.g. a decanoate salt) or to provide a solution for ophthalmic administration.

The dosage form containing the composition of the invention contains an effective amount of the active ingredient necessary to provide a therapeutic effect. The composition may contain from about 5,000 mg to about 0.5 mg (preferably, from about 1,000 mg to about 0.5 mg) of a compound of the invention or salt form thereof and may be constituted into any form suitable for the selected mode of administration. The composition may be administered about 1 to about 5 times per day. Daily administration or post-periodic dosing may be employed.

For oral administration, the composition is preferably in the form of a tablet or capsule containing, e.g., 500 to 0.5 milligrams of the active compound. Dosages will vary depending on factors associated with the particular patient being treated (e.g., age, weight, diet, and time of administration), the severity of the condition being treated, the compound being employed, the mode of administration, and the strength of the preparation.

The oral composition is preferably formulated as a homogeneous composition, wherein the active ingredient is dispersed evenly throughout the mixture, which may be readily subdivided into dosage units containing equal amounts of a compound of the invention. Preferably, the compositions are prepared by mixing a compound of the invention (or pharmaceutically acceptable salt thereof) with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binder agents include starch, gelatin, natural sugars (e.g., glucose and beta-lactose), corn sweeteners and natural and synthetic gums (e.g., acacia and tragacanth). Disintegrating agents include starch, methyl cellulose, agar, and bentonite.

Tablets and capsules represent an advantageous oral dosage unit form. Tablets may be sugarcoated or filmcoated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

Compounds of the invention may also be administered via a slow release composition; wherein the composition includes a compound of the invention and a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an active agent(s) and which slowly degrade/dissolve in a suitable environment (e.g., aqueous, acidic, basic and the like) to release the agent. Such particles degrade/dissolve in body fluids to release the active compound(s) therein. The particles are preferably nanoparticles or nanoemulsions (e.g., in the range of about 1 to 500 nm in diameter, preferably about 50-200 nm in diameter, and most preferably about 100 nm in diameter). In a process for preparing a slow release composition, a slow release carrier and a compound of the invention are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the compound of the invention.

The compounds of the invention may be administered orally. For oral administration, the pharmaceutical compositions may be in the form of, for example, a pill (e.g., a tablet, a capsule), suspension or liquid. Preferably, the compounds of the invention are formulated for oral administration as a pill. For example, the compounds disclosed herein may be incorporated for administration orally or by injection in a liquid form such as aqueous solutions, suitably flavored syrups, aqueous or oil suspensions, flavored emulsions with edible oils such as cottonseed oil, sesame oil, coconut oil or peanut oil and the like, or in elixirs or similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, and gelatin. The liquid forms in suitably flavored suspending or dispersing agents may also include synthetic and natural gums. For parenteral administration, sterile suspensions and solutions are desired. Isotonic preparations, which generally contain suitable preservatives, are employed when intravenous administration is desired.

The compounds may be administered parenterally via injection. A parenteral formulation may consist of the active ingredient dissolved in or mixed with an appropriate inert liquid carrier. Acceptable liquid carriers usually comprise aqueous solvents and other optional ingredients for aiding solubility or preservation. Such aqueous solvents include sterile water, Ringer's solution, or an isotonic aqueous saline solution. Other optional ingredients include vegetable oils (such as peanut oil, cottonseed oil, and sesame oil), and organic solvents (such as solketal, glycerol, and formyl): A sterile, non-volatile oil may be employed as a solvent or suspending agent.

The parenteral formulation is prepared by dissolving or suspending the active ingredient in the liquid carrier whereby the final dosage unit contains from 0.005 to 10% by weight of the active ingredient. Other additives include preservatives, isotonizers, solubilizers, stabilizers, and pain-soothing agents. Injectable suspensions may also be prepared, in which case appropriate liquid carriers, suspending agents and the like may be employed.

Compounds of the invention may be administered intranasally using a suitable intranasal vehicle.

In another embodiment, the compounds of this invention may be administered directly to the lungs by inhalation.

Compounds of the invention may also be administered topically or enhanced by using a suitable topical transdermal vehicle or a transdermal patch.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette. Preferably, the compositions are sterile and aqueous based, using purified water. In addition to the compound of the invention, an ophthalmic composition may contain one or more of: a) a surfactant such as a polyoxyethylene fatty acid ester; b) a thickening agents such as cellulose, cellulose derivatives, carboxyvinyl polymers, polyvinyl polymers, and polyvinylpyrrolidones, typically at a concentration n the range of about 0.05 to about 5.0% (wt/vol); c) (as an alternative to or in addition to storing the composition in a container containing nitrogen and optionally including a free oxygen absorber such as Fe), an anti-oxidant such as butylated hydroxyanisol, ascorbic acid, sodium thiosulfate, or butylated hydroxytoluene at a concentration of about 0.00005 to about 0.1% (wt/vol); d) ethanol at a concentration of about 0.01 to 0.5% (wt/vol); and e) other excipients such as an isotonic agent, buffer, preservative, and/or pH-controlling agent. The pH of the ophthalmic composition is desirably within the range of 4 to 8.

In certain embodiments, the compositions of this invention include one or more additional agents for example, therapeutic agents. An additional therapeutic agent can include an agent that is capable of treating, preventing or reducing the symptoms of a disease or disorder disclosed herein. Alternatively, an additional therapeutic agent can include an agent of benefit to a subject when administered in combination with a compound of this invention.

The present invention also includes methods of making the compounds described herein. In certain embodiments, compounds of present invention can be synthesized according to general schemes shown below as well as synthetic schemes shown in FIGS. 3-5, 7, 11, 13-15 and 16:

Scheme 1:

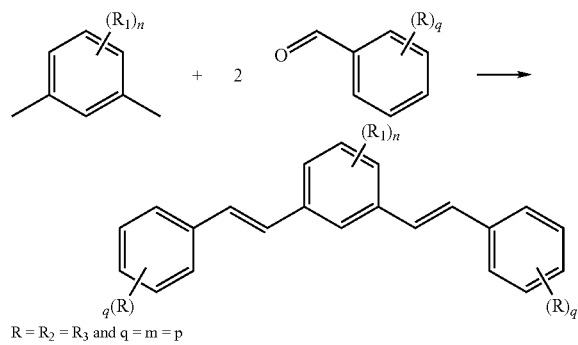

Scheme 2:

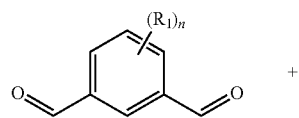

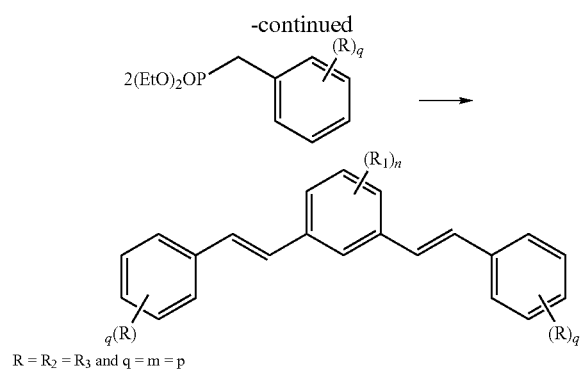

As used herein, curcumin is also known as diferuloylmethane or (E,E)-1,7-bis(4-hydroxy-3-methoxyphenyl)-1,6-heptadiene-3,5,-dione. Curcumin may be derived from a natural source, the perennial herb *Curcuma longa* L., which is a member of the Zingiberaceae family. The spice turmeric is extracted from the rhizomes of *Curcuma longa* L. and has long been associated with traditional-medicine treatments used in Hindu and Chinese medicine. Turmeric was administered orally or topically in these traditional treatment methods.

In some embodiments, curcumin or compounds of Structural Formula (I) is intranasally administered so that it produces a brain tissue concentration of at least 0.1 µM, more preferably at least 1 µM, more preferably at least 5 µM, more preferably at least 20 µM.

Without wishing to be tied to a theory, it is believed that a daily intranasal dose of at least about 0.2 mg/kg would be sufficient to produce the above-cited brain tissue concentrations. More preferably, the dose is at least 1 mg/kg, more preferably at least 10 mg/kg.

It is believed that applying a pharmaceutical composition comprising curcumin or compounds of Structural Formula (I) at the above cited levels to an upper third of a nasal cavity of the mammal. wherein the curcumin or compounds of Structural Formula (I) is absorbed through an olfactory mucosa and transported to the brain of the mammal, will result in attainment of these higher levels of curcumin in brain tissue.

It is known that the more lipophilic a molecule, the greater its propensity to cross the olfactory mucosa and the blood brain barrier. In this respect, it has been reported that the octanoh water partition coefficient of curcumin (logio PC) is 3.29. Therefore, curcumin is very lipophilic, and so should easily cross the olfactory mucosa and the blood brain barrier by passive diffusion.

It is further known that the blood brain barrier contains the p-glycoprotein (P-gp) transporter which effluxes a number of important molecules such as drugs. Accordingly, the behaviour of these pumps towards curcumin is pertinent to the question of whether curcumin will cross the olfactory mucosa and the blood brain harrier. Since it has been reported that curcumin lowers the expression of P-gp (Holland, *Biochem. Pharmacol.* 2006, Apr. 14, 71(8) 1146-54), it is believed that curcumin antagonizes these P-gp pumps. In addition to its ability to lower the expression of P-gp, it has been suggested that curcumin is able to modulate the function of hepatic P-gp. In both freshly-plated hepatocytes, containing low levels of Pgp, and 72 hour-cultured hepatocytes, containing high levels of Pgp, the Rhodamine-123 (R-123) efflux, which represents a specific functional test for Pgp-mediated transport, was inhibited by curcumin in a dose-dependent manner. (Romiti N, Tongiani R. Cervelli F, Chieli E., "Effects of curcumin on P-glycoprotein in primary cultures of rat hepatocytes," *Life Sci.* 1998; 62: 2349-58.).

Because the octanohwater partition coefficient of curcumin (logio PC) is 3.29 and curcumin has been shown to antagonize P-gp, it is believed that curcumin will easily cross the blood brain barrier. In this respect, it is helpful to compare these qualities of curcumin to those of hydroxyzine. It has been reported by Kandimalla, *Int'l J. Pharmaceutics,* 302 (2005) 133-144, that hydroxyzine HCl has a molecular weight of 447.8, an octanol:water partition coefficient of log Doct/pH 7.4 of only 2.37-2.87, and has the ability to inhibit P-gp. According to Kandimalla. "the lipophilicity of (hydroxyzine), coupled with (its) ability to inhibit P-gp, enable(s) (it) to freely permeate across the olfactory mucosa." Because curcumin has an even lower molecular weight than hydroxyzine, has a significantly higher lipophilicity, and is able to lower both the function and expression of p-gp, it is reasonably concluded that curcumin should be able to pass through the olfactory mucosa and the blood brain barrier even easier than hydroxyzine.

Since curcumin (MW=368) and carbamazepine (MW=236) have similar molecular weights and are each highly lipophilic, the effects of intranasal carbamazepine upon carbamazepine brain concentration are highly instructive. Barakat, *J. Pharm. Pharmacol.,* 2006, January 58(1) 63-72 reports that peak brain tissue concentrations of carbamazepine attained by intranasal dosing (12 ug/g) were about four times higher than those attained by oral dosing:

| Route | Carbamazepine Dose (mg/kg) | Carbamazepine Peak Brain Tissue (ug/g) | ~uM |
|---|---|---|---|
| Intranasal | 0.2 | 12 | 48 |
| Intravenous | 8.0 | 4 | 16 |
| Oral | 16 | 3 | 12 |

Therefore, if curcumin enters the brain in molar amounts similar to carbamazepine (as is reasonably expected), then the resulting concentrations may be sufficient to both completely prevent toxic oligomer formation and effect Aβ metal binding. If even higher dosages of curcumin are used above 0.2 mg/kg, then the resultant brain tissue concentration would be expected to be even higher.

The dose of curcumin or compounds of Structural Formula (I) can be combined with a mucoadhesive to enhance its contact with the olfactory mucosa. In some embodiments, the mucoadhesive is selected from the group consisting of a hydrophilic polymer, a hydrogel and a thermoplastic polymer. Preferred hydrophilic polymers include cellulose-based polymers (such as methylcellulose, hydroxyethyl cellulose, hydroxy propyl methyl cellulose, sodium carboxy methyl cellulose), a carbomer chitosan and plant gum.

In some embodiments, the mucoadhesive is a water-soluble high molecular weight cellulose polymer. High molecular weight cellulose polymer refers to a cellulose polymer having an average molecular weight of at least about 25,000, preferably at least about 65,000, and more preferably at least about 85,000. The exact molecular weight cellulose polymer used will generally depend upon the desired release profile. For example, polymers having an average molecular weight of about 25,000 are useful in a controlled-release composition having a time release period of up to about 8 hours, while polymers having an average molecular weight of about 85,000 are useful in a controlled-release composition having a time released period of up to about 18 hours. Even higher molecular weight cellulose polymers are contemplated for use in compositions having longer release periods. For example, polymers having an average molecular weight of 180,000 or higher are useful in a controlled-release composition having a time release period of 20 hours or longer.

The controlled-release carrier layer preferably consists of a water-soluble cellulose polymer, preferably a high molecular weight cellulose polymer, selected from the group consisting of hydroxypropyl methyl cellulose (HPMC), hydroxyethyl cellulose (HEC), hydroxypropyl cellulose (HPC), carboxy methyl cellulose (CMC), and mixtures thereof. Of these, the most preferred water-soluble cellulose polymer is HPMC. Preferably the HPMC is a high molecular weight HPMC, with the specific molecular weight selected to provide the desired release profile.

The HPMC is preferably a high molecular weight HPMC, having an average molecular weight of at least about 25,000, more preferably at least about 65,000 and most preferably at least about 85,000. The HPMC preferably consists of fine particulates having a particle size such that not less than 80% of the HPMC particles pass through an 80 mesh screen. The HPMC can be included in an amount of from about 4 to about 24 wt %, preferably from about 6 to about 16 wt % and more preferably from about 8 to about 12 wt %, based upon total weight of the composition. Hydrogels can also be used to deliver the curcumin to the olfactory mucosa. A "hydrogel" is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or cross-linking. The hydrogels employed in this invention rapidly solidify to keep the curcumin at the application site, thereby eliminating undesired migration from the site. The hydrogels are also biocompatible, e.g., not toxic, to cells suspended in the hydrogel. A "hydrogel-inducer composition" is a suspension of a hydrogel containing desired curcumin. The hydrogel-inducer composition forms a uniform distribution of inducer with a well-defined and precisely controllable density. Moreover, the hydrogel can support very large densities of inducers. In addition, the hydrogel allows diffusion of nutrients and waste products to, and away from, the inducer, which promotes tissue growth.

Hydrogels suitable for use in the present invention include water-containing gels, i.e., polymers characterized by hydrophilicity and insolubility in water. See, for instance, "Hydrogels", pages 458-459 in *Concise Encyclopedia of Polymer Science and Engineering*, Eds. Mark et al., Wiley and Sons, 1990, the disclosure of which is incorporated herein by reference.

In a preferred embodiment, the hydrogel is a fine, powdery synthetic hydrogel. Suitable hydrogels exhibit an optimal combination of such properties as compatibility with the matrix polymer of choice, and biocompatibility. The hydrogel can include any of the following: polysaccharides, proteins, polyphosphazenes, poly(oxyethylene)-poly(oxypropylene) block polymers, poly(oxyethylene)-poly(oxypropylene) block polymers of ethylene diamine, poly (acrylic acids), poly(methacrylic acids), copolymers of acrylic acid and methacrylic acid, poly(vinyl acetate), and sulfonated polymers. Other preferred hydrogels include poly (acrylic acid co acrylamide) copolymer, carrageenan, sodium alginate, guar gum and modified guar gum.

In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly(phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

Preferred thermoplastic polymers include PVA, polyimide, polycarbonate, polyalkylene glycol, polyvinyl ether, polyvinyl ether, and polyvinyl halides, polymethacrylic acid, polymethylmethacrylic acid, methyl cellulose, hydroxypropyl cellulose, hydroxypropyl methylcellulose, and sodium carboxymethylcellulose, ethylene glycol copolymers.

Other polymers that may be suitable for use as a mucoadhesive include aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. For the purpose of this invention aliphatic polyesters include, but are not limited to, homopolymers and copolymers of lactide (which includes lactic acid, D-, L- and meso lactide), glycolide (including glycolic acid), $\epsilon$-caprolactone, $\rho$-dioxanone (1,4-dioxan-2-one), trimethylene carbonate (1,3-dioxin-2-one), alkyl derivatives of trimethylene carbonate, $\delta$-valerolactone, $\beta$-butyrolactone, $\chi$-butyrolactone, $\epsilon$-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, $\chi,\chi$-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly(iminocarbonates), for the purpose of this invention, are understood to include those polymers as described by Kemnitzer and Kohn, in the *Handbook of Biodegradable Polymers*, edited by Domb, et. al, Hardwood Academic Press, pp. 251-272 (1997). Copoly (ether-esters), for the purpose of this invention, are understood to include those copolyester-ethers as described in the *Journal of Biomaterials Research*, Vol. 22, pages 993-1009, 1988 by Cohn and Younes, and in *Polymer Preprints* (ACS Division of Polymer Chemistry), Vol. 30(1), page 498, 1989 by Cohn (e.g., PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer-based polymers made from L-lactide. D, L-lactide, lactic acid, glycolide, glycolic acid, para-dioxanone, trimethylene carbonate and $\epsilon$-caprolactone such as are described by Allcock in *The Encyclopedia of Polymer Science*, Vol. 13, pages 31-41, Wiley Intersciences, John Wiley & Sons, 1988 and by Vandorpe, et al. in the *Handbook of Biodegradable Polymers*, edited by Domb, et al, Hardwood Academic Press, pp. 161-182 (1997). Polyanhydrides include those derived from diacids of the form HOOC—C6H4-O—(CH2)$_m$—O—C6H4-COOH, where m is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859.150. Polyorthoesters such as those described by Heller in *Handbook of Biodegradable Polymers*, edited by Domb, et al, Hardwood Academic Press, pp. 99-118 (1997).

In some embodiments, the mucoadhesive is selected from the group consisting of poly(lactic acid) ("PLA") and poly (glycolic acid) ("PGA"), and copolymers thereof.

In some embodiments, the mucoadhesive formulation includes a penetration enhancer such as sodium glycocholate, sodium taurocholate, L-lysophosphotidyl choline, DMSO and a protease inhibitor.

In some embodiments, the curcumin or compounds of Structural Formula (I) is tagged with a molecule that binds specifically with the olfactory mucosa, such as an odorant.

In some embodiments, the pharmaceutical composition comprising curcumin or compounds of Structural Formula (I) includes a pharmaceutically-acceptable carrier, a lipophilic micelle, a liposome, or a combination thereof. Preferably, the lipophilic micelle or liposome comprises a ganglioside, a phosphatidylcholine, a phosphatidylserine, or a combination thereof.

In some embodiments, the pharmaceutical composition comprises a substance having an affinity for a receptor site on a neuron.

According to particular methods of intranasal delivery, it can be desirable to prolong the residence time of the pharmaceutical composition in the nasal cavity (e.g., in the olfactory region and/or in the sinus region), for example, to enhance absorption. Thus, the pharmaceutical composition can optionally be formulated with a bioadhesive polymer, a gum (e.g., xanthan gum), chitosan (e.g., highly purified cationic polysaccharide), pectin (or any carbohydrate that thickens like a gel or emulsifies when applied to nasal mucosa), a microsphere (e.g., starch, albumin, dextran, cyclodextrin), gelatin, a liposome, carbamer, polyvinyl alcohol, alginate, acacia, chitosans and/or cellulose (e.g., methyl or propyl; hydroxyl or carboxy: carboxymethyl or hydroxylpropyl), which are agents that enhance residence time in the nasal cavity. As a further approach, increasing the viscosity of the dosage formulation can also provide a means of prolonging contact of agent with olfactory epithelium. The pharmaceutical composition can be formulated as a nasal emulsion, ointment or gel, which offer advantages for local application because of their viscosity.

The pharmaceutical composition can also optionally include an absorption enhancer, such as an agent that inhibits enzyme activity, reduces mucous viscosity or elasticity, decreases mucociliary clearance effects, opens tight junctions, and/or solubilizes the active compound. Chemical enhancers are known in the art and include chelating agents (e.g. EDTA), fatty acids, bile acid salts, surfactants, and/or preservatives. Enhancers for penetration can be particularly useful when formulating compounds that exhibit poor membrane permeability, lack of lipophilicity, and/or are degraded by aminopeptidases. The concentration of the absorption enhancer in the pharmaceutical composition will vary depending upon the agent selected and the formulation.

To extend shelf life, preservatives can optionally be added to the pharmaceutical composition. Suitable preservatives include but are not limited to benzyl alcohol, parabens, thimerosal, chlorobutanol and benzalkonium chloride, and combinations of the foregoing. The concentration of the preservative will vary depending upon the preservative used, the compound being formulated, the formulation, and the like. In some representative embodiments, the preservative is present in an amount of 2% by weight or less.

The pharmaceutical composition can optionally contain an odorant, e.g. as described in EP 0 504 263 B1 to provide a sensation of odor, to aid in inhalation of the composition so as to promote delivery to the olfactory epithelium and/or to trigger transport by the olfactory neurons.

In some embodiments, the curcumin or compounds of Structural Formula (I) is delivered in a pharmaceutical composition selected from the group consisting of a liquid, a powder, a spray, a nose drop, a gel, an ointment, or a combination thereof.

In some embodiments, the curcumin or compounds of Structural Formula (I) is delivered in a pharmaceutical composition comprising piperine.

In some embodiments, the method of the present invention includes applying the pharmaceutical composition to an olfactory area in the upper third of the nasal cavity, such as the olfactory mucosa. In some embodiments, the method of the present invention includes applying the pharmaceutical composition to a roof of a nasal cavity. In some embodiments, the method of the present invention includes applying the pharmaceutical composition by employing a tube, a catheter, a syringe, a packtail, a pledget, a submucosal infusion, an intranasal spray container, or a combination thereof.

For delivery, there is provided a standard nose drops squeezable spray container with a long thin semi-flexible tube attached to the distal end. The outer diameter of the tube is less than a millimeter, preferably less than 0.5 mm, more preferably less than 0.25 mm. The exit hole of the tube is preferably located on the peripheral wall near the distal end of the tube so that spray exiting it can be directed upwards. There is a marker on the container that indicates when the exit hole is oriented upwards towards the cribriform plate.

Therefore, in accordance with the present invention, there is provided an intranasal spray device comprising:
 a) a hollow container having a first opening, and
 b) a flexible tube having a throughbore, a distal end portion having a second opening, and a proximal end having a third opening, and
 c) a formulation comprising an effective amount of curcumin or compounds of Structural Formula (I) contained within the container, wherein the third opening of the proximal end of the tube is in fluid connection with the first opening of the hollow container.

In other embodiments, the intranasal spray device comprises:
 a) a hollow container having a first opening,
 b) a flexible tube having a throughbore, a side surface having a second opening, a proximal end having a third opening, and a distal end having an end surface, and
 c) a formulation comprising an effective amount of curcumin or compounds of Structural Formula (I) contained within the container, wherein the third opening of the proximal end of the tube is in fluid connection with the first opening of the hollow container.

The user directs the tube towards the medial wall of the nostril and points upwards so as to direct it medially to and over the middle nasal concha. The length of the tube is predetermined so that when the user has the shoulder of the container flush against the nostril, the hole is adjacent the cribriform plate.

If there is concern about the safety of inserting a tube through a nasal passage, then the tube can also be balloon-like, so that it expands to full length upon being pressurized.

Delivery Through Anterior Nares

It has been reported that less than about 10% of inspired air travels through the olfactory slit. Accordingly, a great deal of the curcumin delivered to the nasal cavity does not region the olfactory mucosa. Therefore, it is an object of some embodiments of the present invention to increase the amount of curcumin or compounds of Structural Formula (I) delivered to the olfactory mucosa.

It has been reported in the literature that when the airflow in the nasal cavity can be characterized as laminar, streamlines from the anterior 10% of the nares reach the olfactory slit.

Accordingly, in some embodiments of the present invention, at least 25% of the formulation comprising curcumin or compounds of Structural Formula (I) is delivered into the anterior 10% of the nares. Preferably, at least 50% of the formulation comprising curcumin or compounds of Structural Formula (I) is delivered into the anterior 10% of the nares. More preferably, at least 75% of the formulation comprising curcumin or compounds of Structural Formula (I) is delivered into the anterior 10% of the nares.

In some embodiments, focused delivery of the formulation into the anterior portion of the nares is assisted by providing a guidance tube located substantially in the anterior 10% of the nares.

In some embodiments, there is provided a device for assisting delivery of a formulation to the anterior portion of the nares, comprising:
 a) an annulus adapted to fit in the opening of the nares and
 b) a guidance tube extending from the annulus and connected to the annulus in the region of the anterior 10% of the nares.

As the streamlines just inside the opening of the nares travel at an angle of about 90 degrees, the guidance tube is preferably situated at that angle in order to deliver the formulation into those streamlines. Preferably, the annulus is oval-shaped to correspond to the shape of the nares.

In use, the user simultaneously slowly inhales while actuating the spray container containing the formulation. The formulation is delivered to the anterior portion of the guidance tube as an aerosol in a laminar flow. The formulation travels through the guidance tube and exits is posterior end as an aerosol in a laminar flow. Thus, the formulation should enter the nasal cavity in conformance with the laminar streamlines of the inspired air produced by the inhalation. Once in these streamlines, the formulation travels preferentially to the olfactory slit and thus to the olfactory mucosa.

Helium

In some embodiments, the curcumin or compounds of Structural Formula (I) is delivered to the olfactory mucosa through helium-laden microbubbles that can rise in the air. This takes advantage of the fact that the olfactory mucosa is located in the highest portion of the nasal cavity. Theoretically, helium-filled microbubble of proper dimensions that are conventionally delivered into the nasal cavity should travel upwards to the highest spot in the nasal cavity—the olfactory mucosa. Once they are in place, the microbubbles can be exploded with a simple hand held, non-invasive ultrasound device, thereby releasing their contents. This invention would greatly increase the amount of curcumin or compounds of Structural Formula (I) that ends up in the olfactory mucosa.

Therefore, in accordance with the present invention, there is provided a method for transporting a neurotherapeutic drug to a brain of a mammal, comprising:

a) applying a plurality of microbubbles comprising the neurotherapeutic drug (preferably, curcumin), wherein the microbubbles are lighter than air (and preferably contain helium gas), to a nasal cavity of the mammal, whereby the microbubbles rise to an upper third of a nasal cavity of the mammal, whereupon the neurotherapeutic drug is absorbed through an olfactory mucosa and transported to the brain of the mammal.

In other embodiments, the curcumin or compounds of Structural Formula (I) is delivered to the olfactory mucosa as an aerosol in a bolus of helium gas that can rise in the air. This also takes advantage of the fact that the olfactory mucosa is located in the highest portion of the nasal cavity. Theoretically, a helium bolus and the aerosols therein that are conventionally delivered into the nasal cavity should travel en masse to the highest spot in the nasal cavity—the olfactory mucosa. Once they are in place, the aerosols can deposit upon the nasal walls containing the olfactory mucosa. This invention would greatly increase the amount of curcumin or compounds of Structural Formula (I) that ends up in the olfactory mucosa.

Therefore, in accordance with the present invention, there is provided a method for transporting a neurotherapeutic drug to a brain of a mammal, comprising:

a) providing a formulation comprising aerosol droplets of a neurotherapeutic drug (preferably, curcumin) in a bolus of helium gas, and b) applying the formulation to a nasal cavity of the mammal, whereby the formulation rises to an upper third of a nasal cavity of the mammal, whereupon the neurotherapeutic drug is absorbed through a nasal mucosa and transported to the brain of the mammal.

US Patent Publication No. 2003/0199594 ("Shah") discloses a propellant composition for use with an aerosol wherein the composition comprises between 70% and 100% helium, wherein the composition may be used in intranasal spray devices such as metered dose inhalers. Shah discloses that the composition may further include a solvent (such as an alcohol such as ethanol) and a dispersing agent (such as oleic acid).

Therefore, in accordance with the present invention, there is provided an intranasal spray device having a formulation comprising: a) an effective amount of curcumin. and b) a propellant comprising helium (preferably, at least about 70% helium by weight), and c) (optionally) a solvent (such as water or an alcohol such as ethanol), and d) (optionally) a dispersing agent (such as oleic acid).

Curcumin Prodrugs

Although high lipophilicity in a therapeutic compound enables it to easily cross the blood brain barrier and penetrate brain tissue, that high lipophilicity also usually means that the compound is not very soluble in water. For example, US 2003/0153512 reports that lipophilic curcumin has a solubility in water of only about 0.004 mg/ml. Because intranasal formulations are generally provided in small doses of between 50 μl and 200 μl (typically, 100 μl), there may be an issue in providing a sufficient amount of the lipophilic compound in a single dose in order to generate a therapeutic response.

Therefore, one aspect of the present invention involves providing the therapeutic compound in the form of a water-soluble prodrug. The high water solubility of the prodrug allows large amounts of it to be provided in a single dose, enter the nasal mucosa and passively diffuse across the nasal mucosa. Once the prodrug has reached the boundary of brain tissue, the prodrug is metabolized (typically through a chemical or enzymatic hydrolysis reaction with brain esterases) to the parent lipophilic molecule, whereby it can diffuse into the brain tissue bulk and provide a therapeutic benefit.

Therefore, in accordance with the present invention, there is provided a method for administering curcumin to a brain of a mammal, comprising:

a) applying a pharmaceutical composition comprising a water soluble curcumin prodrug to an upper third of a nasal cavity of the mammal, wherein the curcumin prodrug is absorbed through a nasal mucosa and transported to the brain of the mammal.

In some embodiments, the parent lipophilic compound is a phenol that is rendered water-soluble by creating an ester having an added polar moiety or a permanent charge. Preferably, the ester has a polar moiety. Preferably, the polar moiety contains a tertiary or quaternary nitrogen.

Therefore, in some embodiments, the ester contains an aminoalkanecarboxylic acid as the polar moiety. These compounds are characterized by an ester moiety having an alkane group between the nitrogen compound and the carboxyl group. Preferably, the moiety has terminal alkyl groups. More preferably, the aminoalkanecarboxylic acid contains a glycinate moiety, more preferably a methylated glycinate moiety, such as N, N, dimethylglycinate.

Therefore, in accordance with the present invention, there is provided a curcumin ester prodrug comprising an aminoalkylcarboxylic acid moeity. Preferably, the aminoalkylcarboxylic acid moiety comprises an aminoalkanecarboxylic acid moiety. In some embodiments, the aminoalkanecarboxylic acid contains a glycinate moiety. Methods of making such compounds are found in Pop, *Pharm. Res*., Vol. 13(1) 1996, 62-69.

Now referring to FIGS. 1A-1C, there are provided novel curcumin prodrugs of the present invention, labeled (1) to (30).

Therefore, in some embodiments, the aminoalkanecarboxylic acid moiety comprises a single terminal methyl group (1), two terminal methyl groups (2), (17), (20), or three terminal methyl groups (3)(19).

In some embodiments, the aminoalkanecarboxylic acid moiety comprises a single terminal ethyl group (5), two terminal ethyl groups (6)(18), or three terminal ethyl groups (8).

In some embodiments, the aminoalkanecarboxylic acid moiety comprises a terminal ethyl group and a terminal methyl group; a terminal ethyl group and two terminal methyl groups (10); or two terminal ethyl groups and a terminal methyl group (9).

In some embodiments, the aminoalkanecarboxylic acid moiety comprises a terminal propyl group.

In some embodiments, the prodrug is in the form of a salt, as in compounds (3), (8)-(14), (17)-(20). Preferably, the salt comprises an anion selected from the group consisting of chloride (14)(17)(18)(20), iodide (19) and bromide.

In some embodiments, the prodrug is characterized by an ester moiety in which an ethane (17-18) or propane (19-20) group lies between the carboxyl group and the nitrogen group, and preferably has a terminal alkyl group.

In some embodiments, the prodrug is characterized by an ester moiety in which the alkane that lies between the carboxyl group and the nitrogen group is substituted. In some embodiments, this is a terminal ethyl group (7) lying between the carboxyl group and the nitrogen group. Preferably, the moiety has a second terminal alkyl group.

In some embodiments, the curcumin prodrug comprises a carbamoyl moiety, preferably a (carboxymethyl)carbamoyl moiety (16). The (carboxymethyl)carbamoyl moiety of (16) can be made in substantial accordance with Mulholland, *Annals Oncology,* 12, 245-8(2001).

In some embodiments, the aminoalkanecarboxylic acid moiety comprises a nitrogen heterocycle (21, 23). In some embodiments, the heterocycle contain oxygen (23). Moeity (23) may be in accordance with the procedure disclosed in Pop, *Pharm. Res.,* 13, 3, 469-475 (1996) and Trapani, *Intl. J. Pharm.,* 175 (1998) 195-204. Moeity (21) may be may in accordance with the procedure disclosed in Trapani, *Intl. J.*

Pharm., 175 (1998) 195-204. Pop, Pharm. Res., 13, 3, 469-475 (1996) discloses that dexanabinol having a nitrogen heterocycle moiety like (21, 23) has a solubility of about 5-7 mg/ml.

In some embodiments, the aminoalkanecarboxylic acid moiety comprises a L-proline group (15). Moeity (15) may be may in accordance with the procedure disclosed in Altomare, Eur. J. Pharm. 20, 2003, 17-26 and Trapani, Intl. J. Pharm., 175 (1998) 195-204. Altomare reports that the L-proline ester of propofol provides the prodrug with a solubility of about 1.1 mmol/ml.

In some embodiments, the aminoalkanecarboxylic acid moiety comprises a benzoate group (22). Moeity (22) may be made in accordance with the procedure disclosed in Bundgaard, Pharm. Res., 8, 9, 1087-1093, (1991). Bundgaard discloses that providing a benzoate moeity (22) between the carboxyl and amino groups of a glycinate moiety raises the solubility of Acyclovir from 1.4 mg/ml to 3 mg/ml at a pH of about 7, and to about 300 mg/ml at a pH of about 5.

Other curcumin glycine esters are disclosed in Mishra, Bioorganic & Medicinal Chemistry, 13 (2005) 1477-86; Kumar, Nucleic Acids Symposium Series No. 44, 2000, pp. 75-76; Kapoor, Cancer Lett., 2007, Apr. 18, 248(2) 245-50; Tong, Anti-Cancer Drugs 17(3) 279-187 March 2006; and Mishra, Free Rad. Biology & Medicine, 38, (2005) 1353-1360

Desirable Prodrug Qualities

The curcumin prodrugs of the present invention should have three qualities: high solubility in water, high stability in water and rapid conversion to curcumin in the brain.

Solubility

The literature has demonstrated that glycinate-containing moieties provide much greater water solubility to phenolic compounds, typically increasing the solubility of the parent compound to the 25-50 mg/ml range. Examples of the solubility increase provided to low solubility phenolics by their esterification by glycinates are as follows:

TABLE I

| Parent Phenol | Parent solubility (mg/ml) | Ester solubility (mg/ml) | Reference |
| --- | --- | --- | --- |
| dexanabinol | 2-7 | ~50 | (a) |
| d-χ-tocopherol | — | ~25 | (b) |
| 17β-estradiol | 0.008 | 0.8-20 | (c) |
| testosterone | 0.01 | >100 | (d) |
| menahydroquinone | — | ~25 | (e) |
| phenol (+L-dopa) | — | 5 | (f) |

(a) Pop, J. Pharm Sci, 88, 11, 1999, 1156
(b) Takata, J. Lipid Res., 2002, 43, 2196
(c) Al-Ghananeem, AAPS PharmSciTech, 2002, 3.1, article 5
(d) Hussain, J. Pharm Sci., 91: 785-789, 2002.
(e) Takata, Pharm. Res., 21, 1, 1995, 18-23(solubility reported as 50 mM)
(f) Kao, Pharm. Res., 17, 8, 2000, 978-984

It further appears that pH has a great influence upon the solubility of nitrogen-containing esters of phenols. The influence of pH upon the solubility of nitrogen-containing esters of phenols as reported in the literature is presented below:

TABLE II

| Parent | Ester solubility at neutral pH (mg/ml) | Ester solubility at acidic pH (mg/ml) | Reference |
| --- | --- | --- | --- |
| Propofol | 0.064 | 4.67 | (a) |
|  | 0.735 | 6.920 | (a) |
| Acyclovir | 0.213 | 0.35 | (a) |
|  | 3 | 300 | (b) |

(a) Trapani. Intl. J. Pharm.. 175(1998) 195-204.
(b) Bundgaard, Pharm. Res.. 8, 9, 1087-1093, (1991).

The literature shows that, in most cases, providing the ester in an acidic pH (about 4-5) increases its solubility in water by about 10 fold.

There also appears to be a special class of glycinate-like moieties that increase the water solubility of the phenolic compound even further. In particular, there are a number of glycinate-like moieties possessing additional oxygens that increase the water solubility of the phenolic compound to concentrations in the 100-1000 mg/ml range. Examples of such compounds are provided below:

Examination of these compounds reveals that each is characterized by terminal substitution of the amine by oxygen-containing moeities. They are particularly characterized by:
 a) a (carboxymethyl) carbamoyl moiety (Mullholland, Ann. Oncology, 12, 245-248 (2001)),
 b) an N-acyloxymethyl moiety (Neilsen, Eur. J. Pharm. Sci., 2005. Apr. 24, 5, 433-40), or
 c) a (oxyalkyl)acetamide moiety (U.S. Pat. No. 5,073,641),
 d) glycine benzoates (WO90/08128)

Without wishing to be tied to a theory, it is believed that that these moieties may act as surfactants which, in the appropriate concentration, produce micelles. Indeed, it has been reported that a (dihydroxyethyl) glycinate moiety acts as a surfactant (U.S. Pat. No. 6,831,108), and that the (carboxymethyl) carbamoyl moiety can produce micelles (Shamsi, Electrophoresis, 2005, 26, 4138-52).

Therefore, in accordance with the present invention, there is provided a formulation comprising a micellar curcumin prodrug.

The (carboxymethyl) carbamoyl moiety (Mullholland) is of particular interest because is has a high solubility (>20 mg/ml). Its rapid hydrolysis in blood (tm=0.39 hr) may indicate that it is also rapidly hydrolyzed by brain esterases as well. Lastly, it appears to be relatively stable in water ($ty_2$=16.9 hr) and so likely is very stable in acidic aqueous solutions.

It has been reported that converting the prodrug into a salt likewise increases its solubility in water. For example, WO90/08128, which relates to glycine-like ester prodrugs, reports that conversion of such prodrugs into salts produce water solubilities of up to 15 w/v %. Jensen, Acta Pharm. Nord., 3, (1) 31-40 (1991) reports that a dichloride salt of one aminoalkylbenzoate ester was found to have a water solubility of greater than 40% v/v at 20° C. Lastly, U.S. Pat. No. 4,482,722 reports an addition salt of metrazole glycinate to have a water solubility of about 30%.

Stability

Because the formulations of the present invention are desirably used in the form of aqueous-based nasal sprays, the ester prodrugs of the present invention should remain stable in water for an appreciable time. It appears that glycinate esters are much more stable in acidic aqueous solutions than in neutral aqueous solutions. Al-Ghananeem, AAPS PharmSciTech, 2002, 3, 1, article 5, reports that the stability of phenol esters is influenced by pH, that at slightly acidic pHs (pH 3-5), one phenol ester (17-$DMABE_2HCl$) would have sufficient shelf life to be formulated in a solution dosage form, and that a pharmaceutical nasal spray solution of the prodrug at pH 4 would have a shelf life of approximately 19 months at 25° C. Similarly, Kao, *Pharm. Res.* 17, 8, 2000, 978-984 reports a maximum stability for the L-dopa butyl ester at a pH of 4.4, that the estimated time for 10% decomposition at pH 4.4, (0.05M phosphate buffer) and 10° C. is calculated to be 2.7 years, and that at slightly acidic pHs (pH 3-5), the ester would have sufficient shelf-life stability to be formulated in a solution dosage form. Lastly, PCT Published Patent Application WO90/08128, which relates to benzoate-containing glycine-like ester prodrugs, reports that one hydrocortisone-based prodrug possessed a shelf-life in aqueous solutions of pH 4.0 of 6.0 and 10.2 years at 25° C. and 20° C., respectively.

Therefore, in some embodiments of the present invention, the curcumin formulation contains a buffer setting a pH of between about 3.0 and 5.5, preferably a pH of between about 3.5 and 5, preferably a pH of between about 4 and 5. In some embodiments of the present invention, the curcumin formulation contains a buffer setting a pH of between about 3 and 4. It is believed that setting the pH of the formulation in these ranges would allow the formulations to have a commercially satisfactory shelf life.

Also in some embodiments of the present invention, there is provided an intranasal spray device comprising a formulation comprising:
 a) an effective amount of curcumin, and
 b) a buffering agent setting a pH of between 3 and 5.5.

Conversion Rate

Once the prodrug has reached the brain, it is desirable for the esterified prodrug to be converted to its parent compound in a very rapid fashion. Simply, the prodrug should be converted to the parent compound by brain esterases before it is drained from the brain. In order to understand whether a prodrug converts sufficiently rapidly to the parent compound, it is important to know the residence time of the prodrug in the brain or CSF (cerebrospinal fluid).

Review of concentration versus time profiles of intranasally instilled compounds reveals behaviors characterized by a two phase model. In the first phase, the drug rapidly attains a peak concentration and then rapidly decreases to about 10-25% of the peak concentration within about 1-2 hours. The second phase is characterized by a very slow decrease in the concentration of the drug over the next 24 hours.

Therefore, if the concentration of the drug is approximated as that which is present in the 1-2 hour range (i.e., about 10-25% of the peak concentration), it can be assumed that the drug is present in the brain for about 24 hours. Accordingly, in order to be useful, the conversion rate of the prodrug to the parent compound in the brain should be characterized by a half-life $t_{1/2}$ of no more than about 12 hours.

In at least three instances, the literature has reported conversion rates of a glycinate-containing phenolic ester to the parent compound by brain homogenate. Two of these papers report very rapid conversion. Al-Ghananeem, *AAPS PharmSciTech*, 2002, 3, 1, article 5, reports that the rapid conversion of estradiol glycinate esters to the parent estradiol in about 1-2 minutes. Kao, *Pharm. Res.*, 17, 8, 2000, 978-984 reports the rapid conversion of a benzyl L-dopa ester (wherein the L-dopa parent contains the glycinate moiety) in about 1 minute.

Since it is desirable to have a prodrug-to-parent conversion rate characterized by a half life of no more than about 12 hours, and the literature reports half-lives the rapid conversion of glycinate esters to the parent phenolic compound in about 1-2 minutes, it is clear that glycinate prodrugs should be assumed to be fully converted in the brain to the parent prodrug. It should be noted that one investigator (Trapani. *Intl. J. Pharm.*, 175 (1998) 195-204) reports a much slower conversion of propofol glycinate ester to the parent propofol. However, review of the pertinent structure-activity relationships indicates that the hydroxyl moiety of the propofol is severely sterically hindered by adjacent isopropyl groups of the propofol. Without wishing to be tied to a theory, it is believed that the severe steric hinderance of the etheric oxygen of these propofol glycinates is the reason for its slow conversion from the glycinate ester to propofol.

In contrast, the etheric oxygen of both benzyl L-dopa ester and the estradiol glycinate ester experiences much less streric hinderence, and so the brain esterase has an opportunity to freely approach the etheric oxygen from at least one side of the molecule. As a result, the hydrolysis reaction by brain esterases can occur much more quickly.

Undertaking a similar analysis with curcumin glycinate esters reveals that, like L-dopa and estradiol, the curcumin glycinate ester experiences much less streric hinderence, and so the brain esterases have the opportunity to freely approach the etheric oxygen of the curcumin glycinate ester from at least one side of the molecule.

Moreover, it appears that another research group reports a much faster conversion of the propofol dimethyl glycinate ester to the parent and that the Trapani group has acknowledged this difference. See Altomare, *Eur. J. Pharm. Sci.*, 20, 2003 17-26.

Lastly, the Kao paper is noteworthy in that it reports highly similar half-lives for the conversion of L-dopa esters to L-dopa in brain homogenate and plasma. A high coincidence of half-lives for the conversion of propofol glycinate esters to propofol in brain homogenate and plasma is also reported in Trapani. If conversion in plasma is used to reasonably estimate the conversion of glycinate esters in brain homogenate, then the literature may be further consulted for the conversion of glycinate-containing phenolic esters to the parent phenolic compound in plasma. The literature, reported below in Table III, reports the following:

TABLE III

| Parent Compound | Half-life of glycinate ester in plasma (min) | Reference |
| --- | --- | --- |
| Dexanabinol | 0-26 | (a) |
| Phenol (+L-dopa) | 0.36 | (b) |
| Acyclovir | 0.8 | (c) |
| Estradiol | 1-2 | (d) |
| Propofol | 24 hrs | (e) |
| Menahydroquinone | 13 | (f) |

(a) Pop J. Pharm. Sci., 88, 11, 1999, 1156
(b) Kao. Pharm. Res.. 17, 8, 2000, 978-984
(c) Bundgaard. Pharm. Res.. 8, 9, (1991) 1087-1093
(d) Al-Ghananeem, AAPS PharmSciTech. 2002, 3, 1, article 5
(e) Trapani. Intl. J. Pharm.. 175(1998) 195-204
(f) Takata. Pharm. Res.. 21.1.1995. 18-23

Thus, using literature reports of conversion in plasma to estimate reasonably the likely conversion window of glycinate esters in brain homogenate, it appears that the conversion of glycinate-containing phenolic esters to the parent phenolic compound in brain is again quite rapid.

Therefore, because unhindered phenolic glycinate esters rapidly convert to the parent phenol in brain homogenate, and because dimethylglycinate phenolic esters convert rapidly in plasma, it is believed that the conversion rates of glycinate-containing curcumin esters to the parent curcumin compound will be rapid in a brain environment.

How to Make Prodrugs

Al-Ghananeem, *AAPS PharmSciTech,* 2002, 3, 1, article 5, teaches how to make an ester comprising the following amino-alkane-carboxylic acid moieties: 3-N,N dimethylamino butyl ester HCl (3-DMABE$_2$HCl); 3-N,N-diethylamino propionyl ester hydrochloride (DEAPE$_2$HCl); 3-N,N,N-trimethylamino butyl ester iodide (3-TMABE$_2$ iodide) and 17-N,N dimethylamino butyl ester HCl (17-DMABE$_2$HCl);

In some embodiments, the water-soluble ester prodrug of curcumin or compounds of Structural Formula (I) is created by reacting the phenolic parent compound with dimethylglycine. The literature reports rendering lipophilic phenolic compounds water soluble by reacting the phenolic parent compound with dimethylglycine. For example, Al-Ghananeem, *AAPS PharmSciTech,* 2002, 3, 1, article 5, reports increasing the water solubility of 17B-estradiol from 0.008 mg/ml to 0.8 mg/ml (a 100-fold increase) by creating a dimethylglycine ester of the parent compound. Al-Ghananeem further found that this ester was readily hydrolyzed by rat brain homogenate to provide the parent compound, and that intranasal administration of the prodrug provided a 5-8 fold higher CSF concentration of 17B-estradiol when compared with a comparable intravenous dose of the prodrug. Al-Ghananeem concluded that the prodrug provides for targeted intranasal delivery of 17B-estradiol to the brain.

In some embodiments, creation of the water soluble ester prodrug from the parent phenolic compound is carried in substantial accordance with the method described in Hussain, *J. Pharm. Sci.,* 91, 3, March 2002, 785-789. In particular, dimethylglycine HCl and oxalyl chloride are gently warmed at 40° C. until evolution of HCl gas ceases. Nitrogen gas is then bubbled through the solution to remove unreacted oxalyl chloride. The resulting acid chloride is dissolved in dimethylformamide and added dropwise with stirring to a solution of the parent phenolic compound in methylene chloride. The reaction mixture is refluxed for 3 hours. The ester is then isolated, and converted to an HCl salt.

In some embodiments, creation of the water soluble ester prodrug from the parent compound is carried in substantial accordance with the method described in Al-Ghananeem, *AAPS PharmSciTech,* 2002, 3, 1, article 5. In particular, 4-(dimethylamine) butyric acid hydrochloride (2.0 g, 0.012 mol) or 3-(dimethylamine) proprionic acid hydrochloride (2.2 g, 0.012 mol) is used as a starting material. The amino acid is refluxed gently with oxalyl chloride (1.6 mL, 0.018 mol) for a short period of time until a clear yellow solution is formed. The solution mixture is then flushed very gently with a stream of nitrogen to remove excess oxalyl chloride leaving a solid behind (the acid chloride).

The phenolic esters having 3-N,N-dimethylamino butyl ester hydrochloride (3-DMABE$_2$HCl); 3-N,N-dimethylamino propionyl ester hydrochloride (3-DEAPE$_2$HCl); and 3-N,N,N-trimethylamino butyl ester iodide (3-TMABE$_2$ iodide) as moieties are synthesized after the appropriate acid chloride following the procedure reported in Hussian, *Pharm. Res.,* 1988, 5, 1, 44-47. The alcoholic ester, 17-N,N-dimethylamino butyl ester hydrochloride (17-DMABE$_2$HCl) is prepared by dissolving the acid chloride slowly in 10 mL N$_5$N, dimethylformamide (DMF) while in an ice bath since the reaction is exothermic. The parent phenolic compound is then dissolved in methylene chloride, and the DMF solution of acid chloride is added dropwise to the solution of the parent phenolic compound with stirring. The reaction mixture is refluxed gently for 45 minutes, then filtered. The filtrate is evaporated using a Buchi model rotavaporator (Westbury, N.Y.) then redissolved in a small volume of 80 CHC13: 20 MeOH. The content of the mixture is separated and purified using a silica gel column. The solvent mixture is evaporated and the product redissolved in a small volume of methylene chloride, then hydrogen chloride gas is carefully bubbled through the solution with stirring. The ester hydrochloride is precipitated by adding enough diethyl ether to make the solution turbid and then the mixture is placed in a refrigerator at 4° C. overnight. The final product is collected by solvent evaporation in a vacuum dessicator using a Precision Scientific model D75 pump (Chicago, Ill.) at room temperature and stored in a desiccator until used.

In some embodiments, creation of the water soluble ester prodrug from the parent compound is carried in substantial accordance with the method described in Takata, *J. Lipid Res.,* 2002, 43, 2196-2204. In particular, to a dry pyridine solution of the parent phenolic compound (4.8 mmol), 5.7 mol of N,N,-dimethylglycine HCl and 5.7 mmol of dicyclohexylcarbodiimide are added. The reaction mixture is stirred at room temperature for 20 hours and the dicyclohexylurea formed is removed by filtration. After the solvent is evaporated, the residue is treated with 100 ml of water and made alkaline by sodium bicarbonate. The solution is then extracted with ethyl acetate (100 ml×3). The organic layer is dried over anhydrous sodium sulfate with ethyl acetate and evaporated. The residue is fractionated with a flash column packed Wakogel LP40, 60A using n-hexane ethyl acetate (8:2, v/v) as the eluent. The isolated ester is directly collected in isopropyl ether containing 3% HCl dioxane solution, and the precipitate and recrystallized from acetone to give the HCl salt of the parent phenolic compound.

Brain Levels

Evidence that the intranasal installation of a water soluble prodrug of curcumin can deliver high levels of curcumin to the brain is found in the estradiol-based work of Al-Ghananeem, *AAPS PharmSciTech.* 2002, 3, 1, article 5, 17β-Estradiol is a 272 dalton phenol having a octanol/water partition coefficient of about log P=3.1–4.0. Therefore, estradiol is similar to curcumin in that each is a lipophilic, phenolic small molecule. Also, like curcumin. 17β-estradiol also suffers from poor bioavailability. Moreover. Al-Ghananeem reports that estradiol is not very soluble in water, thereby making impractical the nasal administration of an effective dose (0.1 mg in 0.1 ml). Al-Ghananeem reports modifying estradiol with a dimethylglycinate moiety to increase the water solubility of estradiol from 0.008 mg/ml to about 0.8 mg/ml—a 100-fold increase, and modifying estradiol with a 3-DEAPE$_2$HCl moiety to increase the water solubility of estradiol from 0.008 mg/ml to about 20 mg/ml—over a 1000 fold increase. Thus, the solubility of a lipophilic, phenolic small molecule like curcumin, which has a solubility in water of only about 0.004 mg/ml, can be greatly increased.

Because the typical volume of an intranasal dose for a human can be up to 0.2 ml, and Table I above reports increases in solubility in the range of 20 mg/ml, nasal administration can be expected to achieve a payload of up to about 20 mg/mix 0.2 ml=4 mg/dose. Because providing two doses per nostril twice a day provides 8 doses per day, it is believed that up to about 32 mg/day of estradiol can be intranasally administered. This amount provides a whole body concentration of nearly about 0.5 mg/kg.

Further, Al-Ghananeem reports that the nasal installation of 0 1 mg/kg of water soluble prodrugs of 17β-Estradiol results in peak cerebrospinal fluid (CSF) concentrations of estradiol of between about 30 ng/ml (for 17-DMABE$_2$-HCl) to about 66 ng/ml (for 3-DMABE$_2$-HCl), which provides a molar concentration of the compound of between about 0.075 μM and 0.15 μM. The pharmacokinetic results of Al-Ghananeem correspond quite well with those of Kao, who reported that nasal installation of 20 mg/kg of water soluble ester prodrug of L-dopa results in peak cerebrospinal fluid (CSF) concentration of about 10-20 ug/ml. Accordingly, a 0.5 mg/kg nasal instillation of a water soluble prodrug of a lipophilic, small molecule phenolic compound such as estradiol or curcumin can likely provide CSF concentrations of up to about 0.75 μM. Since it has been reported that 0.1-1.0 μM curcumin inhibits the in vitro formation of amyloid beta oligomers, and blocks the in vitro toxicity of $A\beta_{1\_42}$ oligomers in differentiated neuroblastoma cells (Yang, *J. Biol. Chem.*, 280.7, Feb. 18, 2005, 5892-5901), it appears that the intranasal installation of a water soluble prodrug of curcumin will likely allow an attainable dosing schedule to attain a brain concentrations of curcumin that will provide a therapeutic benefit against Alzheimer's Disease.

Dual Phase Composition

In some embodiments, curcumin or compounds of Structural Formula (I) is present within two separate phases of the formulation. The first phase is preferably a quick release phase that quickly delivers curcumin or compounds of Structural Formula (I) to the olfactory mucosa. The quick delivery of curcumin or compounds of Structural Formula (I) will have the effect of transiently disabling enzymes systems such as UGTs and P450s that metabolize curcumin. The second phase is a slow release phase that slowly delivers curcumin or compounds of Structural Formula (I) to the olfactory mucosa. Once these enzyme systems are transiently disabled, the slow release phase slowly releases curcumin or compounds of Structural Formula (I) in an environment that is substantially free of enzymatic metabolic interference.

Therefore, in accordance with the present invention, there is provide a formulation comprising:
 a) a first, quick release phase comprising an effective amount of curcumin or compounds of Structural Formula (I) for transiently disabling enzyme systems, and
 b) a second slow release phase comprising an effective amount of curcumin or compounds of Structural Formula (I) for treating a neurodegenerative disease, or other disease or disorder disclosed herein.

In some embodiments, the first quick release phase can be selected from the group consisting of a mucoadhesive and an oil, such as peppermint oil. Peppermint oil has the quality of independently inhibiting UGT and P450 enzymes.

In some embodiments, the second slow release phase can be selected from the group consisting of liposomes and thermoplastic polymers (such as PLGA).

In accordance with the present invention, there is provided a formulation comprising:
 a) a polymeric particulate depot comprising curcumin or compounds of Structural Formula (I), and
 b) a mucoadhesive.

In some embodiments, the mucoadhesive is present as a coating upon the polymeric particulate depot.

In some embodiments, the mucoadhesive is present as a separate particulate.

In some embodiments, the mucoadhesive comprises a compound selected from the group consisting of a chitosan and a cellulose.

In some embodiments, the mucoadhesive further contains curcumin or compounds of Structural Formula (I).

In some embodiments, the polymeric particulate depot is a liposome.

In some embodiments, the polymeric particulate depot is a thermoplastic bioresorbable polymer.

In some embodiments, the curcumin or compounds of Structural Formula (I) is housed in microspheres. Kumar, *Indian J. Physiol. Pharmacol.*, 2002 April 46(2) 209-17 reports that when curcumin was loaded into either albumin or chitosan microspheres, a biphasic release pattern occurred, characterize by a burst effect followed by a slow release. This biphasic effect corresponds well with the stated desire to have a first dose of curcumin released in order to inhibit enzyme activity in the olfactory mucosa followed by a second dose that is slowly released, taken up by the olfactory neurons and transported to the brain.

In some embodiments, the curcumin or compounds of Structural Formula (I) is housed in microspheres that display a biphasic release effect.

Enzyme Inhibition by Curcumin

Although curcumin is susceptible to metabolism by enzymes, curcumin is also known as an inhibitor of those very enzymes. For example. Hong, *Biochem. Biophys. Res. Comm.*, 2003. Oct. 10, 310(1) 222-7, reports that co-treatment by curcumin of EGCG in cells transfected with hPgP, hMRPI and hMRP2 genes increased the accumulation of EGCG in those cells.

It has been reported that curcumin influences both multidrug, resistance protein 1 (MRPI) multidrug resistance protein 2 (MRP2). It appears that curcumin inhibited both MRP-1 and MRP-2-mediated transport with IC50 values of 15 uM and 5 uM. Wortelboer, *Chem. Res. Toxicol.*, 2003 Dec. 16:12, 1642-51. Wortelboer also recognized the "complex interplay between MRP inhibition and metabolism of MRP inhibitors. Chearwae, *Cancer Chemother. Pharmacol.*, 2006, February 57(3) 376-88 reports curcumin to inhibit MRP1, with an IC50 of about 14.5 uM.

Of note, Hong, *Biochem. Biophys. Res. Comm.* 2003 Oct. 10, 310(1) 222-7 reports that the inhibition of MRPs by curcumin led to a significant increase in the amount of green tea catechin EGCG in MDCKII/MRPI and HT-29 cells. Therefore, there is a special advantage in providing both curcumin and EGCG in the same formulation, as curcumin can provide therapeutic benefits and increase the bioavailability of EGCG.

It appears that curcumin is metabolized mainly through glucuronidation. Pan, *Drug Metab. Dispos.*, 1999, 27, 1, 486-494. However, it has been repeatedly demonstrated that curcumin also inhibits glucuronidation. Basu, *Drug. Metab. Dispos.*, 2004, Jul. 32(7) 768-73 reports that curcumin transiently inhibits MPA glucuronidation in both human LS 180 colon cells and mouse duodenum. Basu, *PNAS*, May 3, 2005, 102(18) 6285-90 reports the inhibition of cellular UGT1a7 and UGT1A1O activities after exposure to curcumin. Basu, *J. Biol. Chem.*, 279, Jan. 9, 2004, 1429-1441 reports that curcumin reversible targets UGTs causing inhibition. In general, curcumin appears to provide its maximum inhibition of UGT activity about 1-2 hours after exposure. Basu, *Biochem. Biophys. Res. Comm.*, 303 (2003) 98-104 (FIG. 1) reports that the inhibition of UGT1A1 by curcumin can reach about 95% after about one hour after exposure, returning to about 80% of the control value after about 10 hours. Naganuma, *Biol. Pharm. Bull.* 2006 Jul. 29(7) 1476-9 reports the moderate inhibition of UGT activity in the conjugation of 1-naphthol in Caco-2 cells by curcumin.

Because of the strong inhibition of UGTs by curcumin, curcumin has been proposed as a pre-treatment for cancer chemotherapy, and it has been reported that transient inhibition of glucuronidation by oral pretreatment with curcumin before MPA administration caused a six-fold increase in immunosuppression of antigen-stimulated spleen cytotoxic T-lymphocyte proliferation in mice. See (http://iiichddirsagc.nJchd.nih.gov:S08Q/ar2004/pagcs/hdb/sgddm.htm).

There is, however, one investigator (van der Logt, *Carcinogenesis*, 24, 10, 1651-56, 2003) that reports enhancement of UGT activity by curcumin.

Because the glucuronidation inhibition by curcumin is reversible, it appears that curcumin could be used for a pre-treatment of the olfactory mucosa in order to inhibition enzymatic activity upon the later therapeutic dose of curcumin without a concern for drug-drug interactions.

Therefore, in some embodiments, a first dose of curcumin or compounds of Structural Formula (I) is intranasally administered to the patient (to inhibit enzyme activity in the olfactory mucosa, and then a second dose of curcumin or compounds of Structural Formula (I) is intranasally administered to the patient at least about 15 minutes after the first dose (to travel to the brain).

It is well known that that the cytochrome p450 enzymes are significant in the olfactory mucosa. Oetari, *Biochem. Pharmacol.*, 1996, Jan. 12, 51(1) 39-45 reports that curcumin strongly inhibits P450s in rat liver. Thapliyal, *Food Chem. Toxicol.* 2001, June 39(6) 541-7 reported the inhibition of cytochrome P450 isoenzymes by curcumins both in vitro and in vivo. Zhou, *Drug Metab. Rev.*, 2004 February 36(1) 57-104 reports curcumin to be an inhibitor of Pgp.

In certain embodiments, a glucuronidation inhibitor is used in combination with curcumins or compounds represented by Structural Formula (I). In one embodiment, the glucuronidation inhibitor is administered prior to curcumins or compounds represented by Structural Formula (I). In another embodiment, the glucuronidation inhibitor is administered after curcumins or compounds represented by Structural Formula (I). In another embodiment, the glucuronidation inhibitor is administered at the same time with curcumins or compounds represented by Structural Formula (I).

In some embodiments, piperine is used as a glucuronidation inhibitor. Reen, *Biochem. Pharmacol.*, 1993, Jul. 20, 46(2) 229-38 reports piperine to be a potent inhibitor of glucuronidation. Shoba, *Planta Med.*, 1998 May 64(4) 353-6 reports that pre-administration of piperine led to a 2000% increase in the bioavailability of curcumin in humans.

In some embodiments, the glucuronidation inhibitor is an analog of piperine. Preferably, the piperine analog is antiepilepsirine. Administration of antiepilepsirine is also effective in raising serotonin synthesis (Liu, *Biochem. Pharmacol.*, 1984 December 1, 33(23) 3883-6), and has been studied as an antiepilepsy drug (Wang, *Brain Dev.* 1999 Jan. 21(1) 36-40). Accordingly, its intranasal administration should not lead to significant problems.

In some embodiments, the glucuronidation inhibitor is a surfactant. Kurkela, *J. Biol. Chem.*, 2003 Feb. 7, 278(6) 3536-44 reports that several UGT enzymes were nearly fully inhibited by a surfactant, namely Triton X-100. Preferably, the surfactant is a non-ionic surfactant.

In some embodiments, the glucuronidation inhibitor is a mucolytic agent, such as N-acetylcysteine (NAC). Takatsuka, *Int. J. Pharm.*, 2006 June 19, 316(1-2) 124-30, reports that co-administration of a mucolytic agent (NAC) and a surfactant (Triton TX-100) led to enhanced intestinal absorption in a synergistic manner. It was further reported that the damage to the mucosa was reversible.

In some embodiments, the glucuronidation inhibitor is an NSAID. In preferred embodiments, the NSAID is niflumic acid. Mano, *Biopharm. Drug Dispos.*, 2006 January, 27(1) 1-6 reports the inhibitory effect of NSAIDs, and niflumic acid in particular, on UGT activity.

Enzyme Inhibition by Buffer

In some embodiments, low pH buffers are used as glucuronidation inhibitors. Basu, *PNAS*, May 3, 2005, 102, 18, 6285-90 reports maximum glucuronidation of lipophiles by UGT1A7 in the pH range of 6-9, and nearly zero glucuronidation activity by UGT1A7 at pH 5. Similarly, Basu, *J. Biol. Chem.*, 279, Jan. 9, 2004, 1429-1441 reports that pH can drastically alter the level of UGT activity, and that a pH of 5 inhibits nearly all glucuronidation activity for each of UGT1 A7 and UGT1A1O. Therefore, it appears that low pH formulations are effective in completely inhibiting glucuronidation activity.

In some embodiments of the present invention, the curcumin formulation or a formulation of compounds represented by Structural Formula (I) contains a buffer setting a pH of between about 3.0 and 5.5, preferably a pH of between about 3.5 and 5, preferably a pH of between about 4 and 5. In some embodiments of the present invention, the curcumin formulation or a formulation of compounds represented by Structural Formula (I) contains a buffer setting a pH of between about 3 and 4. Below these cited ranges, there is a chance that the acidic nature of the formulation will be irritating to the nasal cavity. Above this range, there may be minimal inhibition of glucronidation. U.S. Pat. No. 6,187,332 ("Gern") discloses a buffered flowable nasal spray formulation having a pH of between 4 and 5 which is able to maintain its pH for prolonged periods in the human nose. Gem discloses formulation comprising citrate and phosphate buffering agents.

Therefore, in accordance with the present invention, there is provided an intranasal spray device comprising a formulation comprising:
  a) an effective amount of curcumin or a formulation of compounds represented by Structural Formula (I), and
  b) a buffering, agent (preferably, a citrate or phosphate) having a pH of between 4 and 5 which is able to maintain the pH of the formulation between 4 and 5 in the human nose for prolonged periods.

Absorption Enhancers

In some embodiments, the absorption enhancer is a bile salt. Chavanpatil, *Pharmazie*, 2005 May, 60(5) 347-9. In preferred embodiments, the bile salt is selected from the group consisting of sodium deoxycholate, sodium caprate, and sodium tauroglycocholate and EDTA.

In some embodiments, magnesium$^{+2}$ is used as a glucuronidation inhibitor. Wong, *Biochem. J.*, (1968) 110.99 reports that $Mg^{+2}$ concentrations in excess of about 10 mM were effective in inhibiting about 85% of enzymatic glucuronidation activity.

Cooling

The UGT enzyme is likely very sensitive to temperature. Therefore, it is reasonable to expect that a decrease in the temperature of the mucosal lining will result in a decrease in the enzymatic glucuronidation of curcumin by the UGTs. Indeed, it has been reported by Castuma, *Biochem. J.*, (1989) 258, 723-731 that the enzymatic activity of UDP-glucuronyltransferase in normal liver microsomes of guinea pigs decreased about 3-fold when the temperature of the microsomes was reduced from about 37° C. to about 10° C.

Therefore, the present invention also includes embodiments based upon the temporary cooling of the nasal mucosa in order to inhibit the glucuronidation of curcumin or compounds of Structural Formula (I).

In one embodiment, the formulation of the present invention contains a cooling agent such as menthol.

In one embodiment, the formulation of the present invention contains an endothermic solute. In preferred embodiments, the endothermic solute is a strong salt, acid or base that dissolves in water by an endothermic process. More preferably, the endothermic solute is a salt.

In some embodiments, the endothermic solute may be selected from the group consisting of sodium bicarbonate ($\Delta H=+19.1$ kJ/mol); potassium bicarbonate ($\Delta H=+5.3$ kcal/mol); potassium sulfate ($\Delta H=+23.7$ kJ/mol); potassium chloride ($\Delta H=+17.2$ kJ/mol); sodium chloride ($\Delta H=+3.9$ kJ/mol); and potassium dihydrogenphosphate ($\Delta H=+19.6$ kJ/mol).

In some embodiments, the endothermic solute may be magnesium sulfate, which would both promote cooling and inhibition glucuronidation.

Therefore, in accordance with the present invention, there is provided an intranasal spray device comprising a formulation comprising:
 a) an effective amount of curcumin or a compound represented by Structural Formula (I), and
 b) an endothermic solute (preferably magnesium sulfate).

It is well known that curcumin is poorly soluble in water. Because the olfactory mucosa is aqueous-based, the transport of curcumin from the formulation across the olfactory mucosa is problematic.

Therefore, in order to increase the transport of curcumin across the olfactory mucosa, in some embodiments, the curcumin is delivered in a formulation comprising an effective amount of a curcumin-miscible solvent. Preferably, the solvent is selected from the group consisting of dimethyl sulfoxide (DMSO) and ethanol. It is well known that curcumin is highly soluble in DMSO and ethanol. When this formulation is applied to the nasal mucosa, the solvent mixes with the water in the olfactory mucosa and renders curcumin soluble in that mixture.

In preferred embodiments, the solvent is DMSO. DMSO is non-toxic and also can temporarily open the blood brain barrier. Kleindienst, *Acta Neurochir. Suppl.* 2006; 96, 258-62, and Scheld, *Rev. Infect. Pis.,* 1989 November-December; 11 Suppl 7; S1669-90.

Therefore, in accordance with the present invention, there is provided an intranasal spray device comprising a formulation comprising:
 a) an effective amount of curcumin or a compound represented by Structural Formula (I), and
 b) a solvent selected from the group consisting of DMSO and ethanol.

Increasing Solubility

Some embodiments increase the solubility of curcumin or compounds represented by Structural Formula (I) in water by employing a solid dispersion, such as those made with polyethylene glycol 6000 (PEG 6000) or polyvinylpyrrolidone K-30 (PVP K30). Ruan, *J. Pharm Biomed. Anal.* 2005 July 1; 38(3):457-64. Paradkar, *Int. J. Pharm.* 2004 Mar. 1; 271(1-2):281-6.

Some embodiments increase the solubility of curcumin or compounds represented by Structural Formula (I) in water by employing inclusion complexes, such as those made with beta-cyclodextrin (BCD) and hydroxypropyl-beta-cyclodextrin (HPBCD). Ruan, *Pharm Biomed Anal.* 2005 July 38(3): 457-64.

Other Curcumin Analogs

Modifications of curcumin and its functional fragments that either enhance or do not greatly affect the ability to treat AD, cancer, or other disorders described herein are also included within the term "curcumin." Such modifications include, for example, additions, deletions or replacements of one or more functional groups. These modifications will either enhance or not significantly alter the structure, conformation or functional activity of curcumin or a functional fragment thereof. Additionally, curcumin or its functional fragments can be modified by the addition of epitope tags or other sequences that aid in its purification and which do not greatly affect its activity. As used herein, the term "functional fragment," in connection with an curcumin, is intended to mean any portion of curcumin that maintains its ability to inhibit oxidation, or to prevent beta amyloid oligomer formation. If desired, a functional fragment can include regions of the curcumin with activities that beneficially cooperate with the ability to inhibit oxidation or oligomer formation.

Also in accordance with the present invention, publicly known analogs of curcumin may be used.

In some embodiments, the curcumin analogs are those found in US Published patent application US 2006/0067998.

Curcumin is soluble in ethanol, alkalis, ketones, acetic acid and chloroform. It is insoluble in water. Curcumin is therefore lipophilic, and generally readily associates with lipids, e.g., many of those used in the colloidal drug-delivery systems of the present invention. In certain embodiments, curcumin can also be formulated as a metal chelate.

As used herein, curcumin analogues are those compounds which clue to their structural similarity to curcumin, exhibit anti-proliferative or pro-apoptotic effects on cancer cells similar to that of curcumin. Curcumin analogues which may have anti-cancer effects similar to curcumin include Ar-tumerone, methylcurcumin, demethoxy curcumin, bis-demethoxycurcumin, sodium curcuminate, dibenzoyl-methane, acetylcurcumin, feruloyl methane, tetrahydrocurcumin, 1,7-bis(4-hydroxy-3-methoxyphenyl)-1,6-heptadiene-3,5-dione (curcuminl), 1,7-bis(piperonyl)-1,6-heptadiene-3,5-dione(piperonyl curcumin) 1,7-bis(2-hydroxy naphthyl)-1,6-heptadiene-2,5-dione(2-hydroxyl naphthyl curcumin), 1,1-bis(phenyl)-1,3,8,10-undecatetraene-5,7-dione (cinnamyl curcumin) and the like (Araujo and Leon, 2001; Lin et al., 2001; John et al, 2002; see also Ishida et al., 2002). Curcumin analogues may also include isomers of curcumin, such as the (Z,E) and (Z,Z) isomers of curcumin. In a related embodiment, curcumin metabolites which have anti-cancer effects similar to curcumin can also be used in the present invention. Known curcumin metabolites include glucoronides of tetrahydrocurcumin and hexahydrocurcumin, and dihydroferulic acid. In certain embodiments, curcumin analogues or metabolites can be formulated as metal chelates, especially copper chelates. Other appropriate derivatives of curcumin, curcumin analogues and curcumin metabolites appropriate for use in the present invention will be apparent to one of skill in the art.

In some embodiments, the curcumin analogs are those found in US Published patent application US 2005/0181036.

Commercial curcumin includes three major components: curcumin (77%), demethoxycurcumin (17%), and bis-demethoxycurcumin (3%), which are often referred to as "curcuminoids." As used herein. "curcumin" is defined to include any one or more of these three major components of commercial curcumin, and any active derivative of these agents. This includes natural and synthetic derivatives of curcumin and curcuminoids, and includes any combination of more than one curcumenoid or derivative of curcumin. Derivatives of curcumin and curcumenoids include those derivatives disclosed in U.S. Patent Application Publication 20020019382, which is herein specifically incorporated by reference.

In some embodiments, the curcumin analogs are those found in US Published patent application US 2005/0267221.

In certain aspects, 1,7,-bis(4-hydroxy-3-methoxyphenyl)-1,6-heptadi-ene-3,5-diose is the curcumin that may be used in the present invention. Other curcumin analogues (curcuminoids) that may be used include, for example, demethoxycurcumin, bisdemethoxycurcumin, dihydrocurcumin, tetrahydrocurcumin, hexahydrocurcumin, dihydroxytetrahydrocurcumin, Yakuchinone A and Yakuchinone B, and their salts, oxidants, reductants, glycosides and esters thereof. Such analogues are described in U.S. Patent Application 20030147979; and U.S. Pat. No. 5,891,924 both of which are incorporated in their entirety herein by reference.

Other curcumin analogues (curcuminoids) that may be used include dihydroxycurcumin and nordihydroguaiaretic acid (NDGA)

Further examples of curcumin analogues include but are not limited to (a) ferulic acid, (i.e., 4-hydroxy-3-methoxycinnamic acid; 3,4-methylenedioxy cinnamic acid; and 3,4-dimethoxycinnamic acid); (b) aromatic ketones (i.e., 4-(4-hydroxy-3-methoxyphenyl)-3-buten-2-one; zingerone; -4-(3,4-methylenedioxyphenyl)-2-butanone; 4-(p-hydroxyphenyl)-3-buten-2-one; 4-hydroxyvalerophenone; 4-hydroxybenzylactone; 4-hydroxybenzophenone; 1,5-bis(4-dimethylaminophen-yl)-1,4-pentadien-3-one); (c) aromatic diketones (i.e., 6-hydroxydibenzoylmethane); (d) caffeic acid compounds (i.e. 3,4-dihydroxy cinnamic acid); (e) cinnamic acid; (f) aromatic carboxylic acids (i.e., 3,4-dihydroxyhydrocinnainic acid; 2-hydroxycinnamic acid; 3-hydroxy cinnamic acid and A-hydroxycinnamic acid); (g) aromatic ketocarboxylic acids (i.e., 4-hydroxyphenylpyruvic acid); and (h) aromatic alcohols (i.e., 4-hydroxyphenethyl alcohol). These analogues and other representative analogues that can be used in the present invention are further described in WO9518606 and WO 01040188, which are incorporated herein by reference in their entirety.

Curcumin or analogues thereof may be purified from plants or chemically synthesized using methods well known and used by those of skill in the art. Plant-derived curcumin and/or its analogues can be obtained by extraction from plants including Zingiberaceae *Curcuma*, such as *Curcuma longa* (turmeric). *Curcuma aromatica* (wild turmeric), *Curcuma zedoaria* (zedoary), *Curcuma xanthorrhiza*, mango ginger, Indonesian arrowroot, yellow zedoary, black zedoary and galangal. Methods for isolating curcuminoids from turmeric are well known in the art (Janaki and Bose, 1967). Still further, curcumin may be obtained from commercial sources, for example, curcumin can be obtained from Sigma Chemicals Co (St. Louis, Mo.).

Any conventional method can be used to prepare curcumin and its analogues to be used in the present invention. For example, turmericoleoresin, a food additive, which essentially contains curcumin. can be produced by extracting from a dry product of rhizome of turmeric with ethanol at an elevated temperature, with hot oil and fat or propylene glycol, or with hexane or acetone at from room temperature to a high temperature. Alternatively, those can be produced by the methods disclosed in Japanese Patent Applications 2000-236843. H-11-235192 and H-6-9479, and U.S. Patent Application No. 20030147979, which is incorporated by reference herein in its entirety. In certain embodiments, a purified product of at least one curcumin and/or its analogue may be used. Alternatively, a semi-purified or crude product thereof may be used, provided that it does not contain impurities which may not be acceptable as a pharmaceutical or food product.

Preferred Analogues

There has been limited testing of the potency of curcumin analogs against beta amyloid. Park, *J. Nat. Prod.*, 65, 9, September 2002, reports testing the following curcumin analogs for the ability to provide in vitro protection for PC 12 cells against beta amyloid insult:

4"-(3'''-methoxy-4'''-hydroxyphenyl)-2"-oxo-3"-enebutanyl3-(3'-methoxy-4' hydroxyphenyl) propenoate (31);
1-(4-hydroxy-3-methoxyphenyl)-7-(4-hydroxyphenyl)-1,6-heptadiene-3,5-dione (demethoxycurcumin) (32);
1,7-bis(4-hydroxyphenyl)-1,6-heptadiene-3,5-dione (bisdemethoxycurcumin), (33); and
1,7-bis(4-hydroxyphenyl)-1-heptene-3,5-dione (34).

Each of these compounds is shown in FIG. 1D. Park reports the following results, as shown in Table IV:

TABLE IV

| Analog | anti-βA (25-35) ED50$^a$ (µg/ml) | anti-βA (1-42) ED50 (µg/ml) |
|---|---|---|
| curcumin | 7.0 +/− 1.1 | 10.0 +/− 0.9 |
| 31 | 1.0 +/− 0.3 | 2.0 +/− 0.4 |
| 32 | 4.0 +/− 0.5 | 5.0 +/− 0.5 |
| 33 | 2.0 +/− 0.6 | 3.5 +/− 0.7 |
| 34 | 0.5 +/− 0.2 | 1.0 +/− 0.3 |

$^a$ED50 represents the sample concentration that is required to achieve 50% cell viability.

Analysis of the Park data reveals that each of compounds (31)-(34) is a more potent neuroprotectant against beta amyloid than curcumin. with compounds (31) and (34) being on the order of 5-fold and 10-fold more potent. Therefore, in preferred embodiments, each of compounds (31)-(34) is used by itself or in combination as the parent compound for the manufacturing and use of a curcumin prodrug. Each of the parent compounds may be obtained by the methods disclosed in Park.

Kim, *Neuroscience Lett.* 303 (2001) 57-61 similarly reports testing the following curcumin analogs for the ability to provide in vitro protection for PC 12 cells against beta amyloid insult as shown in Table V:

TABLE V

| Analog | anti-BA (25-35) ED50 (µg/ml) | anti-BA (1-42) ED50 (µg/ml) |
|---|---|---|
| Curcumin | 7.1 +/− 0.3 | 6.8 +/− 0.4 |
| Demethoxycurcumin | 4.7 +/− 0.1 | 4.2 +/− 0.3 |
| Bisdemethoxycurcumin | 3.5 +/− 0.2 | 3.0 +/− 0.3 |

Analysis of the Kim data reveals that each of the demethoxycurcumin and bisdemethoxycurcumin compounds is a more potent neuroprotectant against beta amyloid than curcumin, with the demethoxycurcumin and bisdemethoxycurcumin compounds being on the order of 1.5 and 2 fold more potent. This data is in substantial agreement with the relative potencies of demethoxycurcumin and bisdemethoxycurcumin reported by Park above.

Other Diseases

In other embodiments, the present invention relates to the intranasal administration of a formulation comprising an effective amount of curcumin or compounds represented by Structural Formula (I) across the cribriform plate and into the brain in order to treat a stroke.

In other embodiments, the present invention relates to the intranasal administration of a formulation comprising an effective amount of curcumin or compounds represented by Structural Formula (I) across the cribriform plate and into the brain in order to treat multiple sclerosis.

Other Polyphenolic Prodrugs

In some embodiments, the curcumin or a compound represented by Structural Formula (I) is combined with a second lipophilic therapeutic agent, preferably another polyphenol, such as resveratrol. In some embodiments, the curcumin or a compound represented by Structural Formula (I) is provided in a formulation with another compound selected from the group consisting of gingko biloba extract, resveratrol, and a green tea catechin, and then is intranasally administered.

Also in accordance with the present invention, there is provided a method for transporting a gingko biloba extract to a brain of a mammal, comprising: a) applying a pharmaceutical composition comprising a gingko biloba extract to an upper third of a nasal cavity of the mammal, wherein the gingko biloba extract is absorbed through an olfactory mucosa and transported to the brain of the mammal.

Also in accordance with the present invention, there is provided a method for transporting resveratrol to a brain of a mammal, comprising:
a) applying a pharmaceutical composition comprising resveratrol to an upper third of a nasal cavity of the mammal, wherein the resveratrol is absorbed through an olfactory mucosa and transported to the brain of the mammal.

Also in accordance with the present invention, there is provided a method for transporting a green tea catechin to a brain of a mammal, comprising:
a) applying a pharmaceutical composition comprising the catechin to an upper third of a nasal cavity of the mammal, wherein the catechin is absorbed through an olfactory mucosa and transported to the brain of the mammal.

The prodrug rationale provided above for curcumin or compounds represented by Structural Formula (I) can also be applied to other therapeutic phenolic compounds (preferably, therapeutic polyphenolic compounds), such as those of the flavonoid class. In preferred embodiments, this compound is selected from the group consisting of resveratrol, hispidin, genistein, ellagic acid, 1,25 dihydroxyvitamin D3, the green tea catechin EGCG, and docosahexaenoic acid (DHA). In another embodiment, this compound is docosahexaenoic acid (DHA). Also in accordance with the present invention, there is provided a method for transporting a flavonoid prodrug to a brain of a mammal, comprising:
a) applying a pharmaceutical composition comprising a flavonoid prodrug (such as a resveratrol prodrug) to an upper third of a nasal cavity of the mammal, wherein the flavonoid prodrug is absorbed through an olfactory mucosa and transported to the brain of the mammal.

Resveratrol

In especially preferred embodiments, the flavonoid prodrug is resveratrol.

Resveratrol, a polyphenolic compound commonly found in red wine, has been promoted as a possible treatment for Alzheimer's Disease (AD) because it appears to affect multiple mechanisms of AD pathology. Anekonda, *Brain Research Reviews,* 52, 2006, 316-26.

First, resveratrol has been shown to reduce the amount of beta amyloid in brain tissue. The mechanism by which resveratrol accomplishes this has been subject to debate. One recent paper concludes that resveratrol is a specific inhibitor of BACE1 enzyme, with an IC50 of about 15 uM. Jeon, *Phyomedicine,* 2006 Nov. 2 (E-pub). Another recent paper reports that resveratrol reduces beta amyloid content by promoting intracellular degradation of beta amyloid via a mechanism that involves the proteosome. Marambaud, *J. Biol. Chem.,* 280(45), 37377-82.

Second, it is believed that resveratrol inhibits the formation of beta amyloid fibrils. Riviere, *Bioorg. Med. Chem.* 2006 October 1 (E-pub).

Third, 20 μM resveratrol has a neuroprotective effect against beta amyloid-induced neurotoxicity in rat hippocampal neurons; and is believed to provide this neuroprotection through activation of protein kinase C (PKC). Han, *Br. J. Pharmacology,* 2004, 141, 997-1005. Han, J. Pharmacol. Exp. Ther., 2006 Jul. 318(1) 238-45 (Epub 2006 Mar. 30), reports the existence of specific plasma membrane binding sites for resveratrol in the rat brain (Ki=102 nM), and notes that the potency of resveratrol analogs in protecting rat hippocampal cells against beta amyloid-induced neurotoxicity correlates well with their apparent affinity.

The hypothesis that resveratrol acts through PKC is of special interest because it is believed that nonamyloidogenic processing of amyloid precursor protein (APP) also acts through activation of PKC.

Fourth, some hypotheses of Alzheimer's Disease involve oxidation via enhanced brain concentrations of heavy metals. Respecting resveratrol, it has been reported that resveratrol is a highly potent chelator of copper. Belguendouz, *Biochemical Pharmacology,* 53, 1347-1355, 1997.

Fifth, Anekonda, *Brain Research Reviews,* 52, 2006, 316-26 reports that mechanisms of aging and AD are intricately linked and that these mechanisms can be modulated by both calorie restriction regimens and calories restriction mimetics, the prime mediator of which is the SIRT1 protein. Howitz, *Nature.* 2003, 425, 191-196 reports that resveratrol has been found to exhibit the highest level of SIRT1 activation amongst the small molecules tested. Chen, *J. Biol. Chem.,* 280, 48, 40364-74 found that resveratrol markedly reduced NF-KB signaling in microglia, and ascribed this benefit to the induction of SIRT1 by resveratrol. Similarly, Kim, *Int. J. Mol. Med.,* 2006 Jun., 17, 6, 1069-75 reports that modulation of NF-KB activity is involved in the neuroprotective action of resveratrol against beta amyloid induced neurotoxicity.

Sixth, resveratrol is a well known anti-oxidant, and 5-25 uM resveratrol has displayed an ability to protect cultured hippocampal cells against nitric oxide related neurotoxicity. Bastianetto, *Br. J. Pharm.,* 2000, 131, 711-720. Similarly, Savaskan, *Gerontology,* 2003 November-December, 49(6) 380-3 reports that resveratrol maintains cell viability against beta amyloid-related oxidative stress, and exerts its antioxidative action by enhancing the intracellular free radical scavenger glutathione.

The bioavailability of resveratrol has been well-studied. Since resveratrol appears to be highly susceptible to glucuronidation in the intestine and liver, it has been concluded that the oral bioavailability of resveratrol is "about zero". Wenzel, *Mol. Nutr. Food Res.,* 2005, 49, 472-481. Accordingly, because of the finding that trans-resveratrol in present in human serum in its glucuronide form rather than in its free form, Vitaglione, *Mol. Nutr. Food Res.,* 2005 May 49(5), 495-504, raises some doubts about the heath effect of dietary consumption of resveratrol. Thus, the intranasal rationale for trans-resveratrol appears warranted.

Nonetheless, it appears that when resveratrol reaches the brain, it has a fairly significant residence time. El-Mohsen, *British J. Nutrition,* 2006, 96, 62-70, reports that the resveratrol concentration in the brain about 18 hours after gastric administration was still 43% of that measured at 2 hours. Wang, *Brain Research,* 958 (2002), 439-447, reports that intraperitoneal administration of resveratrol provides a peak concentration in the brain 4 hours after its administration.

Trans-resveratrol has a molecular weight of about 228, and is very lipophilic (having an octanol-water partition coefficient Log P of about 3.14). However, its solubility in water is very low (<0.01 mol/L). Thus, the prodrug rationale for trans-resveratrol appears warranted.

Hybrids

FIGS. 2-16 disclose curcumin, resveratrol, and various curcumin derivatives that are hybrids of curcumin and various other natural polyphenols. Each of these derivatives is a triphenolic compound, wherein the intermediate diketone structure of curcumin is replaced with a phenolic group. The resulting compound retains the spacing between the two phenols of curcumin, and also possesses the biphenolic spacing of the additional polyphenol.

FIG. 2 discloses the structures of curcumin, resveratrol, and two curcumin-resveratrol hybrids. Note how each of the hybrids retains the interphenolic spacing of each of curcumin and reveratrol.

Figure 3:
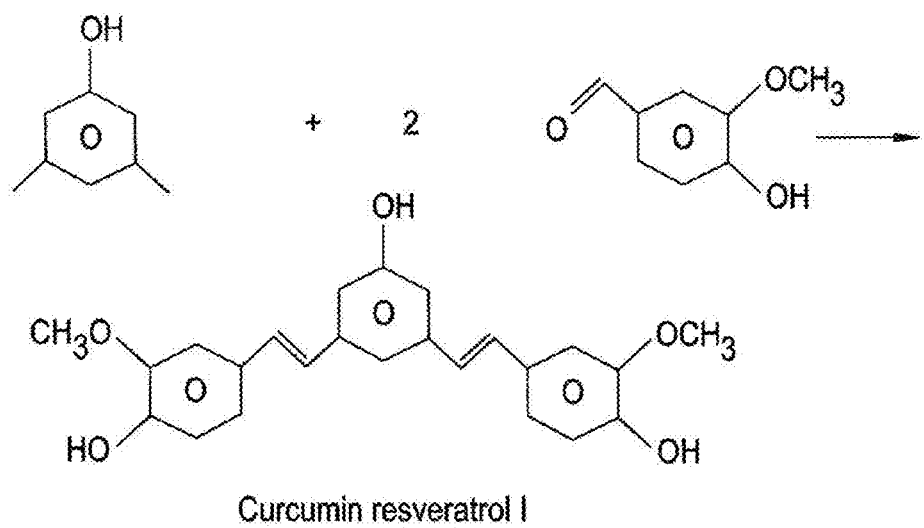

FIG. 3 discloses a method of making the curcumin-resveratrol I hybrid.

Figure 4:
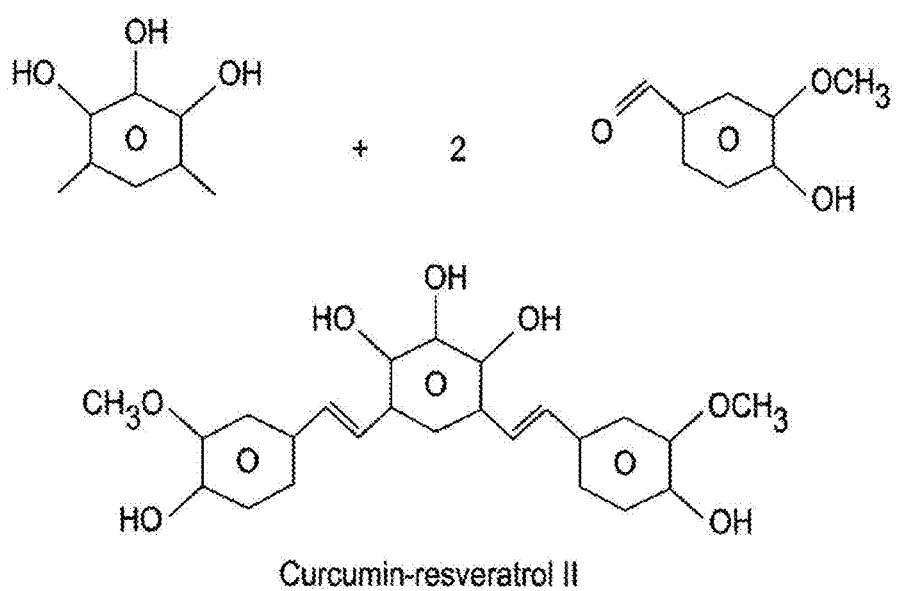

FIG. 4 discloses a method of making the curcumin-resveratrol II hybrid.

Figure 5:
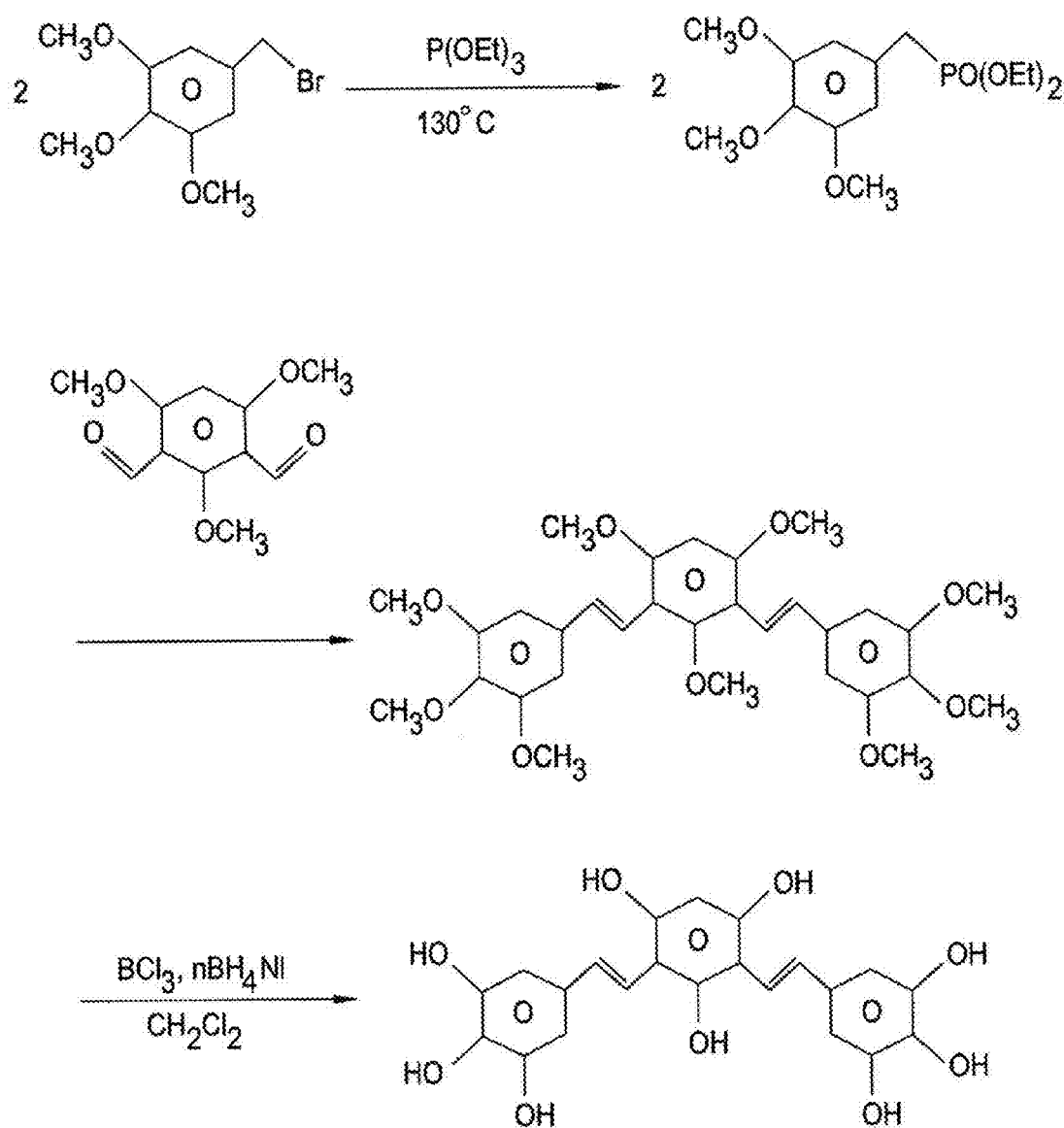

FIG. 5 discloses a method of making a curcumin-resveratrol hybrid having three hydroxyl groups in each of the central phenolic group and lateral phenolic groups.

FIG. 6 discloses curcumin, resveratrol and a hybrid thereof, wherein all of the phenolics of the natural compounds are represented in the hybrid, providing trihydroxyl lateral phenolic groups and a dihydroxyl central phenolic group.

Figure 7:
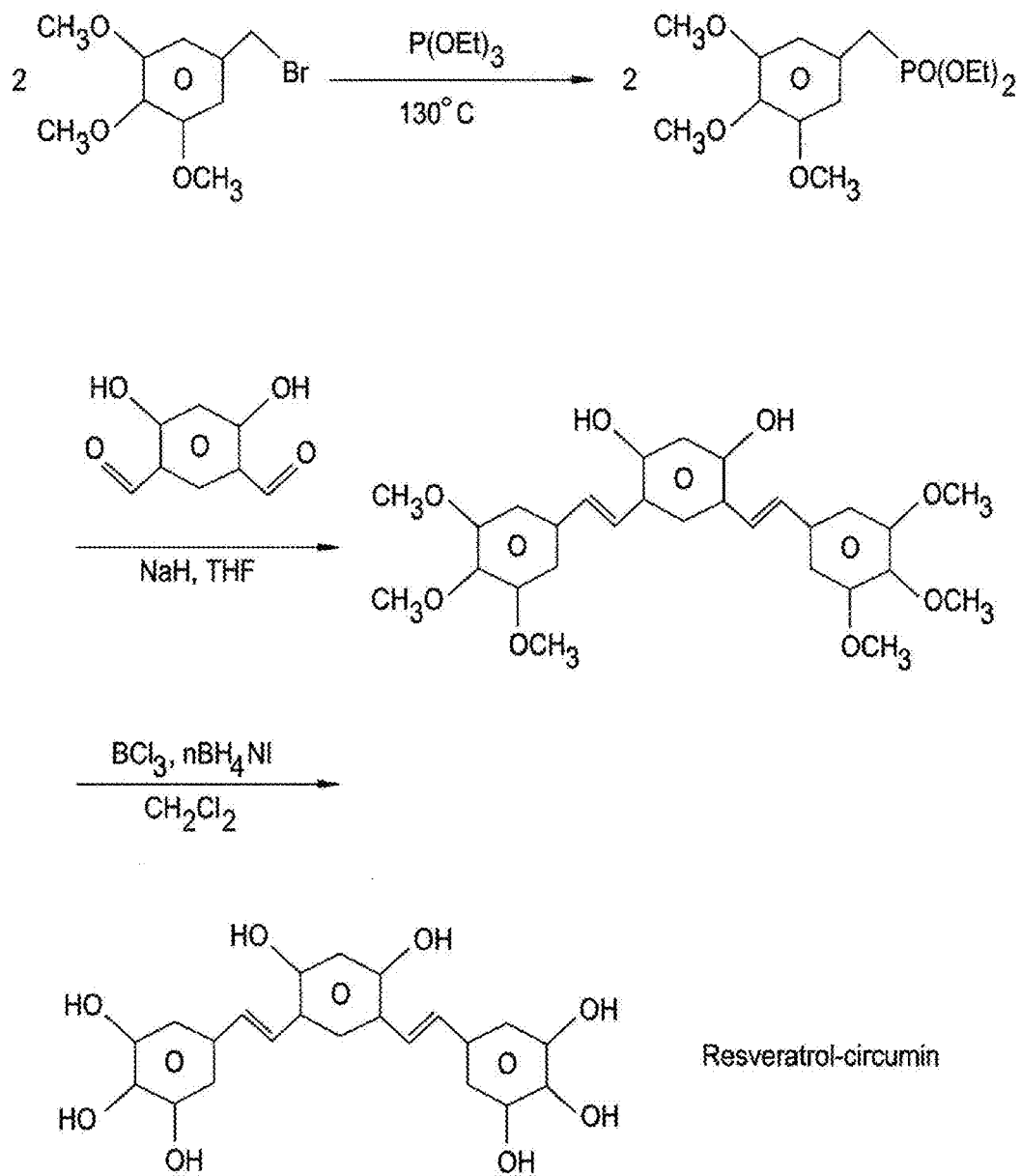

FIG. 7 discloses a method of making the curcumin-resveratrol hybrid of FIG. 6.

FIG. 8 is similar to the hybrid of FIG. 6, but wherein the methoxy groups of the base curcumin molecule are retained.

FIG. 9 discloses curcumin. oxyresveratrol and a hybrid thereof, wherein all of the hydroxyls/phenolics of the natural compounds are represented in the hybrid, providing trihydroxyl lateral phenolic groups and a trihydroxyl central phenolic group.

Figure 10:
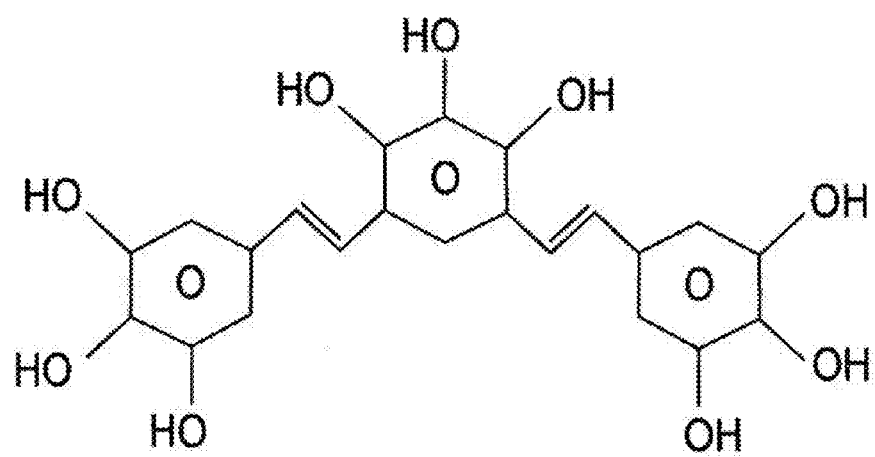

FIG. 10 discloses curcumin, piceatannol and a hybrid thereof, wherein all of the hydroxyls/phenolics of the natural compounds are represented in the hybrid, providing trihydroxyl lateral phenolic groups and a trihydroxyl central phenolic group.

Figure 11:
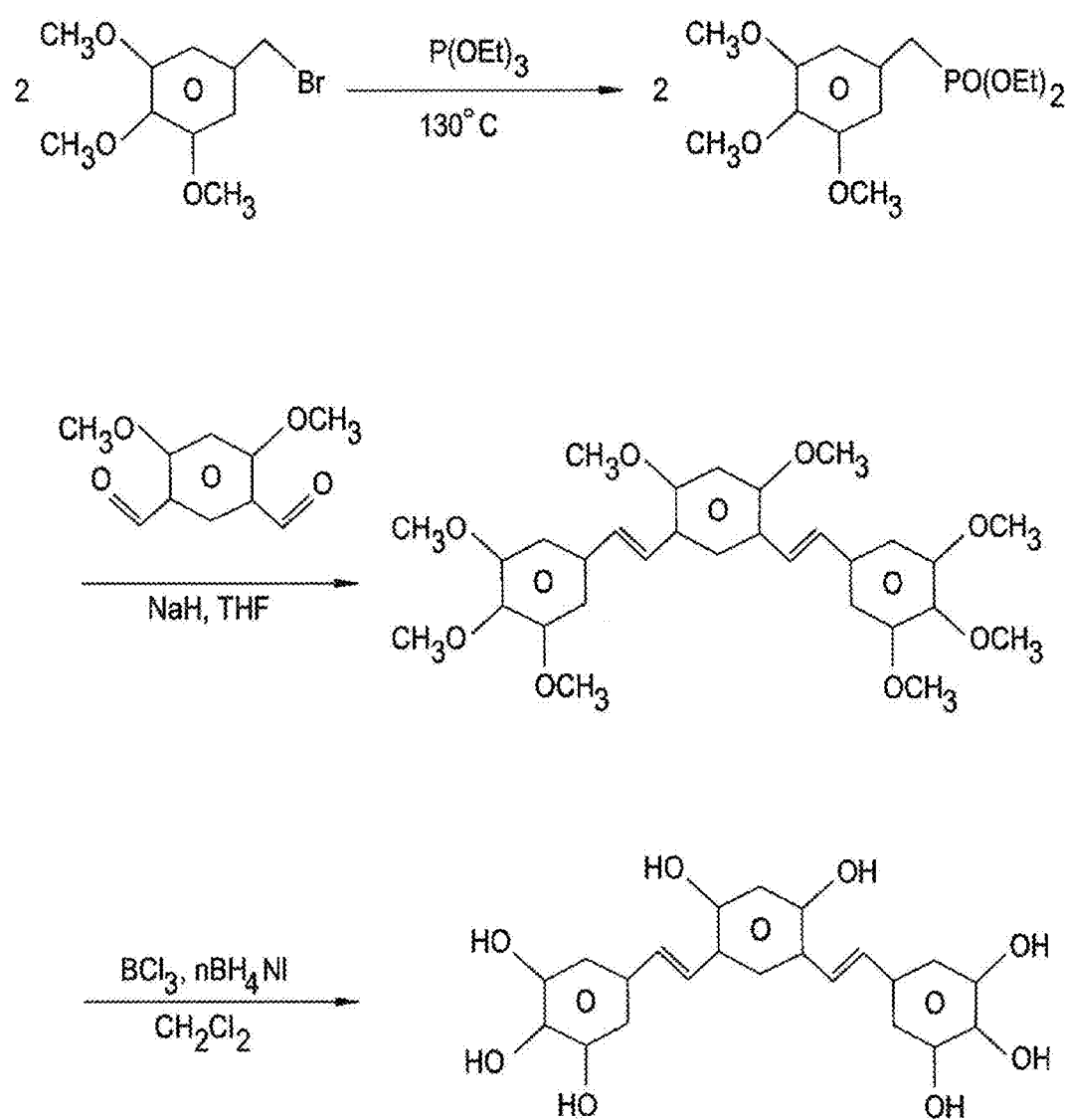

FIG. 11 discloses a method of making a curcumin-resveratrol hybrid, wherein all of the hydroxyls/phenolics of the natural compounds are represented in the hybrid, providing trihydroxyl lateral phenolic groups and a dihydroxyl central phenolic group.

Figure 12:
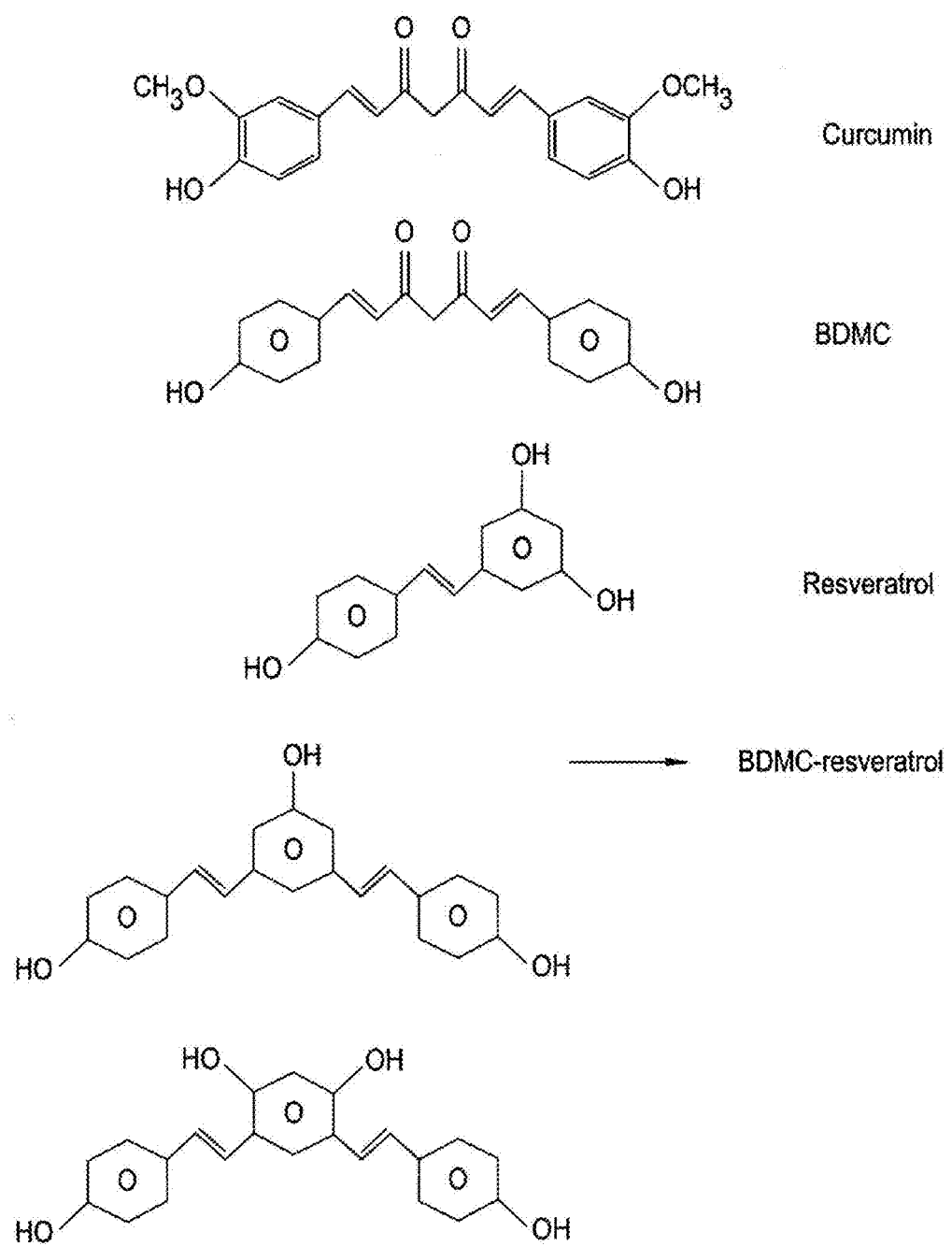

FIG. 12 discloses curcumin. bisdemethoxycurcumin (BDMC), resveratrol and curcumin hybrids thereof, wherein all of the phenolics of the natural compounds are represented in the hybrid, providing hydroxyl demethoxy lateral phenolic groups and a hydroxy or dihydroxyl central phenolic group.

Figure 13:
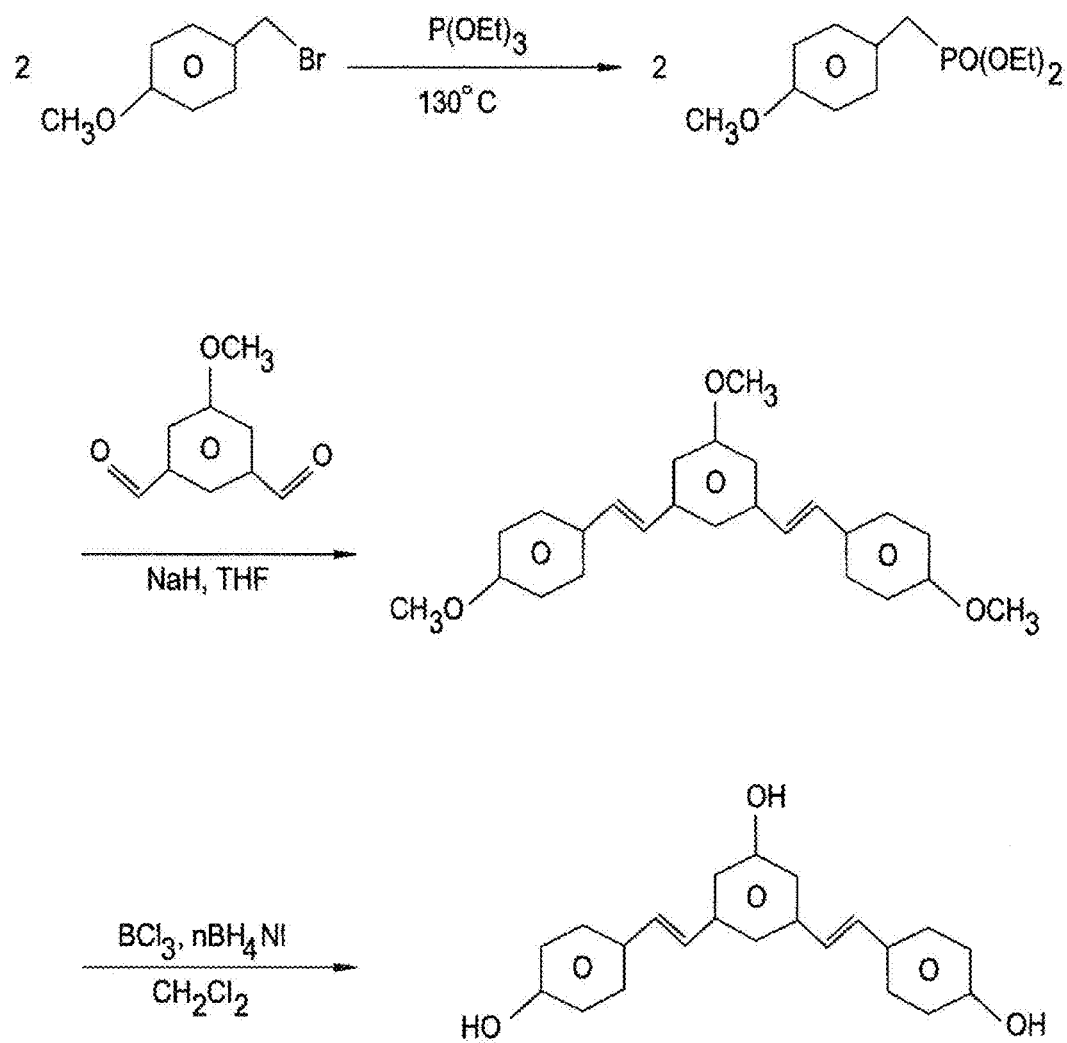

FIG. 13 provides a method of making the compound of FIG. 12 that has hydroxyl demethoxy lateral phenolic groups and a hydroxy central phenolic group.

Figure 14:
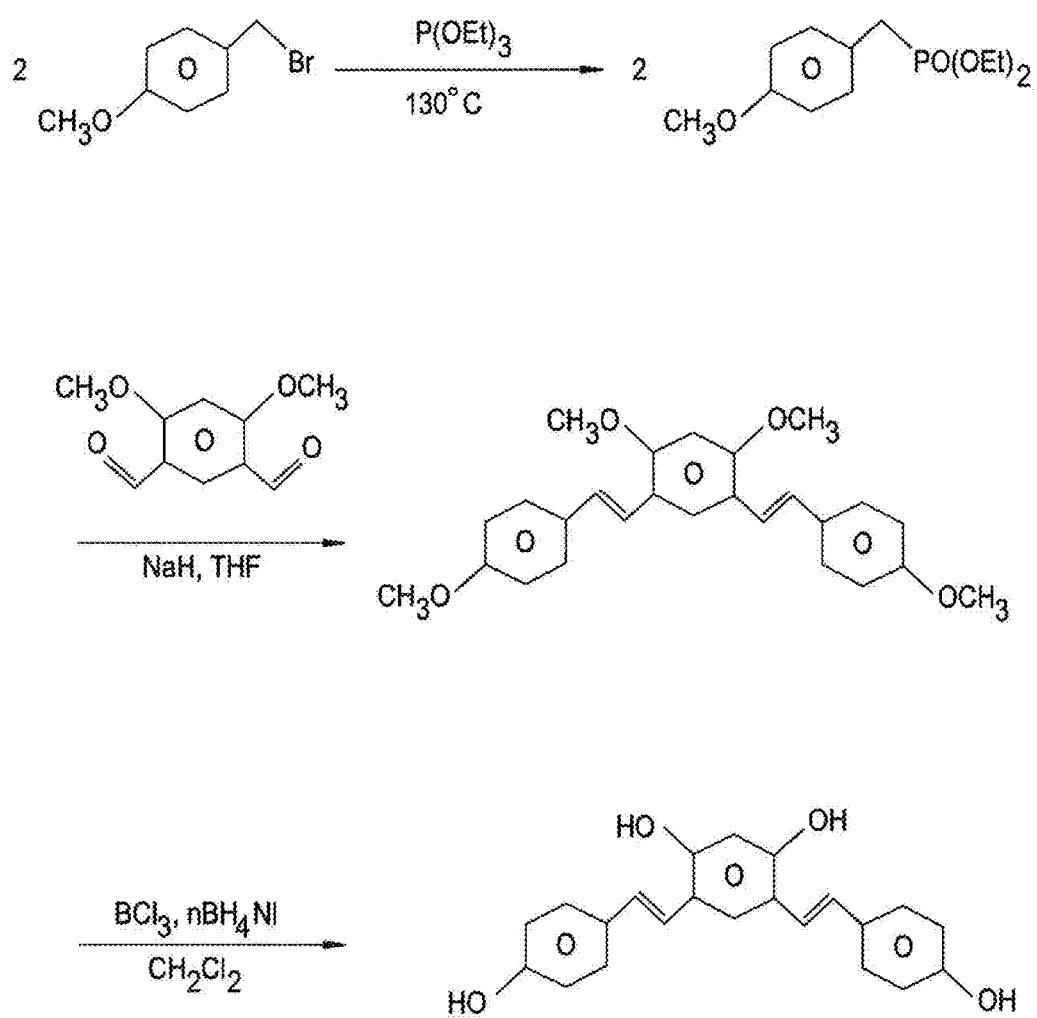

FIG. 14 provides a method of making the compound of FIG. 12 that has hydroxyl demethoxy lateral phenolic groups and a dihydroxy central phenolic group.

FIG. 15 discloses curcumin, fisetin and hybrids thereof, wherein all of the phenolics of the natural compounds are represented in the hybrid, providing dihydroxyl phenolic groups and a hydroxy central phenolic group in the positions common with the two natural compounds.

Figure 16:
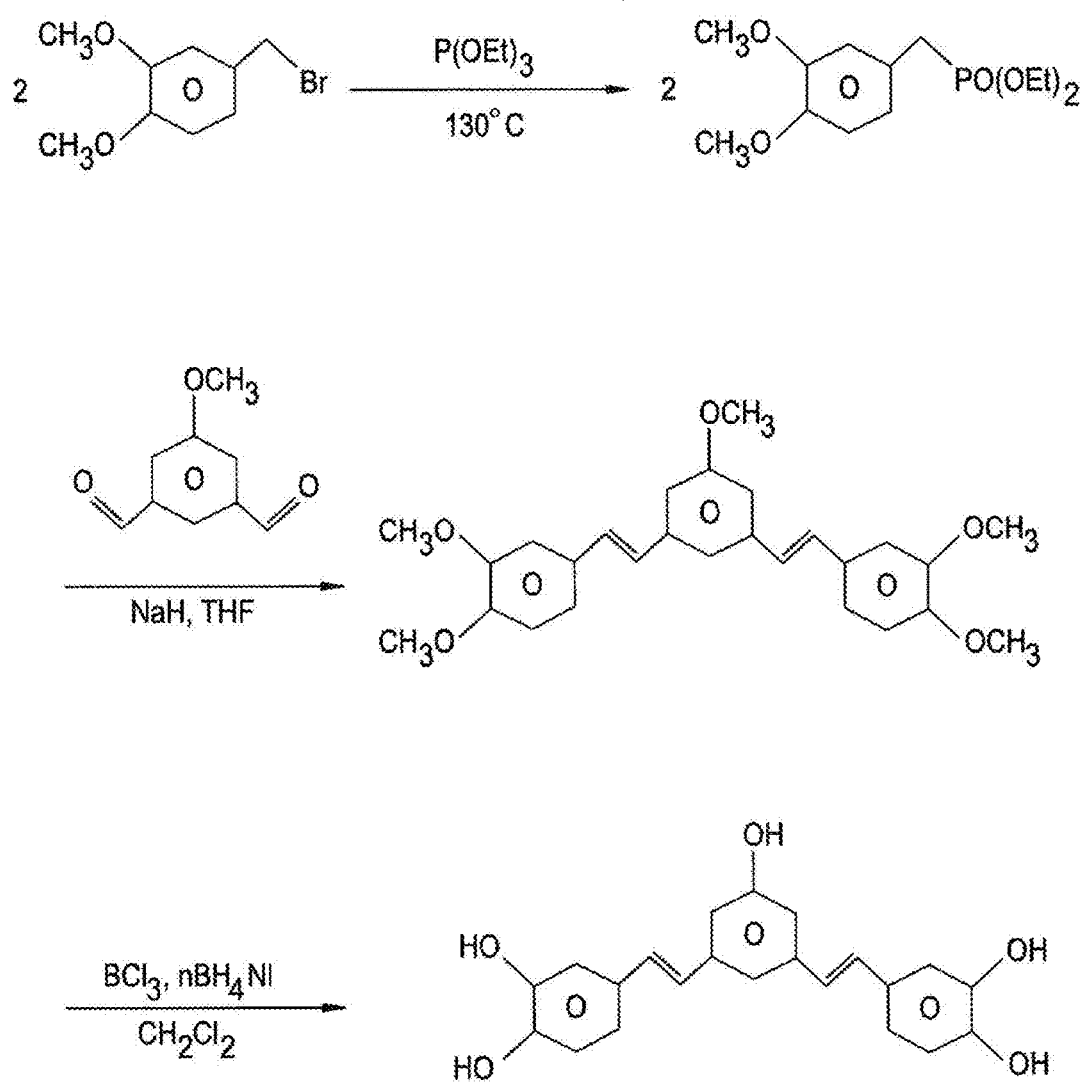

FIG. 16 provides a method of making the compound of FIG. 15.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating a subject with Alzheimer's disease, the method comprising administering to the subject an effective amount of a compound represented by the following structural formula:

[structure]

or a pharmaceutically acceptable salt thereof, wherein:
$R_1$ is —OH or —O—$(C_1$-$C_6)$alkyl;
each $R_2$ and $R_3$ are independently selected from the group consisting of —OH, —O$(C_1$-$C_6)$alkyl, halo, —C(Y)$_3$ and —OP;
Y is a halogen;
P is selected from the group consisting of —C(O)—$(C_1$-$C_6)$alkylene—N($R_5$)($R_6$),

[structure]

—C(O)—N($R_7$)—$(C_1$-$C_6)$alkylene-COOH, —C(O)—$(C_1$-$C_6)$alkylene-heterocyclyl and —C(O)—$(C_1$-$C_6)$alkylene-aryl;
each $R_4$ $R_5$ and $R_6$ are independently selected from —H and $(C_1$-$C_6)$alkyl;
$R_7$ is —H or $(C_1$-$C_4)$alkyl;
$X^-$ is an anion;
n is an integer from 1 to 4;
m is an integer from 1 to 5; and
p is an integer from 1 to 5,
wherein each alkyl is optionally substituted with one or more substituents independently selected from —OH, —O—$(C_1$-$C_4)$alkyl, —COOH, —O—C(O)—$(C_1$-$C_4)$alkyl, —N($R_7$)$_2$ and —$\overset{+}{N}$ $(R_7)_3 X^-$, $R_2$ and $R_3$ are the same, and m and p are the same.

2. A method of treating a subject with Alzheimer's disease, the method comprising administering to the subject an effective amount of a compound represented by the following structural formula:

[structure]

or a pharmaceutically acceptable salt thereof, wherein:
- - - - represents a single bond or a double bond;
each $R_1$, $R_2$ and $R_3$ are independently selected from the group consisting of —OH, —O$(C_1$-$C_6)$alkyl, halo, —C(Y)$_3$ and —OP;

Y is a halogen;

P is selected from the group consisting of —C(O)—(CH$_2$)$_{1-3}$—N(R$_5$)(R$_6$),

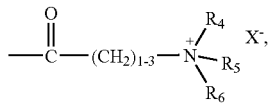

—C(O)—NH—(CH$_2$)$_{1-3}$—COON, —C(O)—(CH$_2$)-heterocyclyl and —C(O)—(CH$_2$)-phenyl;

each R$_4$, R$_5$ and R$_6$ are independently selected from —H and (C$_1$-C$_6$)alkyl;

R$_7$ is —H or (C$_1$-C$_4$)alkyl;

X$^-$ is an anion;

n is an integer from 1 to 4;

m is an integer from 1 to 5; and p is an integer from 1 to 5, wherein each alkyl is optionally substituted with one or more substituents independently selected from —OH, —O—(C$_1$-C$_4$)alkyl, —COOH, —O—C(O)—(C$_1$-C$_4$)alkyl, —N(R$_7$)$_2$ and —$\overset{+}{N}$(R$_7$)$_3$X$^-$.

3. A method of treating a subject with Alzheimer's disease, the method comprising administering to the subject an effective amount of a compound represented by the following structural formula:

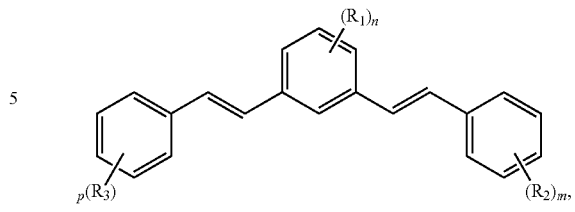

or an ester prodrug or a pharmaceutically acceptable salt thereof, wherein:

each R$_1$, R$_2$ and R$_3$ are independently selected from the group consisting of —OH and —OCH$_3$;

n is an integer from 1 to 4;

m is an integer from 1 to 5; and p is an integer from 1 to 5.

4. The method of claim 3, wherein the ester prodrug contains an aminoalkylcarboxylic acid.

5. The method of claim 4, wherein the aminoalkylcarboxylic acid is an aminoalkanecarboxylic acid.

6. The method of claim 5, wherein the aminoalkanecarboxylic acid is a glycinate moiety.

7. The method of claim 3, wherein the ester prodrug is in the form of a salt.

8. The method of claim 7, wherein the salt comprises an anion selected from the group consisting of chloride, iodide, and bromide.

* * * * *